(12) United States Patent
Levine

(10) Patent No.: US 6,432,914 B1
(45) Date of Patent: Aug. 13, 2002

(54) BECLIN AND USES THEREOF

(75) Inventor: Beth C. Levine, Briarcliff Manor, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 09/265,630

(22) Filed: Mar. 9, 1999

Related U.S. Application Data

(63) Continuation-in-part of application No. 09/250,045, filed on Feb. 12, 1999, now abandoned, which is a continuation-in-part of application No. 09/040,808, filed on Mar. 18, 1998, now abandoned, which is a continuation-in-part of application No. PCT/US97/16358, filed on Sep. 12, 1997, now abandoned, which is a continuation-in-part of application No. 08/712,939, filed on Sep. 13, 1996, now Pat. No. 5,858,669.

(51) Int. Cl.$^7$ .............................................. A01N 37/18

(52) U.S. Cl. ................................ 514/2; 514/2; 514/12; 514/21; 435/6; 435/7.1; 530/300; 530/350

(58) Field of Search ................................ 530/350, 300; 514/2, 12, 21; 435/7.1, 6

(56) References Cited

U.S. PATENT DOCUMENTS 5,858,669 A    1/1999    Levine .......................... 435/6

OTHER PUBLICATIONS

Alsopp, T.E., Scallan, M.F., Williams, A., and Fazakerley, J.K., (1998) "Virus infection induces neuronal apoptosis: a comparison with trophic fact of withdrawal", *Cell Death Differ.*, 5:50–59 (Exhibit 1); and.

Cropp, C,S., Champeme, M.H., Lidereau, R., and Callahan, R., (1993) "Identification of three regions on chromosome 17q in primary human breast carcinomas which are frequently deleted", *Cancer Res.*, 53:3382–3385 (Exhibit 2).

Aita, V.M., et al. (1999) "Cloning and Genomic Organization of Beclin 1, a Candidate Tumor Suppressor Gene on Chromosome 17q21", *Genomics*, 59:59–65.

Friedman, L.S., et al., (1995) "22 Genes From Chromosome 17q21: Cloning, Sequencing and Characterization of Mutations in Breast Cancer Families and Tumors", *Genomics*, 25:256–263. (Exhibit 3).

Gordon, G.W., et al., (1998) "Quantitative Fluorescence Resonance Energy Tranfer Measurements Using Fluorescence Microscopy", *Biophysical Journal*, 74:2702–2713 (Exhibit 4).

Liang, X.H., et al., (1999) "Induction of Autophagy and Inhibition of Tumorigenesis by Beclin 1", *Nature*, 402:672–676. (Exhibit 5).

Rommens, J.M., et al., (1995) "Generation of a Transcription map at the HSD17B Locus Centromeric to BRCA1 at 17q21", *Genomics*, 28:530–542. (Exhibit 6).

Blommaart, E.F.C., et al., (1995) "Posphorylation of ribosomal protein S6 is inhibitory for authophagy isolated rat hepatocytes", *J. Biol. Chem.*, 270:2320–2326 (Exhibit 1).

Gronostajski, R.M., and Pardee, A.B., (1984) "Protein degradation in 3T3 and tumorigenic transformed 3T3 cells" *J.Cell. Physiol*, 119:127–132 (Exhibit 2).

Gunn, J.M., et al., (1977) "Reduced rates of proteolysis in transformed cells" *Nature*, 266:58–60 (Exhibit 3).

Hinshaw, V.S., Olsen, C.W., Dybdahl–Sissoko, N., and Evans, D., (1994) "Apoptosis: a mechanism of cell killing by influenza A and B viruses", *J. Virol.*, 68:3667–3673 (Exhibit 4).

Kisen, G.O., et al., (1993) "Reduced autophagic activity in primary rat hepatocellular carcinoma and ascites hepatoma cells", *Carcinogenesis*, 14:2501–2505 (Exhibit 5).

Knecht, E., Hernandez–Yago, J., and Grisolia, S., (1984) "Regulation of lysosomal authophagy in transformed and non–transformed mouse fibroblasts under several growth conditions" *Exp. Cell. Res.*, 154:224–232 (Exhibit 6).

Levine, B., Goldman, J.E., Jiang, H.H., Griffin, D.E., and Hardwich, J.M., (1996) "Bcl–2 proteins mice against fatal alphavirus encephalitis", *Proc. Natl. Acad. Sci. USA*, 93:4810–4815 (Exhibit 7).

Lewis, J., Wesslingh, S.L., Griffin, and Hardwich, J.M., (1996) "Alpha–virus induced apoptosis in mouse brains correlates with neurovirulence" *J. Virol.*, 70:1828–1835 (Exhibit 8).

(List continued on next page.)

*Primary Examiner*—Karen Cochrane Carlson
*Assistant Examiner*—Hope A. Robinson
(74) *Attorney, Agent, or Firm*—John P. White; Cooper & Dunham LLP

(57) ABSTRACT

This invention provides a method of diagnosing a predisposition to carcinoma in a subject comprising: a) obtaining a nucleic acid sample from the subject; b) determining whether one or moire of the subject's beclin alleles or regulatory regions to those alleles are deleted or different from the wild type so as to reduce the subject's expression of polypeptide having tumor suppressor activity; and c) determining whether one or more of the subject's beclin alleles or regulatory regions to those alleles are deleted or changed so as to reduce the subject's ability to mediate autophagey. This invention also provides uses of beclin for treating viral diseases. This invention provides a method for inhibiting viral replication comprising contacting effective amount of Beclin with the virus infected cell, thereby inhibiting the viral replication. This invention also provides a method for inhibiting viral replication comprising contacting induction of the expression of beclin with the virus infected cell, thereby inhibiting the viral replication. This invention also provides a method for treating cancer comprising inducing increased expression of Beclin, thereby restoring autophagy as well as a method for treating cancer which comprises administering to the subject a therapeutically effective amount of beclin so as to restore autophagy.

3 Claims, 41 Drawing Sheets

OTHER PUBLICATIONS

Liang, X.H., Volkmann, M., Klein, R., Herman, B., and Lockett, B., (1994) "Colocalization of Tumor suppressor protein p53 and human papillomavirus E6 protein in human cervical carcinoma cell lines" *Oncogene*, 8:2645–2652 (Exhibit 9).

Liang, X.H., et al., (1998) "Protection against Fatal Sindbis Virus Encephalitis by Beclin, a Novel Bcl–2–Interacting Protein" *J. Virol.*, 72:8586–8596 (Exhibit 10).

Loda, M., et al., (1997) "Increased proteasome–dependent degradation of the cyclindependent kinase ihibitor p27 in aggressive colorectal carcinomas" *Nature Med.*, 3:231–234 (Exhibit 11).

Lupas, A., Van Dyke, M., and Stock, M.J., (1991) "Predicting coiled coils from protein sequences" *Sci.*, 252:1162–1164 (Exhibit 12).

Mizushima, N., et al., (1998) "A protein conjugation system essential for autoghagy" *Nature*, 395:395–398 (Exhibit 13).

Olsen, C.W., Kehren, J.C., Dybdahi–Sissoki, N.R., and Hinshaw, V.S., (1996) "bcl–2 alters influenza virus, yield spread, and hemagglutinin glycosylation" *J. Virol.*, 80:663–666 (Exhibit 14).

Oltavi, Z., Milliman, C.L., and Korsmeyer, S.J., (1993) "Bcl–2–heterodimerizes in vivo with a conserved homolog, Bax, that accelerates programmed cell death" *Cell*, 74:609–619 (Exhibit 15).

Otsuka, H., and Moskowitz, M., (1978) "Differences in the rates of protein degradation in untransformed cell lines" *Exp. Cell. Res.*, 112:127–135 (Exhibit 16).

Reed, J.C. (1997) "Double identity for proteins of the Bcl–2 family" *Nature*, 387:773–776 (Exhibit 17).

Soares, M.B., Bonaldo, M.F. Jelene, P., Su, L. Lawton, L., and Efstradiadis, A., (1994) "Construction and characterization of a normalized cDNA library" *Proc. Natl. Acad. Sci. USA*, 91:9228–9232 (Exhibit 18).

```
1/1
ATG GAA GGG TCT AAG ACG TCC AAC AAC AGC ACC ATG CAG GTG AGC TTC GTG TGC CAG CGC TGC AGC CAG CCC CTG AAA CTG GAC ACG AGT
 M   E   G   S   K   T   S   N   N   S   T   M   Q   V   S   F   V   C   Q   R   C   S   Q   P   L   K   L   D   T   S
91/31                                       31/11                                              61/21                                       151/51
TTC AAG ATC CTG GAC CGT GTC ACC ATC CAG GAA CTC ACA GCT CCA CTT GAT GGT TTC CGC ACC ACA GCC CAG GCG AAA CTA GGA GAG ACC CAG GAG GAA
 F   K   I   L   D   R   V   T   I   Q   E   L   T   A   P   L   D   G   F   R   T   T   A   Q   A   K   P   G   E   T   Q   E   E
181/61                                      211/71                                                                            241/81
GAG ACT AAC TCA GGA GAG GAG CCA TTT ATT GAA ACT CCT CGC CAG GAT GGT GTC TCT CGC AGA TTC ATC CCC CCA GCC AGA ATG ATG TCC
 E   T   N   S   G   E   E   P   F   I   E   T   P   R   Q   D   G   V   S   R   R   F   I   P   P   A   R   M   M   S
271/91                                                                              301/101                                             331/111
ACA GAA AGT GCC AAC AGC TTC ACT CTG ATT GGG GAG GTA TCT GAT GGC GGC ACC ATG GAG AAC CTC AGC AGA AGA CTG AAG GTC ACT GTG
 T   E   S   A   N   S   F   T   L   I   G   E   V   S   D   G   G   T   M   E   N   L   S   R   R   L   K   V   T   G
361/121                                                             391/131                                             421/141
GAC CTT TTT GAC ATC ATG TCG GGC CAG ACA GAT GTG GAT CAC CCA CTC TGT GAG GAA TGC ACA GAT ACT CTT TTA GAC CAT CAG CAG GAC ATT
 D   L   F   D   I   M   S   G   Q   T   D   V   D   H   P   L   C   E   E   C   T   D   T   L   L   D   H   Q   Q   D   I   T
451/151                                     481/161                                                                            511/171
CAG CTC AAC GTC ACT GAA AAT GAG TGT CAG AAC TAC AAA CGC TGT TTG GAG ATC TTA GAG CAA ATG AAT GAT GAC AAG ATA AAA CGA CAG CAG TTT
 Q   L   N   V   T   E   N   E   C   Q   N   Y   K   R   C   L   E   I   L   E   Q   M   N   D   D   K   I   K   R   Q   Q   F
541/181                                                                             571/191                                             601/201
CAG ATG GAG CTA AAG GAG CTA GAG GAG CTG ATC CAG GAG GAG CTG CAG GAG CTG GAA GAC TAT CAG AGA GAA TTT GAA AAG ATA CGA GAA GTG
 Q   M   E   L   K   E   L   E   E   L   I   Q   E   E   L   Q   E   L   E   D   Y   Q   R   E   F   E   K   I   R   E   V
631/211                                                                             661/221                                             691/231
AAT CTC GAG AAG GTC CAG GCT GAG GCT GAG AGA CTG GAT CAG GAA GAA CAG CTG GAT CAG GAA TAC CAG AGA GAA TTT GAA AAG ACC AAC GTC TTT
 N   L   E   K   V   Q   A   E   A   E   R   L   D   Q   E   E   Q   L   D   Q   E   Y   Q   R   E   F   E   K   T   N   V   F
721/241                                     751/251                                                                            781/261
CTG GAG CTG GAT GAT GAG AAG CTG AAG AGT GTT GAA AAC CAG AAC CAG ATG CGT TAT GCC CAG ATC AAT AAC TTC AGG GCC ATT AAG GAG CTG CCG
 L   E   L   D   D   E   K   L   K   S   V   E   N   Q   N   Q   M   R   Y   A   Q   I   N   N   F   R   A   I   K   E   L   P
811/271                                                                             841/281                                             871/291
AAT GCA ACC TTC CAC ATC TGG ACT CTG TTG CTC CTC CAT GCT CTG ACA GAC AAA TCT GCT AAG GAG CTG CAG CAG TTC AAA GAA GAC GAG AAG
 N   A   T   F   H   I   W   T   L   L   L   L   H   A   L   T   D   K   S   A   K   E   L   Q   Q   F   K   E   D   E   K
901/301                                                                             931/311                                             961/321
AAT GAG ATT AAT GCT GCT TGG GGC CAG ACT TAT CTA TCA TAC AAC CAT GCA ATG GTG GAG AAA GCC AAG ATT GAG GAC ACA GGA GGA AGT GGC
 N   E   I   N   A   A   W   G   Q   T   Y   L   S   Y   N   H   A   M   V   E   K   A   K   I   E   D   T   G   G   S   G
991/331                                     1021/341                                                                           1051/351
GTT CCT TAC GGA AAC CAT TCA TAT CTG GAG TCT CTG ACA GAC AAA TCT CTT AAG GAG CTG CCG TTA TAC TGT TTT GTC CAG AGA TAC CGG TTT TTT
 V   P   Y   G   N   H   S   Y   L   E   S   L   T   D   K   S   L   K   E   L   P   L   Y   C   F   V   Q   R   Y   R   F   F
1081/361                                                                            1111/371                                            1141/381
TGG GAC AAC AAG TTT GAC CAT GCA CAT GTA GCT TTC CTC GAC TGT GTG CAG CAG TTC AAA GAA GAA GTG GAA AAG GGT GAA ACC AGT TTT
 W   D   N   K   F   D   H   A   H   V   A   F   L   D   C   V   Q   Q   F   K   E   E   V   E   K   G   E   T   S   F
1171/391                                                                            1201/401                                            1231/411
TGT CTT CCC TAC AGG ATG GAT GTG GAG AAA GGC AAG ATT GAA GAC ACG GGC AGT GGC GGC GGC AGT TCC TAT TCC ATC AAA ACG CAA TTT AAC
 C   L   P   Y   R   M   D   V   E   K   G   K   I   E   D   T   G   S   G   G   G   S   S   Y   S   I   K   T   Q   F   N
1261/421                                    1291/431                                                                           1321/441
TCT GAG GAG CAG CGG ACA AAA AAA GCT CTC AAG TTC ATG CTG ACG AAT CTT AAG TGG GGT CTT GCT TGG GTG TCC TCA CAA TTT TAT AAC AAA
 S   E   E   Q   W   T   K   K   A   L   K   F   M   L   T   N   L   K   W   G   L   A   W   V   S   S   Q   F   Y   N   K
1351/451
TGA
  *
```

FIGURE 3A 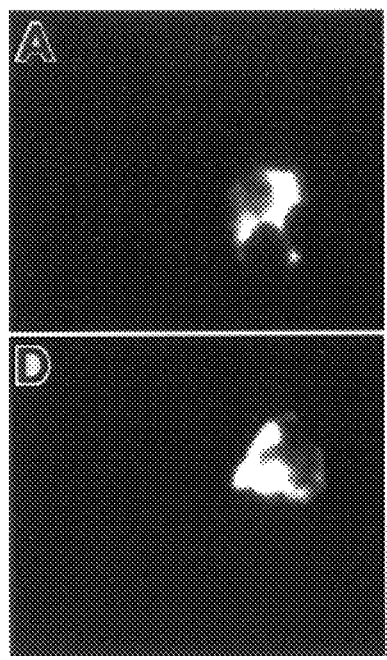 FIGURE 3B 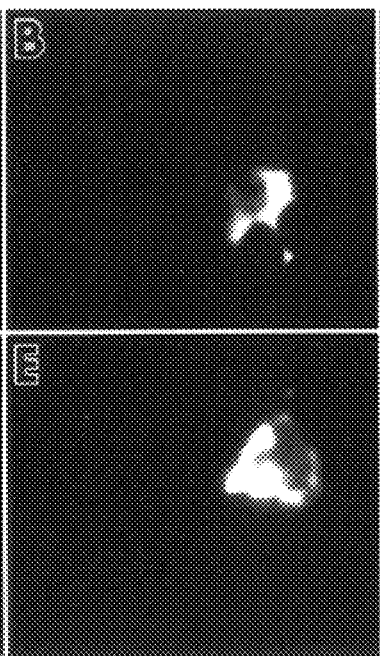 FIGURE 3C 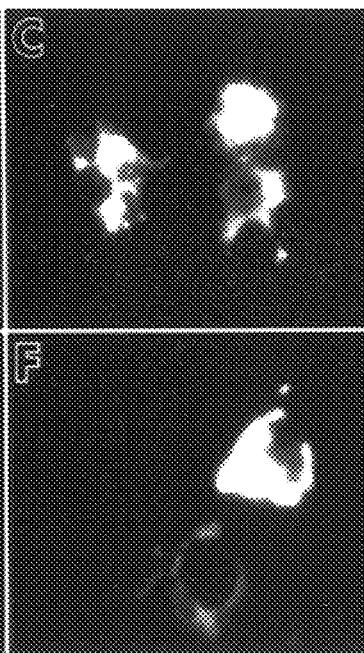
FIGURE 3D FIGURE 3E FIGURE 3F

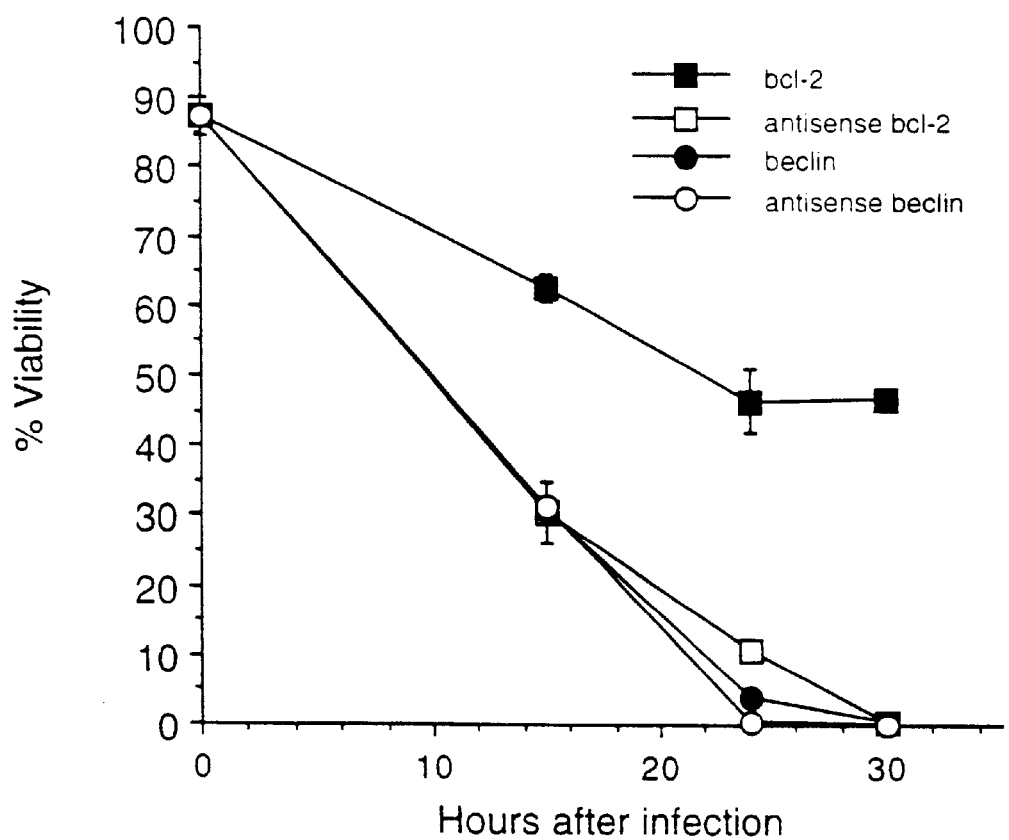

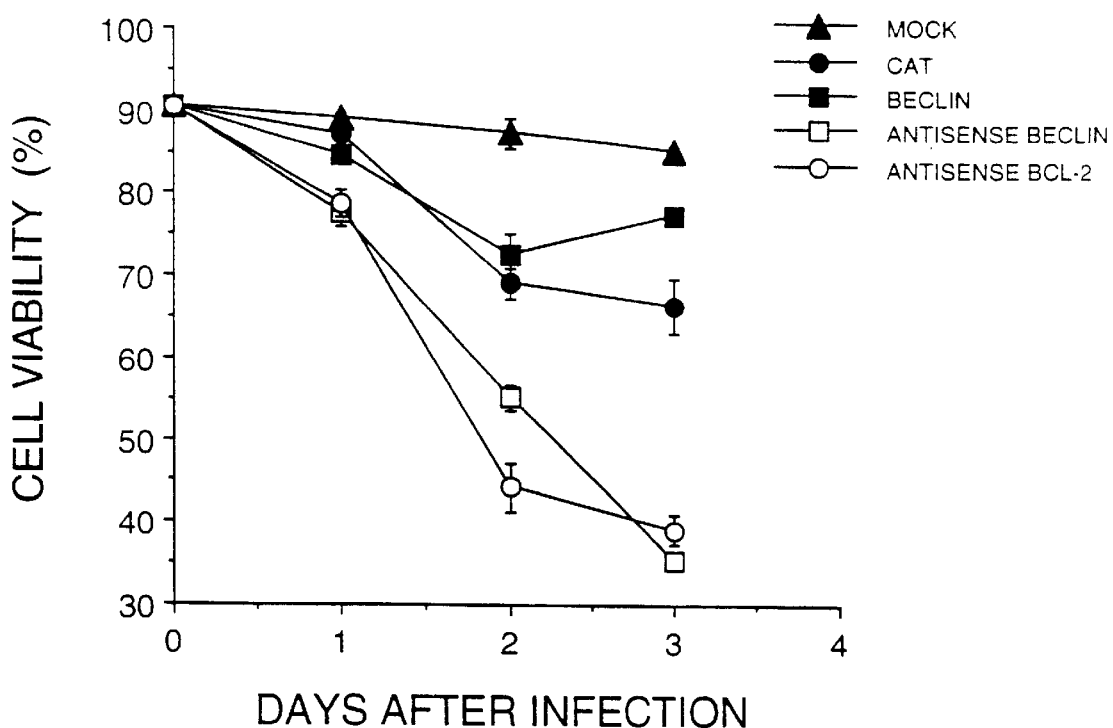

FIGURE 8A

Beclin 5' UTR - clone 5 cgggaagtcgctgaagacagagagcgatggtagttctggaggcctcgctccgggccgaccc
gaggccacagtgcctccgcggtccggtagaccggacttggggtgacgggctccccgaggg

FIGURE 8B

Beclin 3' UTR - clone 13 cttttttccttaggggggaggtttgcccttaaaggctttttaattttgttttgtttgcaaac
atgttttaaattaaattcgggtaatattaaacagtacatgtttacaatgttacaaaaagaa
aaaatccacaaaagccactttatttaaaatatcatgtgacagatactttccagagctac
aacatgccatctatagttgccagcctggtttgattcttaaccccatggactcct
ttccctttctctctgaaaaaaactaatttgctttttctttttaactgagtt
gaattgagattgatgtgttttcactggatttatctctctcaacttcctgcacttaaca
atatgaaatagaaactttgtctttactgagatgaggatatgtttgagatgcacagttgg
ataatgtgggaaaatgacatctaagctttaccggttcttcttatactgaatgccgactctgtgttaga
tgaaatttaacacttttcacttggttcttcactggttgatactgtttgagacattatggagagatttgtaat
gatatgaatggtgtttgatactgtttgagacattatggagagatttaattatttgtaat
aaaagatttgctgcagtctgaaaaccggaaaaaaaaaaaaaaaaaa

FIGURE 9B

```
1/1                                                              31/11                                              61/21
ATG GAA GGG TCT AAG ACG TCC AAC AAC AGC ATG CAG GTG AGC TTC GTG TGC CAG CGC TGC AGC CAG CCC CTG AAA CTG GAC ACG AGT
 M   E   G   S   K   T   S   N   N   S   M   Q   V   S   F   V   C   Q   R   C   S   Q   P   L   K   L   D   T   S
91/31                                                           121/41                                              151/51
TTC AAG ATC CTG GAC CGT GTC ACC ATC CAG GAA CTC ACA GCT CCA TTA CTT ACC ACA CTT ACC CAG GCG AAA CCA GGA GAG ACC CAG GAA
 F   K   I   L   D   R   V   T   I   Q   E   L   T   A   P   L   L   T   T   A   Q   A   K   P   G   E   T   Q   E
181/61                                                          211/71                                              241/81
GAG ACT AAC TCA GGA GAG GAG CCA TTT ATT GAA ACT CCT CGC CAG GAT GGT GTC TCT CGC AGA TTC ATC CCC CCA GCC AGG ATG ATG TCC
 E   T   N   S   G   E   E   P   F   I   E   T   P   R   Q   D   G   V   S   R   R   F   I   P   P   A   R   M   M   S
271/91                                                          301/101                                             331/111
ACA GAA AGT GCC AAC AGC TTC ACT CTG ATT GGG GAG GCA TCT GAT GGC GGC ACC ATG GAG AAC CTC AGC CGA AGA CTG AAG GTC ACT GGG
 T   E   S   A   N   S   F   T   L   I   G   E   A   S   D   G   G   T   M   E   N   L   S   R   R   L   K   V   T   G
361/121                                                         391/131                                             421/141
GAC CTT TTT GAC ATC ATG TCG GGC CAG ACA GAT GTG GAT CAC CCA CTC TGT GAG GAA TGC ACA GAT ACT CTT TTA GAC CAG CTG GAC ACT
 D   L   F   D   I   M   S   G   Q   T   D   V   D   H   P   L   C   E   E   C   T   D   T   L   L   D   Q   L   D   T
451/151                                                         481/161                                             511/171
CAG CTC AAC GTC ACT GAA AAT GAG TGT CAG AAC TAC AAA CGC TGT TTG GAG ATC CTG ATC CAG GAG GAC AGT GAA AAG AAT CGC AAG ATA GTG GCA GAA
 Q   L   N   V   T   E   N   E   C   Q   N   Y   K   R   C   L   E   I   L   I   Q   E   D   S   E   K   N   R   K   I   V   A   E
541/181                                                         571/191                                             601/201
CAG ATG GAG CTA AAG GAG GTC GCA CTA GAG GAG CTG CAG GAG GAA GCT CAG ACG TAT CAG ACA CAG ATC TTA AAA CGA CAG CAG
 Q   M   E   L   K   E   V   A   L   E   E   L   Q   E   E   A   Q   T   Y   Q   T   Q   I   L   K   R   Q   Q
631/211                                                         661/221                                             691/231
AAT CTC GAG AAG GTC CAG GCT GAG CTG AAG AGT GTT GAA AAC CAG AGT CGT CTC CTC CAT GCT CTG GCC AAT TTC AAG AAC ACC AAC GTC TTT
 N   L   E   K   V   Q   A   E   L   K   S   V   E   N   Q   M   R   Y   A   Q   T   Q   L   D   K   T   N   V   F
721/241                                                         751/251                                             781/261
CTG GAG CTG GAT GAT GAG CTC CAC ATC TGG CAC AGT GGA CAG ACT TGG TTG CTG GAG TCT CTG ACA GAC AAA TCT CTT AAG GAG CTG CCG TTA TAC TGT TCT GAG GTT CCC AGT GTT CCC GTG GAA TGG
 L   E   L   D   D   E   L   H   I   W   H   S   G   Q   T   W   L   L   E   S   L   T   D   K   S   L   P   L   Y   C   S   E   V   P   S   V   P   V   E   W
811/271                                                         841/281                                             871/291
AAT GCA ACC TTC CAC ATT AAT GCT GCT GAC CAT GCA ATG GTC GAG AAA GGC ATT GAA GAC AAA TCT CTT AAG GAG CAG CAG TTC AAA GAA GAG GTT GAG AAA GGC GAG ACG CGT CTT
 N   A   T   F   H   I   N   A   A   D   H   A   M   V   E   K   G   I   E   D   K   S   L   K   E   Q   Q   F   K   E   E   V   E   K   G   E   T   R   L
901/301                                                         931/311                                             961/321
AAT GAG ATT AAT GCT TCA GAC CAT GCA ATG GTC GAG AAA GGC AAG ATT GAA GAC AAA TCT CTT AAG GAG CAG CAG TTC AAA GAA GAG GTT GAG AAA GGC GAG ACG CGT
 N   E   I   N   A   A   L   A   N   F   K   N   K   S   L   P   L   I   E   D   K   S   K   E   Q   Q   F   K   E   E   V   E   K   G   E   T   R
991/331                                                         1021/341                                            1051/351
GTT CCT TAC GGA AAC CAT TCA TAT CTG GAG TCT CTG ACA GAC AAA TCT CTT ACC TAT TCC ATC AGT TAT TCC ATC AAA ACC CAG TTT TTC
 V   P   Y   G   N   H   S   Y   L   E   S   L   T   D   K   S   L   T   Y   S   I   S   Y   S   I   K   T   Q   F   F
1081/361                                                        1111/371                                            1141/381
TGG GAC AAC AAG TTT GAC CAT GCA ATG GTC GAG AAA GGC AAG ATT GAA GAC AAA TCT CTT AAG GAG CAG CAG TTC AAA GAA GAG GTT GAG AAA GGC GAG ACG CGT
 W   D   N   K   F   D   H   A   M   V   E   K   G   K   I   E   D   K   S   L   K   E   Q   Q   F   K   E   E   V   E   K   G   E   T   R
1171/391                                                        1201/401                                            1231/411
TGT CTT CCC TAC AGG ATG GAT GTG GAG AAA GCC CTC AAG TTC ATG CTG ACG AAT CTT AAG TGG GGT CTT GCT TGG GTG TCC ATC AAA ACC CAG TTT AAC
 C   L   P   Y   R   M   D   V   E   K   A   L   K   F   M   L   T   N   L   K   W   G   L   A   W   V   S   I   K   T   Q   F   N
1261/421                                                        1291/431                                            1321/441
TCT GAG GAG CAG TGG ACA AAA TTC ATG CTG ACG AAT CTT AAG TGG GGT CTT GCT TGG GTG TCC TCA CAA TTT TAT AAC AAA
 S   E   E   Q   W   T   K   A   K   L   K   F   M   L   T   N   L   K   W   G   L   A   W   V   S   S   Q   F   Y   N   K
1351/451                                                        1381/461
TGA CTT TTT TCC TTA GGG GGA GGT TTG CCT TAA
 *   L   F   S   L   G   G   G   L   P   *
```

FIG. 9C

```
1/1                                                            31/11                                                      61/21
ATG GAA GGG TCT AAG ACG TCC AAC AAC AGC ACC ATG CAG GTG TGC CAG TTC GTG TGC CAG CCC CTG AAA CTG GAC ACG AGT
 M   E   G   S   K   T   S   N   N   S   T   M   Q   V   C   Q   F   V   C   Q   P   L   K   L   D   T   S
91/31                                                         121/41                                                     151/51
TTC AAG ATC CTG GAC CGT GTC ACC ATC CAG GAA CTC ACA GCT CCA TTA CTT ACC ACA GCC CAG GCG AAA CCA GGA GAG ACC CAG GAG GAA
 F   K   I   L   D   R   V   T   I   Q   E   L   T   A   P   L   L   T   T   A   Q   A   K   P   G   E   T   Q   E   E
181/61                                                        211/71                                                     241/81
GAG ACT AAC TCA GGA GAG CCA TTT ATT GAA ACT CCT CGC CAG GAT GGT GTC TCT CGC AGA TTC ATC CCC CCA GCC AGG ATG TCC
 E   T   N   S   G   E   P   F   I   E   T   P   R   Q   D   G   V   S   R   R   F   I   P   P   A   R   M   S
271/91                                                        301/101                                                    331/111
ACA GAA AGT GCC AAC AGC TTC ACT CTG ATT GGG GAG GCA TCT GAT GGC ACC GGC ATG GAG AAC CTC AGC CGA AGA CTG AAG GTC ACT GGG
 T   E   S   A   N   S   F   T   L   I   G   E   A   S   D   G   T   G   M   E   N   L   S   R   R   L   K   V   T   G
361/121                                                       391/131                                                    421/141
GAC CTT TTT GAC ATC ATG TCG GGC ACA GAT GTG CAG CAC CCA GAT CAC TGC ACA GAT ACT CTT TTA GAC CAG CTG GAC ACT
 D   L   F   D   I   M   S   G   T   D   V   Q   H   P   D   H   C   T   D   T   L   L   D   Q   L   D   T
451/151                                                       481/161                                                    511/171
CAG CTC AAC GTC ACT GAA AAT GAG TGT CAG AAC TAC AAA ATC TTG GAG ATC TTA GAG CAA ATG AAT GAG GAT GAC AGT GAA CAG TTA
 Q   L   N   V   T   E   N   E   C   Q   N   Y   K   I   L   E   I   L   E   Q   M   N   E   D   D   S   E   Q   L
541/181                                                       571/191                                                    601/201
CAG ATG GAG CTA AAG GAG CTG GCA CTA GAG GAG AGG CTG ATC CTC TGT GAG GAA TTG GAA GAC GTG GAA AAG AAC CGC AAG ATA GTG GCA GAA
 Q   M   E   L   K   E   L   A   L   E   E   R   L   I   L   C   E   E   L   E   D   V   E   K   N   R   K   I   V   A   E
631/211                                                       661/221                                                    691/231
AAT CTC GAG AAG GTC CAG GCT GAG GCT GAG AGA CTG GAT CAG GAA GCT CAG GAG TAT CAG ACG CAG TAC AGT GAA TTT AAA CGA CAG CAG
 N   L   E   K   V   Q   A   E   A   E   R   L   D   Q   E   A   Q   E   Y   Q   T   Q   Y   S   E   F   K   R   Q   Q
721/241                                                       751/251                                                    781/261
CTG GAG CTG GAT GAT GAG CTG AAG AGT GTT GAA AAC CAG ATG CGT TAT GCC AAT AAC TTC CTG AAG AAA ACC AAC GTC TTT
 L   E   L   D   D   E   L   K   S   V   E   N   Q   M   R   Y   A   N   N   F   L   K   K   T   N   V   F
811/271                                                       841/281                                                    871/291
AAT GCA ACC TTC CAC ATC TGG CAC AGT GGA CAG TTT GGC ACA ATC AAT AAC TTC AGG CTG GGT CGC CTG CCC AGT GTT CCC GTG GAA TGG
 N   A   T   F   H   I   W   H   S   G   Q   F   G   T   I   N   N   F   R   L   G   R   L   P   S   V   P   V   E   W
901/301                                                       931/311                                                    961/321
AAT GAG ATT AAT GCT TGG CAG ACT GTG TTG CTG CTC CTC CAT GCT CTG GCC AAT AAG ATG GGT CTG AAA TTT CAG AGA TAC CGA CTT
 N   E   I   N   A   W   Q   T   V   L   L   L   H   A   L   A   N   K   M   G   L   K   F   Q   R   Y   R   L
991/331                                                       1021/341                                                   1051/351
GTT CCT TAC GGA AAC CAT TCA TAT CTG GAG TCT CTG ACA GAC AAA TCT AAG GAT GAA AGG CAA GAT GGC GGA GAA
 V   P   Y   G   N   H   S   Y   L   E   S   L   T   D   K   S   K   D   E   R   Q   D   G   G   E
1081/361                                                      1111/371                                                   1141/381
CAG TGG CGG CTC CTA TTC CAT CAA CCA GTT TAA CTC TGA GGA GCA GTG GAC AAA AGC TCT CAA GTT CAT GCT GAC TCT TAA GTG
 Q   W   R   L   L   F   H   Q   P   V   *   L   *   G   A   V   D   K   S   S   Q   V   H   A   D   S   *   V
1171/391                                                      1201/401                                                   1231/411
GGG TCT TGC CTG TTG GGT GTC CTC ACA ATT TTA TAA CAA ATG ACT TTT TTC CTT AGG GGG AGG TTT GCC TTA A
 G   S   C   L   G   V   L   T   I   L   *   Q   M   T   F   F   L   R   G   R   F   A   L
```

FIGURE 9D

```
1/1                                       31/11                                  61/21
ATG GAA GGG TCT AAG ACG TCC AAC AAC AGC ACC ATG CAG GTG AGC TTC GTG TGC CAG CGC TGC AGC CAG CCC CTG AAA CTG GAC ACG AGT
 M   E   G   S   K   T   S   N   N   S   T   M   Q   V   S   F   V   C   Q   R   C   S   Q   P   L   K   L   D   T   S
91/31                                     121/41                                 151/51
TTC AAG ATC CTG GAC CGT GTC GAG ATC CAG GAA CTC ACA GCT CCA TTA CTT ACC ACA GCC CAG GCG AAA CCA GAG ACC CAG GAG GAA
 F   K   I   L   D   R   V   E   I   Q   E   L   T   A   P   L   L   T   T   A   Q   A   K   P   E   T   Q   E   E
181/61                                    211/71                                 241/81
GAG ACT AAC TCA GGA GAG GAG CCA TTT ATT GAA ACT CCT CAG CAG GAT GGT GTC TCT CGC AGA TTC ATC CCC CCA GCC AGG ATG TCC
 E   T   N   S   G   E   E   P   F   I   E   T   P   Q   Q   D   G   V   S   R   R   F   I   P   P   A   R   M   S
271/91                                    301/101                               331/111
ACA GAA AGT GCC AAC AGC TTC ACT CTG ATT GGG GAG GCA TCT GAT GGC GGC ACC ATG GAG AAC CTC AGC CGA AGA CTG AAG GTC ACT GGG
 T   E   S   A   N   S   F   T   L   I   G   E   A   S   D   G   G   T   M   E   N   L   S   R   R   L   K   V   T   G
361/121                                   391/131                               421/141
GAC CTT TTT GAC ATC ATG TCG GGC CAG ACA GAT GTG GAT CAC CCA CTC TGT GAG GAA TAC ACA GAT CTT TTA GAC CAG CTG GAC ACT
 D   L   F   D   I   M   S   G   Q   T   D   V   D   H   P   L   C   E   E   Y   T   D   L   L   D   Q   L   D   T
451/151                                   481/161                               511/171
CAG CTC AAC GTC ACT GAA AAT GAG TGT CAG AAC TAC AAA CGC AAG CTC GAG ATC TTA GAG CAA ATG GAT GAC AAG AGT GAA CAG TTA
 Q   L   N   V   T   E   N   E   C   Q   N   Y   K   R   K   L   E   I   L   E   Q   M   N   E   D   D   S   E   Q   L
541/181                                   571/191                               601/201
CAG ATG GAG CTA AAG GAG CTG GCA GCT GAG CTA CAG GAG GAG GAA AGG CTG GAT CAG GAA GCT CAG TAT CAG GTG GAA AAC CCC AAG ATA GTG GCA GAA
 Q   M   E   L   K   E   L   A   A   E   L   Q   E   E   E   R   L   D   Q   E   A   Q   Y   Q   V   E   K   N   R   K   I   V   A   E
631/211                                   661/221                               691/231
AAT CTC GAG AAG GTC CAG GAT GAT GAG CTG AAG AGT GTT GAA AAC CAG ATG CGT TAT GCC CAG ACG CAG AGA GAA TAC AGT AAG CTC AAG TTT AAA CGA CAG CAG
 N   L   E   K   V   Q   D   D   E   L   K   S   V   E   N   Q   M   R   Y   A   Q   T   Q   R   E   Y   S   K   L   K   F   K   R   Q   Q
721/241                                   751/251                               781/261
CTG GAG CTG GAT GAT GAG CTT CAC ATC TGG CAC AGT GGA CAG TTT GGC ACA ATC AAT AAC TTC AGG CTG GGT CGC CTG CCC AGT    CCC GTG GAA TAC
 L   E   L   D   D   E   L   H   I   W   H   S   G   Q   F   G   T   I   N   N   F   R   L   G   R   L   P   S   ?   P   V   E   ?   W
811/271                                   841/281                               871/291
AAT GCA ACC TTC CAC ATC GCT GCT AAT GCT TGG GGC CAG ACT GTG TTG CTG CTC CAT GCT CTT GCC AAT AAG ATG GGT CTG AAA TTT CAG AGA TAC CGA CTT
 N   A   T   F   H   I   A   A   N   A   W   G   Q   T   V   L   L   L   H   A   L   A   N   K   M   G   L   K   F   Q   R   Y   R   L
901/301                                   931/311                               961/321
GTT CCT TAC GGA AAC CAT TCA TAT CTG GAG TCT CTG ACA GAC TCT AAG AAA TCT AAG gct gaa gtg caa gtg cat gat ctc ggc tta ctg caa cct
 V   P   Y   G   N   H   S   Y   L   E   S   L   T   D   S   K   K   A   E   V   Q   W   H   D   L   G   L   L   Q   P
1081/361                                  1111/371                              1141/381
ccg cct ccc ggg ttc aag caa ttc ccc tgc ctc agc ctc ctg agt atc tgg gat tac agg cat gca cca cca cgc ccg gct aat tag GAT
 P   P   P   G   F   K   Q   F   P   C   L   S   L   L   S   I   W   D   Y   R   H   A   P   P   R   P   A   N   *   D
1171/391                                  1201/401                              1231/411
GGA TGT GGA GAA AGG CAA GAT CAT GCT GAC GAA TCT AGA CAC AGG CAG TGG CGG CTC CTA TTC CAT CAA AAC CCA GTT TAA CTC TGA GGA GCA GTG GAC
 G   C   G   E   R   Q   D   H   A   D   E   S   R   H   R   Q   W   R   L   L   F   H   Q   N   P   V   *   L   *   G   A   V   D
1261/421                                  1291/431                              1321/441
AAA AGC TCT CAA GTT CAT GCT GAC GAA TCT TAA GTG GGG TCT TGC CTC CTC ACA ATT TTA TAA CAA ATG ACT TTT TTC CTT AGG
 K   S   S   Q   V   H   A   D   E   S   *   V   G   S   C   L   L   T   I   L   *   Q   M   T   F   F   L   R
1351/451
GGG AGG TTT GCC TTA A
 G   R   F   A   L
```

FIGURE 21A  FIGURE 21B 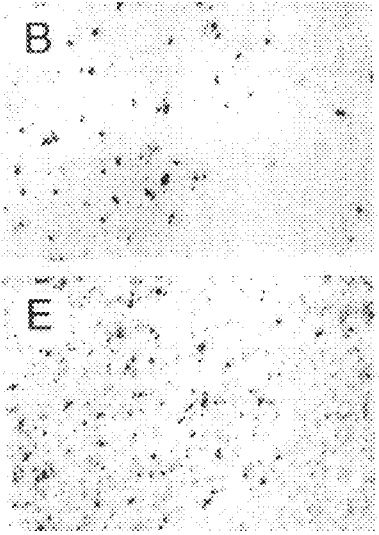 FIGURE 21C 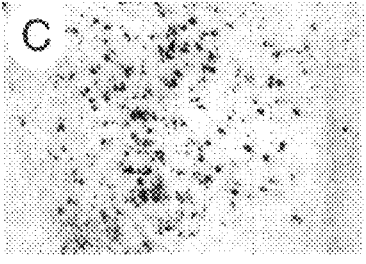
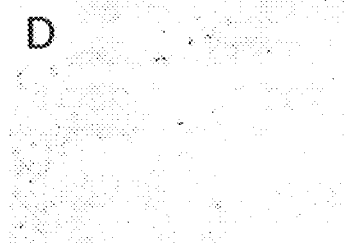 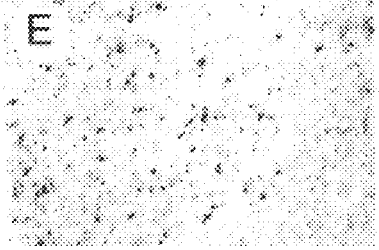 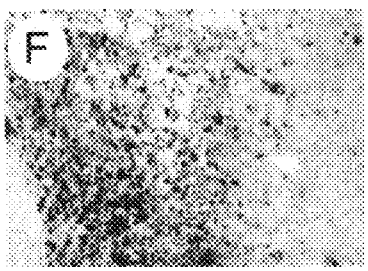
FIGURE 21D  FIGURE 21E  FIGURE 21F FIGURE 23A
FIGURE 23C
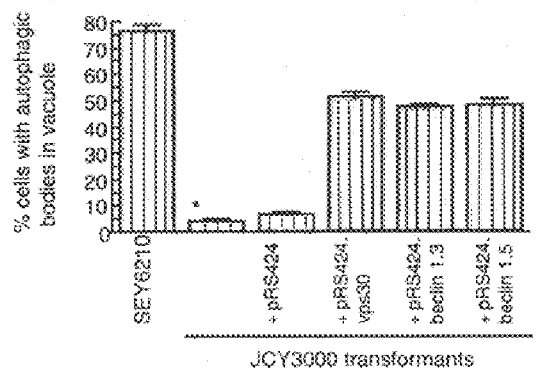
FIGURE 23B
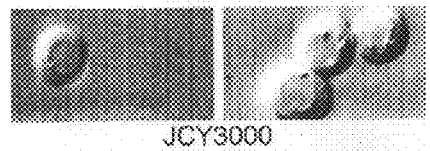

Days after tamoxifen
treatment (10μm)    0    2    3    4
Beclin 1 —  — 60 kD

SEQUENCE LISTING

<160> NUMBER OF SEQ ID NOS: 23

<210> SEQ ID NO 1
<211> LENGTH: 450
<212> TYPE: PRT
<213> ORGANISM: human

<400> SEQUENCE: 1

```
Met Glu Gly Ser Lys Thr Ser Asn Asn Ser Thr Met Gln Val Ser Phe
 1               5                  10                  15

Val Cys Gln Arg Cys Ser Gln Pro Leu Lys Leu Asp Thr Ser Phe Lys
                20                  25                  30

Ile Leu Asp Arg Val Thr Ile Gln Glu Leu Thr Ala Pro Leu Leu Thr
            35                  40                  45

Thr Ala Gln Ala Lys Pro Gly Glu Thr Gln Glu Glu Thr Asn Ser
        50                  55                  60

Gly Glu Glu Pro Phe Ile Glu Thr Pro Arg Gln Asp Gly Val Ser Arg
 65                  70                  75                  80

Arg Phe Ile Pro Pro Ala Arg Met Met Ser Thr Glu Ser Ala Asn Ser
                85                  90                  95

Phe Thr Leu Ile Gly Glu Val Ser Asp Gly Thr Met Glu Asn Leu
            100                 105                 110

Ser Arg Arg Leu Lys Val Thr Gly Asp Leu Phe Asp Ile Met Ser Gly
        115                 120                 125

Gln Thr Asp Val Asp His Pro Leu Cys Glu Glu Cys Thr Asp Thr Leu
130                 135                 140

Leu Asp Gln Leu Asp Thr Gln Leu Asn Val Thr Glu Asn Glu Cys Gln
145                 150                 155                 160

Asn Tyr Lys Arg Cys Leu Glu Ile Leu Glu Gln Met Asn Glu Asp Asp
                165                 170                 175

Ser Glu Gln Leu Gln Met Glu Leu Lys Glu Leu Ala Leu Glu Glu Glu
            180                 185                 190

Arg Leu Ile Gln Glu Leu Glu Asp Val Glu Lys Asn Arg Lys Ile Val
        195                 200                 205

Ala Glu Asn Leu Glu Lys Val Gln Ala Glu Ala Glu Arg Leu Asp Gln
    210                 215                 220

Glu Glu Ala Gln Tyr Gln Arg Glu Tyr Ser Glu Phe Lys Arg Gln Gln
225                 230                 235                 240

Leu Glu Leu Asp Asp Glu Leu Lys Ser Val Glu Asn Gln Met Arg Tyr
                245                 250                 255

Ala Gln Thr Gln Leu Asp Lys Leu Lys Lys Thr Asn Val Phe Asn Ala
            260                 265                 270

Thr Phe His Ile Trp His Ser Gly Gln Phe Gly Thr Ile Asn Asn Phe
        275                 280                 285

Arg Leu Gly Arg Leu Pro Ser Val Pro Val Glu Trp Asn Glu Ile Asn
    290                 295                 300

Ala Ala Trp Gly Gln Thr Val Leu Leu His Ala Leu Ala Asn Lys
305                 310                 315                 320

Met Gly Leu Lys Phe Gln Arg Tyr Arg Leu Val Pro Tyr Gly Asn His
                325                 330                 335

Ser Tyr Leu Glu Ser Leu Thr Asp Lys Ser Lys Glu Leu Pro Leu Tyr
            340                 345                 350

Cys Ser Gly Gly Leu Arg Phe Phe Trp Asp Asn Lys Phe Asp His Ala
```

```
                355                 360                 365
Met Val Ala Phe Leu Asp Cys Val Gln Gln Phe Lys Glu Glu Val Glu
                370                 375                 380

Lys Gly Glu Thr Arg Phe Cys Leu Pro Tyr Arg Met Asp Val Glu Lys
385                 390                 395                 400

Gly Lys Ile Glu Asp Thr Gly Ser Gly Gly Ser Tyr Ser Ile Lys
                405                 410                 415

Thr Gln Phe Asn Ser Glu Glu Gln Trp Thr Lys Ala Leu Lys Phe Met
                420                 425                 430

Leu Thr Asn Leu Lys Trp Gly Leu Ala Trp Val Ser Ser Gln Phe Tyr
                435                 440                 445

Asn Lys
    450

<210> SEQ ID NO 2
<211> LENGTH: 1353
<212> TYPE: DNA
<213> ORGANISM: human

<400> SEQUENCE: 2
atggaagggt ctaagacgtc caacaacagc accatgcagg tgagcttcgt gtgccagcgc      60
tgcagccagc ccctgaaact ggacacgagt ttcaagatcc tggaccgtgt caccatccag     120
gaactcacag ctccattact taccacagcc caggcgaaac caggagagac ccaggaggaa     180
gagactaact caggagagga gccatttatt gaaactcctc gccaggatgg tgtctctcgc     240
agattcatcc ccccagccag gatgatgtcc acagaaagtg ccaacagctt cactctgatt     300
ggggaggtat ctgatggcgg caccatggag aacctcagcc aagactgaa ggtcactggg      360
gaccttttg acatcatgtc gggccagaca gatgtggatc acccactctg tgaggaatgc      420
acagatactc ttttagacca gctggacact cagctcaacg tcactgaaaa tgagtgtcag     480
aactacaaac gctgtttgga gatcttagag caaatgaatg aggatgacag tgaacagtta     540
cagatggagc taaaggagct ggcactagag gaggagaggc tgatccagga gctggaagac     600
gtggaaaaga accgcaagat agtggcagaa atctcgaga aggtccaggc tgaggctgag      660
agactggatc aggaggaagc tcagtatcag agagaataca gtgaatttaa acgacagcag     720
ctggagctgg atgatgagct gaagagtgtt gaaaaccaga tgcgttatgc ccagacgcag     780
ctggataagc tgaagaaaac caacgtcttt aatgcaacct tccacatctg cacagtgga     840
cagtttggca caatcaataa cttcaggctg gtcgcctgc ccagtgttcc cgtggaatgg      900
aatgagatta tgctgcttg gggccagact gtgttgctgc tccatgctct ggccaataag     960
atgggtctga atttcagag ataccgactt gttccttacg aaaccattc atatctggag     1020
tctctgacag acaaatctaa ggagctgccg ttatactgtt ctggggggtt gcggttttc     1080
tgggacaaca gtttgacca tgcaatggtg gctttcctgg actgtgtgca gcagttcaaa     1140
gaagaggttg agaaggcga gacacgtttt tgtcttccct acaggatgga tgtggagaaa     1200
ggcaagattg aagacacagg aggcagtggc ggctcctatt ccatcaaaac ccagtttaac     1260
tctgaggagc agtggacaaa agctctcaag ttcatgctga cgaatcttaa gtggggtctt     1320
gcttgggtgt cctcacaatt ttataacaaa tga                                  1353

<210> SEQ ID NO 3
<211> LENGTH: 120
<212> TYPE: DNA
<213> ORGANISM: human
```

<400> SEQUENCE: 3

```
cgggaagtcg ctgaagacag agcgatggta gttctggagg cctcgctccg gggccgaccc    60
gaggccacag tgcctccgcg gtagaccgga cttgggtgac gggctccggg ctcccgaggg   120
```

<210> SEQ ID NO 4
<211> LENGTH: 654
<212> TYPE: DNA
<213> ORGANISM: human

<400> SEQUENCE: 4

```
ctttttcct taggggagg tttgccttaa aggctttta attttgtttt gtttgcaaac      60
atgttttaaa ttaaattcgg gtaatattaa acagtacatg tttacaatac caaaaagaa   120
aaatccaca aaagccactt tattttaaaa tatcatgtga cagatacttt ccagagctac   180
aacatgccat ctatagttgc cagccctggt cagttttgat tcttaacccc atggactcct   240
ttccctttct tctctgaaaa aaactaattt aaatttgctt ttcttttttt taactgagtt   300
gaattgagat tgatgtgttt tcactggatt tttatctctc tcaacttcct gcacttaaca   360
atatgaaata gaaacttttg tctttactga gatgaggata tgtttgagat gcacagttgg   420
ataatgtggg aaaatgacat ctaagcttta cctggtcacc atgtgatgtg atcagatgct   480
tgaaatttaa acttttcac ttggttctta tactgaatgc cgactctgct ctgtgttaga    540
gatatgaaat ggtgtttgat actgtttgag acattatgga gagatttaat tatttgtaat   600
aaagatttg ctgcagtctg aaaaccggaa aaaaaaaaa aaaaaaaaa aaaa            654
```

<210> SEQ ID NO 5
<211> LENGTH: 1383
<212> TYPE: DNA
<213> ORGANISM: human

<400> SEQUENCE: 5

```
atggaagggt ctaagacgtc caacaacagc accatgcagg tgagcttcgt gtgccagcgc    60
tgcagccagc ccctgaaact ggacacgagt ttcaagatcc tggaccgtgt caccatccag   120
gaactcacag ctccattact taccacagcc caggcgaaac caggagagac ccaggaggaa   180
gagactaact caggagagga gccatttatt gaaactcctc gccaggatgg tgtctctcgc   240
agattcatcc ccccagccag gatgatgtcc acagaaagtg ccaacagctt cactctgatt   300
ggggaggcat ctgatggcgg caccatggag aacctcagcc gaagactgaa ggtcactggg   360
gacctttttg acatcatgtc gggccagaca gatgtggatc acccactctg tgaggaatgc   420
acagatactc ttttagacca gctggacact cagctcaacg tcactgaaaa tgagtgtcag   480
aactacaaac gctgtttgga gatcttagag caaatgaatg aggatgacag tgaacagtta   540
cagatggagc taaaggagct ggcactagag gaggagaggc tgatccagga gctggaagac   600
gtggaaaaga ccgcaagat agtggcagaa aatctcgaga aggtccaggc tgaggctgag   660
agactggatc aggaggaagc tcagtatcag agagaataca gtgaatttaa acgacagcag   720
ctggagctgg atgatgagct gaagagtgtt gaaaaccaga tgcgttatgc ccagacgcag   780
ctggataagc tgaagaaaac caacgtcttt aatgcaacct tccacatctg gcacagtgga   840
cagtttggca caatcaataa cttcaggctg gtcgcctgc ccagtgttcc cgtggaatgg   900
aatgagatta tgctgcttg gggccagact gtgttgctgc tccatgctct ggccaataag   960
atgggtctga atttcagag ataccgactt gttccttacg gaaaccattc atatctggag  1020
```

-continued

```
tctctgacag acaaatctaa ggagctgccg ttatactgtt ctgggggtt gcggttttc    1080 tgggacaaca agtttgacca tgcaatggtg gctttcctgg actgtgtgca gcagttcaaa    1140
gaagaggttg agaaggcga gacacgtttt tgtcttccct acaggatgga tgtggagaaa    1200
ggcaagattg aagacacagg aggcagtggc ggctcctatt ccatcaaaac ccagtttaac    1260
tctgaggagc agtggacaaa agctctcaag ttcatgctga cgaatcttaa gtggggtctt    1320
gcttgggtgt cctcacaatt ttataacaaa tgacttttt ccttaggggg aggtttgcct    1380
taa                                                                  1383
```

```
<210> SEQ ID NO 6
<211> LENGTH: 450
<212> TYPE: PRT
<213> ORGANISM: human

<400> SEQUENCE: 6
```

```
Met Glu Gly Ser Lys Thr Ser Asn Asn Ser Thr Met Gln Val Ser Phe
  1               5                  10                  15

Val Cys Gln Arg Cys Ser Gln Pro Leu Lys Leu Asp Thr Ser Phe Lys
                 20                  25                  30

Ile Leu Asp Arg Val Thr Ile Gln Glu Leu Thr Ala Pro Leu Leu Thr
             35                  40                  45

Thr Ala Gln Ala Lys Pro Gly Glu Thr Gln Glu Glu Thr Asn Ser
         50                  55                  60

Gly Glu Glu Pro Phe Ile Glu Thr Pro Arg Gln Asp Gly Val Ser Arg
 65                  70                  75                  80

Arg Phe Ile Pro Pro Ala Arg Met Met Ser Thr Glu Ser Ala Asn Ser
                 85                  90                  95

Phe Thr Leu Ile Gly Glu Ala Ser Asp Gly Gly Thr Met Glu Asn Leu
                100                 105                 110

Ser Arg Arg Leu Lys Val Thr Gly Asp Leu Phe Asp Ile Met Ser Gly
            115                 120                 125

Gln Thr Asp Val Asp His Pro Leu Cys Glu Glu Cys Thr Asp Thr Leu
        130                 135                 140

Leu Asp Gln Leu Asp Thr Gln Leu Asn Val Thr Glu Asn Glu Cys Gln
145                 150                 155                 160

Asn Tyr Lys Arg Cys Leu Glu Ile Leu Glu Gln Met Asn Glu Asp Asp
                165                 170                 175

Ser Glu Gln Leu Gln Met Glu Leu Lys Glu Leu Ala Leu Glu Glu
            180                 185                 190

Arg Leu Ile Gln Glu Leu Glu Asp Val Glu Lys Asn Arg Lys Ile Val
        195                 200                 205

Ala Glu Asn Leu Glu Lys Val Gln Ala Glu Ala Glu Arg Leu Asp Gln
    210                 215                 220

Glu Glu Ala Gln Tyr Gln Arg Glu Tyr Ser Glu Phe Lys Arg Gln Gln
225                 230                 235                 240

Leu Glu Leu Asp Asp Glu Leu Lys Ser Val Glu Asn Gln Met Arg Tyr
                245                 250                 255

Ala Gln Thr Gln Leu Asp Lys Leu Lys Lys Thr Asn Val Phe Asn Ala
            260                 265                 270

Thr Phe His Ile Trp His Ser Gly Gln Phe Gly Thr Ile Asn Asn Phe
        275                 280                 285

Arg Leu Gly Arg Leu Pro Ser Val Pro Val Glu Trp Asn Glu Ile Asn
    290                 295                 300
```

```
Ala Ala Trp Gly Gln Thr Val Leu Leu Leu His Ala Leu Ala Asn Lys
305                 310                 315                 320

Met Gly Leu Lys Phe Gln Arg Tyr Arg Leu Val Pro Tyr Gly Asn His
            325                 330                 335

Ser Tyr Leu Glu Ser Leu Thr Asp Lys Ser Lys Glu Leu Pro Leu Tyr
            340                 345                 350

Cys Ser Gly Gly Leu Arg Phe Phe Trp Asp Asn Lys Phe Asp His Ala
            355                 360                 365

Met Val Ala Phe Leu Asp Cys Val Gln Gln Phe Lys Glu Glu Val Glu
370                 375                 380

Lys Gly Glu Thr Arg Phe Cys Leu Pro Tyr Arg Met Asp Val Glu Lys
385                 390                 395                 400

Gly Lys Ile Glu Asp Thr Gly Gly Ser Gly Gly Ser Tyr Ser Ile Lys
            405                 410                 415

Thr Gln Phe Asn Ser Glu Glu Gln Trp Thr Lys Ala Leu Lys Phe Met
            420                 425                 430

Leu Thr Asn Leu Lys Trp Gly Leu Ala Trp Val Ser Ser Gln Phe Tyr
            435                 440                 445

Asn Lys
450

<210> SEQ ID NO 7
<211> LENGTH: 9
<212> TYPE: PRT
<213> ORGANISM: human

<400> SEQUENCE: 7

Leu Phe Ser Leu Gly Gly Gly Leu Pro
  1               5

<210> SEQ ID NO 8
<211> LENGTH: 1240
<212> TYPE: DNA
<213> ORGANISM: human

<400> SEQUENCE: 8 atggaaggt ctaagacgtc caacaacagc accatgcagg tgagcttcgt gtgccagcgc      60
tgcagccagc ccctgaaact ggacacgagt ttcaagatcc tggaccgtgt caccatccag    120
gaactcacag ctccattact taccacagcc caggcgaaac caggagagac ccaggaggaa    180
gagactaact caggagagga gccatttatt gaaactcctc gccaggatgg tgtctctcgc    240
agattcatcc ccccagccag gatgatgtcc acagaaagtg ccaacagctt cactctgatt    300
ggggaggcat ctgatggcgg caccatcgag aacctcagcc gaagactgaa ggtcactggg    360
gacctttttg acatcatgtc gggccagaca gatgtggatc ccccactctg tgaggaatgc    420
acagatactc ttttagacca gctggacact cagctcaacg tcactgaaaa tgagtgtcag    480
aactacaaac gctgtttgga gatcttagag caaatgaatg aggatgacag tgaacagtta    540
cagatggagc taaggagct ggcactagag gaggagaggc tgatccagga gctggaagac    600
gtggaaaaga accgcaagat agtggcagaa atctcgaga aggtccaggc tgaggctgag    660
agactggatc aggaggaagc tcagtatcag agagaataca gtgaatttaa acgacagcag    720
ctggagctgg atgatgagct gaagagtgtt gaaaaccaga tgcgttatgc ccagacgcag    780
ctggataagc tgaagaaaac caacgtcttt aatgcaacct tccacatctg cacagtggaa    840
cagtttggca caatcaataa cttcaggctg ggtcgcctgc ccagtgttcc cgtggaatgg    900
```

```
aatgagatta atgctgcttg gggccagact gtgttgctgc tccatgctct ggccaataag    960
atgggtctga aatttcagag ataccgactt gttccttacg gaaaccattc atatctggag   1020
tctctgacag acaaatctaa ggatggatgt ggagaaaggc aagattgaag acacaggagg   1080
cagtggcggc tcctattcca tcaaaaccca gtttaactct gaggagcagt ggacaaaagc   1140
tctcaagttc atgctgacga atcttaagtg gggtcttgct tgggtgtcct cacaatttta   1200
taacaaatga cttttttcct tagggggagg tttgccttaa                         1240
```

<210> SEQ ID NO 9
<211> LENGTH: 355
<212> TYPE: PRT
<213> ORGANISM: human

<400> SEQUENCE: 9

```
Met Glu Gly Ser Lys Thr Ser Asn Asn Ser Thr Met Gln Val Ser Phe
 1               5                  10                  15

Val Cys Gln Arg Cys Ser Gln Pro Leu Lys Leu Asp Thr Ser Phe Lys
                20                  25                  30

Ile Leu Asp Arg Val Thr Ile Gln Glu Leu Thr Ala Pro Leu Leu Thr
            35                  40                  45

Thr Ala Gln Ala Lys Pro Gly Glu Thr Gln Glu Glu Thr Asn Ser
        50                  55                  60

Gly Glu Glu Pro Phe Ile Glu Thr Pro Arg Gln Asp Gly Val Ser Arg
 65                  70                  75                  80

Arg Phe Ile Pro Pro Ala Arg Met Met Ser Thr Glu Ser Ala Asn Ser
                85                  90                  95

Phe Thr Leu Ile Gly Glu Ala Ser Asp Gly Gly Thr Ile Glu Asn Leu
            100                 105                 110

Ser Arg Arg Leu Lys Val Thr Gly Asp Leu Phe Asp Ile Met Ser Gly
        115                 120                 125

Gln Thr Asp Val Asp His Pro Leu Cys Glu Glu Cys Thr Asp Thr Leu
    130                 135                 140

Leu Asp Gln Leu Asp Thr Gln Leu Asn Val Thr Glu Asn Glu Cys Gln
145                 150                 155                 160

Asn Tyr Lys Arg Cys Leu Glu Ile Leu Glu Gln Met Asn Glu Asp Asp
                165                 170                 175

Ser Glu Gln Leu Gln Met Glu Leu Lys Glu Leu Ala Leu Glu Glu
            180                 185                 190

Arg Leu Ile Gln Glu Leu Glu Asp Val Glu Lys Asn Arg Lys Ile Val
        195                 200                 205

Ala Glu Asn Leu Glu Lys Val Gln Ala Glu Ala Glu Arg Leu Asp Gln
    210                 215                 220

Glu Glu Ala Gln Tyr Gln Arg Glu Tyr Ser Glu Phe Lys Arg Gln Gln
225                 230                 235                 240

Leu Glu Leu Asp Asp Glu Leu Lys Ser Val Glu Asn Gln Met Arg Tyr
                245                 250                 255

Ala Gln Thr Gln Leu Asp Lys Leu Lys Lys Thr Asn Val Phe Asn Ala
            260                 265                 270

Thr Phe His Ile Trp His Ser Gly Gln Phe Gly Thr Ile Asn Asn Phe
        275                 280                 285

Arg Leu Gly Arg Leu Pro Ser Val Pro Val Glu Trp Asn Glu Ile Asn
    290                 295                 300

Ala Ala Trp Gly Gln Thr Val Leu Leu Leu His Ala Leu Ala Asn Lys
305                 310                 315                 320
```

```
                Met Gly Leu Lys Phe Gln Arg Tyr Arg Leu Val Pro Tyr Gly Asn His
                                325                 330                 335

Ser Tyr Leu Glu Ser Leu Thr Asp Lys Ser Lys Asp Gly Cys Gly Glu
                            340                 345                 350

Arg Gln Asp
                        355

<210> SEQ ID NO 10
<211> LENGTH: 1366
<212> TYPE: DNA
<213> ORGANISM: human

<400> SEQUENCE: 10
atggaagggt ctaagacgtc caacaacagc accatgcagg tgagcttcgt gtgccagcgc        60
tgcagccagc ccctgaaact ggacacgagt ttcaagatcc tggaccgtgt caccatccag       120
gaactcacag ctccattact taccacagcc caggcgaaac caggagagac ccaggaggaa       180
gagactaact caggagagga gccatttatt gaaactcctc gccaggatgg tgtctctcgc       240
agattcatcc ccccagccag gatgatgtcc acagaaagtg ccaacagctt cactctgatt       300
ggggaggcat ctgatggcgg caccatggag aacctcagcc aagactgaa ggtcactggg        360 gacctttttg acatcatgtc gggccagaca gatgtggatc acccactctg tgaggaatgc       420
acagatactc ttttagacca gctggacact cagctcaacg tcactgaaaa tgagtgtcag       480
aactacaaac gctgtttgga gatcttagag caaatgaatg aggatgacag tgaacagtta       540
cagatggagc taaaggagct ggcactagag gaggagaggc tgatccagga gctggaagac       600
gtggaaaaga accgcaagat agtggcagaa atctcgaga aggtccaggc tgaggctgag         660
agactggatc aggaggaagc tcagtatcag agagaataca gtgaatttaa acgacagcag       720
ctggagctgg atgatgagct gaagagtgtt gaaaaccaga tgcgttatgc ccagacgcag       780
ctggataagc tgaagaaaac caacgtcttt aatgcaacct tccacatctg cacagtgga        840 cagtttggca caatcaataa cttcaggctg gtcgcctgc ccagtgttcc cgtggaatgg        900
aatgagatta tgctgcttg gggccagact gtgttgctgc tccatgctct ggccaataag        960
atgggtctga aatttcagag ataccgactt gttccttacg gaaaccattc atatctggaa      1020
tctctgacag acaaatctaa ggctgaagtg caatggcatg atctcggctt actgcaacct      1080
ccgcctcccg ggttcaagca attccccttgc ctcagcctcc tgagtatctg ggattacagg     1140
catgcaccac cacgcccggc taattaggat ggatgtggag aaaggcaaga ttgaagacac       1200
aggaggcagt ggcggctcct attccatcaa aacccagttt aactctgagg agcagtggac      1260
aaaagctctc aagttcatgc tgacgaatct taagtggggt cttgcttggg tgtcctcaca      1320
attttataac aaatgacttt tttccttagg gggaggtttg ccttaa                     1366

<210> SEQ ID NO 11
<211> LENGTH: 388
<212> TYPE: PRT
<213> ORGANISM: human

<400> SEQUENCE: 11

Met Glu Gly Ser Lys Thr Ser Asn Asn Ser Thr Met Gln Val Ser Phe
  1               5                  10                  15

Val Cys Gln Arg Cys Ser Gln Pro Leu Lys Leu Asp Thr Ser Phe Lys
                 20                  25                  30

Ile Leu Asp Arg Val Thr Ile Gln Glu Leu Thr Ala Pro Leu Leu Thr
```

```
              35                  40                  45
Thr Ala Gln Ala Lys Pro Gly Glu Thr Gln Glu Glu Thr Asn Ser
        50                  55                  60
Gly Glu Glu Pro Phe Ile Glu Thr Pro Arg Gln Asp Gly Val Ser Arg
 65                  70                  75                  80
Arg Phe Ile Pro Pro Ala Arg Met Met Ser Thr Glu Ser Ala Asn Ser
                 85                  90                  95
Phe Thr Leu Ile Gly Glu Ala Ser Asp Gly Thr Met Glu Asn Leu
                100                 105                 110
Ser Arg Arg Leu Lys Val Thr Gly Asp Leu Phe Asp Ile Met Ser Gly
            115                 120                 125
Gln Thr Asp Val Asp His Pro Leu Cys Glu Glu Cys Thr Asp Thr Leu
            130                 135                 140
Leu Asp Gln Leu Asp Thr Gln Leu Asn Val Thr Glu Asn Glu Cys Gln
145                 150                 155                 160
Asn Tyr Lys Arg Cys Leu Glu Ile Leu Glu Gln Met Asn Glu Asp Asp
                165                 170                 175
Ser Glu Gln Leu Gln Met Glu Leu Lys Glu Leu Ala Leu Glu Glu
            180                 185                 190
Arg Leu Ile Gln Glu Leu Glu Asp Val Glu Lys Asn Arg Lys Ile Val
            195                 200                 205
Ala Glu Asn Leu Glu Lys Val Gln Ala Glu Ala Glu Arg Leu Asp Gln
210                 215                 220
Glu Glu Ala Gln Tyr Gln Arg Glu Tyr Ser Glu Phe Lys Arg Gln Gln
225                 230                 235                 240
Leu Glu Leu Asp Asp Glu Leu Lys Ser Val Glu Asn Gln Met Arg Tyr
                245                 250                 255
Ala Gln Thr Gln Leu Asp Lys Leu Lys Lys Thr Asn Val Phe Asn Ala
            260                 265                 270
Thr Phe His Ile Trp His Ser Gly Gln Phe Gly Thr Ile Asn Asn Phe
            275                 280                 285
Arg Leu Gly Arg Leu Pro Ser Val Pro Val Glu Trp Asn Glu Ile Asn
            290                 295                 300
Ala Ala Trp Gly Gln Thr Val Leu Leu Leu His Ala Leu Ala Asn Lys
305                 310                 315                 320
Met Gly Leu Lys Phe Gln Arg Tyr Arg Leu Val Pro Tyr Gly Asn His
                325                 330                 335
Ser Tyr Leu Glu Ser Leu Thr Asp Lys Ser Lys Ala Glu Val Gln Trp
            340                 345                 350
His Asp Leu Gly Leu Leu Gln Pro Pro Pro Gly Phe Lys Gln Phe
            355                 360                 365
Pro Cys Leu Ser Leu Leu Ser Ile Trp Asp Tyr Arg His Ala Pro Pro
370                 375                 380
Arg Pro Ala Asn
385

<210> SEQ ID NO 12
<211> LENGTH: 1509
<212> TYPE: DNA
<213> ORGANISM: human

<400> SEQUENCE: 12
atggaagggt ctaagacgtc caacaacagc accatgcagg tgagcttcgt gtgccagcgc      60
tgcagccagc ccctgaaact ggacacgagt ttcaagatcc tggaccgtgt caccatccag     120
```

-continued

```
gaactcacag ctccattact taccacagcc caggcgaaac caggagagac ccaggaggaa    180
gagactaact caggagagga gccatttatt gaaactcctc gccaggatgg tgtctctcgc    240
agattcatcc ccccagccag gatgatgtcc acagaaagtg ccaacagctt cactctgatt    300
ggggaggcat ctgatggcgg caccatggag aacctcagcc gaagactgaa ggtcactggg    360
gacctttttg acatcatgtc gggccagaca gatgtggatc acccactctg tgaggaatgc    420
acagatactc ttttagacca gctggacact cagctcaacg tcactgaaaa tgagtgtcag    480
aactacaaac gctgtttgga gatcttagag caaatgaatg aggatgacag tgaacagtta    540
cagatggagc taaaggagct ggcactagag gaggagaggc tgatccagga gctggaagac    600
gtggaaaaga accgcaagat agtggcagaa atctcgaga aggtccaggc tgaggctgag    660
agactggatc agcaggaagc tcagtatcag agagaataca gtgaatttaa acgacagcag    720
ctggagctgg atgatgagct gaagagtgtt gaaaaccaga tgcgttatgc ccagacgcag    780
ctggataagc tgaagaaaac caacgtcttt aatgcaacct ccacatctg gcacagtgga    840
cagtttggca caatcaataa cttcaggctg gtcgcctgc ccagtgttcc cgtgaatgg    900
aatgagatta atgctgcttg gggccagact gtgttgctgc tccatgctct ggccaataag    960
atgggtctga aatttcagag ataccgactt gttccttacg gaaaccattc atatctggag   1020
tctctgacag acaaatctaa ggagctgccg ttatactgtt ctgggggggtt gcggttttc   1080
tgggacaaca aggctgaagt gcaatggcat gatctcggct tactgcaacc tccgcctccc   1140
gggttcaagc aattcccctg cctcagcctc ctgagtatct gggattacag gcatgcacca   1200
ccacgcccgg ctaattagtt tgaccatgca atggtggctt tcctgactg tgtgcagcag   1260
ttcaaagaag aggttgagaa aggcgagaca cgttttttgtc ttccctacag gatggatgtg   1320
gagaaaggca agattgaaga cacaggaggc agtggcggct cctattccat caaaacccag   1380
tttaactctg aggagcagtg gacaaaagct ctcaagttca tgctgacgaa tcttaagtgg   1440
ggtcttgctt gggtgtcctc acaattttat aacaaatgac tttttttcctt agggggaggt   1500
ttgccttaa                                                           1509
```

<210> SEQ ID NO 13
<211> LENGTH: 500
<212> TYPE: PRT
<213> ORGANISM: human

<400> SEQUENCE: 13

```
Met Glu Gly Ser Lys Thr Ser Asn Asn Ser Thr Met Gln Val Ser Phe
  1               5                  10                  15

Val Cys Gln Arg Cys Ser Gln Pro Leu Lys Leu Asp Thr Ser Phe Lys
                 20                  25                  30

Ile Leu Asp Arg Val Thr Ile Gln Glu Leu Thr Ala Pro Leu Leu Thr
             35                  40                  45

Thr Ala Gln Ala Lys Pro Gly Glu Thr Gln Glu Glu Thr Asn Ser
         50                  55                  60

Gly Glu Glu Pro Phe Ile Glu Thr Pro Arg Gln Asp Gly Val Ser Arg
 65                  70                  75                  80

Arg Phe Ile Pro Pro Ala Arg Met Met Ser Thr Glu Ser Ala Asn Ser
                 85                  90                  95

Phe Thr Leu Ile Gly Glu Ala Ser Asp Gly Gly Thr Met Glu Asn Leu
                100                 105                 110

Ser Arg Arg Leu Lys Val Thr Gly Asp Leu Phe Asp Ile Met Ser Gly
```

```
            115                 120                 125
Gln Thr Asp Val Asp His Pro Leu Cys Glu Glu Cys Thr Asp Thr Leu
            130                 135                 140

Leu Asp Gln Leu Asp Thr Gln Leu Asn Val Thr Glu Asn Glu Cys Gln
145                 150                 155                 160

Asn Tyr Lys Arg Cys Leu Glu Ile Leu Glu Gln Met Asn Glu Asp Asp
                165                 170                 175

Ser Glu Gln Leu Gln Met Glu Leu Lys Glu Leu Ala Leu Glu Glu Glu
                180                 185                 190

Arg Leu Ile Gln Glu Leu Glu Asp Val Glu Lys Asn Arg Lys Ile Val
                195                 200                 205

Ala Glu Asn Leu Glu Lys Val Gln Ala Glu Ala Glu Arg Leu Asp Gln
210                 215                 220

Gln Glu Ala Gln Tyr Gln Arg Glu Tyr Ser Glu Phe Lys Arg Gln Gln
225                 230                 235                 240

Leu Glu Leu Asp Asp Glu Leu Lys Ser Val Glu Asn Gln Met Arg Tyr
                245                 250                 255

Ala Gln Thr Gln Leu Asp Lys Leu Lys Lys Thr Asn Val Phe Asn Ala
                260                 265                 270

Thr Phe His Ile Trp His Ser Gly Gln Phe Gly Thr Ile Asn Asn Phe
                275                 280                 285

Arg Leu Gly Arg Leu Pro Ser Val Pro Val Glu Trp Asn Glu Ile Asn
290                 295                 300

Ala Ala Trp Gly Gln Thr Val Leu Leu Leu His Ala Leu Ala Asn Lys
305                 310                 315                 320

Met Gly Leu Lys Phe Gln Arg Tyr Arg Leu Val Pro Tyr Gly Asn His
                325                 330                 335

Ser Tyr Leu Glu Ser Leu Thr Asp Lys Ser Lys Glu Leu Pro Leu Tyr
                340                 345                 350

Cys Ser Gly Gly Leu Arg Phe Phe Trp Asp Asn Lys Ala Glu Val Gln
                355                 360                 365

Trp His Asp Leu Gly Leu Leu Gln Pro Pro Pro Gly Phe Lys Gln
                370                 375                 380

Phe Pro Cys Leu Ser Leu Leu Ser Ile Trp Asp Tyr Arg His Ala Pro
385                 390                 395                 400

Pro Arg Pro Ala Asn Phe Asp His Ala Met Val Ala Phe Leu Asp Cys
                405                 410                 415

Val Gln Gln Phe Lys Glu Glu Val Glu Lys Gly Glu Thr Arg Phe Cys
                420                 425                 430

Leu Pro Tyr Arg Met Asp Val Glu Lys Gly Lys Ile Glu Asp Thr Gly
                435                 440                 445

Gly Ser Gly Gly Ser Tyr Ser Ile Lys Thr Gln Phe Asn Ser Glu Glu
450                 455                 460

Gln Trp Thr Lys Ala Leu Lys Phe Met Leu Thr Asn Leu Lys Trp Gly
465                 470                 475                 480

Leu Ala Trp Val Ser Ser Gln Phe Tyr Asn Lys Leu Phe Ser Leu Gly
                485                 490                 495

Gly Gly Leu Pro
            500

<210> SEQ ID NO 14
<211> LENGTH: 20
<212> TYPE: DNA
<213> ORGANISM: Artificial Sequence
```

```
<220> FEATURE:
<223> OTHER INFORMATION: Description of Artificial Sequence: nucleic
      acid

<400> SEQUENCE: 14
ccgacttgtt ccttacggaa                                                      20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: nucleic
      acid

<400> SEQUENCE: 15
cgtgtctcgc ctttctcaac                                                      20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: nucleic
      acid

<400> SEQUENCE: 16
tgcggttttt ctgggacaac                                                      20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: nucleic
      acid

<400> SEQUENCE: 17
caagcaagac cccacttaag                                                      20

<210> SEQ ID NO 18
<211> LENGTH: 14
<212> TYPE: PRT
<213> ORGANISM: human

<400> SEQUENCE: 18

Met Glu Gly Ser Lys Thr Ser Asn Asn Ser Thr Met Gln Val
 1               5                  10

<210> SEQ ID NO 19
<211> LENGTH: 16
<212> TYPE: PRT
<213> ORGANISM: human

<400> SEQUENCE: 19

Cys Val Gln Gln Phe Lys Glu Glu Val Glu Lys Gly Glu Thr Arg Phe
 1               5                  10                  15

<210> SEQ ID NO 20
<211> LENGTH: 20
<212> TYPE: PRT
<213> ORGANISM: human

<400> SEQUENCE: 20

Glu Leu Phe Arg Asp Gly Val Asn Trp Gly Arg Ile Val Ala Phe Phe
 1               5                  10                  15
```

```
Glu Phe Gly Gly
            20

<210> SEQ ID NO 21
<211> LENGTH: 20
<212> TYPE: PRT
<213> ORGANISM: human

<400> SEQUENCE: 21

Glu Leu Phe Arg Asp Gly Val Asn Trp Gly Arg Ile Val Ala Phe Phe
  1               5                  10                  15

Ser Phe Gly Gly
            20

<210> SEQ ID NO 22
<211> LENGTH: 20
<212> TYPE: PRT
<213> ORGANISM: human

<400> SEQUENCE: 22

Glu Leu Phe Arg Asp Gly Val Asn Trp Ala Arg Ile Val Ala Phe Phe
  1               5                  10                  15

Glu Phe Gly Gly
            20

<210> SEQ ID NO 23
<211> LENGTH: 20
<212> TYPE: PRT
<213> ORGANISM: human

<400> SEQUENCE: 23

Glu Leu Phe Arg Asp Gly Ala Ile Leu Gly Arg Ile Val Ala Phe Phe
  1               5                  10                  15

Ser Phe Gly Gly
            20
```

BECLIN AND USES THEREOF

This application is a continuation-in-part of U.S. Ser. No. 09/250,045, filed Feb. 12, 1999, now abandoned, which is a continuation-in-part of U.S. Ser. No. 09/040,808, filed Mar. 18, 1998, now abandoned, which is a continuation-in-part of International Application No. PCT/US97/16358, filed Sep. 12, 1997, now abandoned, which is a continuation-in-part of U.S. Ser. No. 08/712,939 filed Sep. 13, 1996, now U.S. Pat. No. 5,858,669, issued on Jan. 12, 1999. The content of the preceeding applications are hereby incorporated into this application by reference.

The invention disclosed herein was made with Government support under Grant Nos. K08AI01217-01 and R29AI40246 from the National Institutes Of Health of the United States Department of Health and Human Services. Accordingly, the U.S. Government has certain rights in this invention.

Throughout this application, various publications are referenced by author and date. Full citations for these publications may be found listed alphabetically near the end of the specification. The disclosures of these publications in their entireties are hereby incorporated by reference into this application in order to more fully describe the state of the art as known to those skilled therein as of the date of the invention described and claimed herein.

BACKGROUND

Beclin is a novel, 61 kd, Bcl-2-interacting, coiled coiled protein encoded by a gene located on a tumor susceptibility locus on chromosome 17q21. This application shows that Beclin has tumor suppressor and anti-apoptotic functions. The region of chromosome 17q21 encoding Beclin is deleted in 50–75% of cases of prostate cancer, ovarian cancer, and breast cancer.

This application shows that beclin is a tumor suppressor gene important for breast, ovarian, and prostate cancer. The experiments herein show the presence of aberrant splice products in sporadic epithelial ovarian cancers that contain monoallelic deletions of beclin, and the loss of Beclin protein expression in sporadic invasive breast carcinomas. These findings suggest that mutations in beclin splice site junctions, mutations in regulatory regions of the beclin gene (e.g. promoters, enhancers, 5' and 3' nontranslated regions), mutations in the coding region which may lead to decreased protein stability, and/or hypermethylation of the promoter region, are important mechanisms for functional inactivation of beclin and subsequent tumorigenesis in breast, ovarian, and/or prostate cancer.

Monoallelic deletions of chromosome 17q21, detected by loss-of heterozygosity (LOH), are found in 50% of breast carcinomas, 50–75% of ovarian carcinomas, and 40% of prostate carcinomas (Cropp et al. 1993; Futreal et al. 1992; Saito et al. 1993; Eccles et al 1992; Russell et al. 1990; Sato et al. 1991; Yang-Feng et al. 1993; Gao et al. 1995; Gao et al. 1995). This frequent LOH in chromosome 17q21. suggests that inactivation of one or more tumor suppressor genes located on this chromosomal arm are important for breast ovarian, and prostate carcinogenesis. In 1994, the existence of one such gene, BRCA1, was identified by positional cloning, and mutations in BRCA1 are now accepted to be an important cause of hereditary breast and ovarian cancer (Futreal et al. 1994; Miki et al. 1994). However, it remains unclear whether functional inactivation of BRCA1 represents an important molecular event in the development of sporadic breast and ovarian carcinomas. (Vogelstein and Kinzler 1994; Tangir et al. 1994). To fulfill the Knudson two-hit hypothesis (Knudson 1985) for inactivation of a tumor suppressor gene as a mechanism for oncogenesis, a mutation has to be found in the remaining allele of tumors showing BRCA1 locus deletion. To date, somatic mutations in BRCA1 have been found in very few cases of sporadic cancers (Futreal et al. 1994; Hosking et al. 1995; Merajver et al. 1995; Takahashi et al. 1995).

In further support of this hypothesis, more finely detailed deletion mapping has identified a 400 kb deletion unit approximately 60 kb centromeric to the BRCA gene in sporadic epithelial ovarian cancer (Tangir et al. 1996). This deletion unit may contain a putative tumor suppressor important for sporadic ovarian cancer and contains approximately 12 genes which were identified during the search for BRCA1. Six of them are known genes or human homologs of other species; gamma tubulin, homolog of D. melanogaster enhancer of zeste, pseudogene of HMG17, homology of Pacific electric ray VAT1, glucose-6-phosphatase and Ki antigen and six of them are novel genes.

This application describes the identification of the full-length open reading frame and functional characterization of one of these six novel genes, which is herein referred to as "beclin". This application shows that Beclin overexpression inhibits cellular proliferation in vitro and suppresses the ability of human breast carcinoma cells to form colonies in soft agar and tumors in nude mice. Thus, these studies demonstrate that beclin has tumor suppressor function. This application describes the sequences of the 5' and 3' untranslated regions of beclin, and provides evidence that, beclin may be functionally inactivated in human cancers by mutations in the gene which lead to loss of Beclin protein expression or by splice site mutations which lead to aberrant beclin splicing.

The cellular antiapoptotic gene bcl-2 represents a novel class of antiviral host defense molecules which function both by restricting viral replication and by preventing virus-induced cell death. Bcl-2 blocks apoptosis in vitro induced by several different RNA viruses, including Sindbis virus, influenza virus, reovirus, Semliki Forest virus, LaCrosse virus, and Japanese B encephalitis virus. Previously, we have shown that Bcl-2 overexpression in virally infected neurons in vivo also protects mice against fatal encephalitis caused by the prototypic alphavirus, Sindbis virus. The protective effects of Bcl-2 against fatal Sindbis virus encephalitis were associated with a reduction both in neuronal apoptotic death and in central nervous system (CNS) viral replication. A similar antiviral effect of Bcl-2 overexpression has been observed during Sindbis virus infection in cultured AT3 cells as well as during influenza virus infection of MDCK cells, Japanese B encephalitis virus infection of N18 cells, and Semliki Forest virus infection of AT3 cells. Although the role of endogenous Bcl-2 in antiviral defense has yet to be evaluated, these studies support the hypothesis that Bcl-2 may be important in protecting cells against viral infections.

The process of autophagy, or bulk degradation of cellular proteins through an autophagosomic-lysosomal pathway, is important in normal growth control and may be defective in tumor cells. However, little is known about the genetic mediators of autophagy in mammalian cells and whether genetic mediators of autophagy influence tumor development. Recently, 14 genes, the apg genes, have been identified in S. cerevisiae that are required for yeast autophagy[1]. The mammalian gene encoding Beclin 1[2], a novel Bcl-2-interacting, coiled-coil protein, shares structural similarity with the yeast autophagy gene product, Apg6/Vps30p[3,4], and is monoallelically deleted in 40–75% of sporadic human breast cancers and ovarian cancers [5-11]. Here we show, using gene transfer techniques, that beclin 1 promotes autophagy both in autophagy-defective yeast with a targeted disruption of apg6/vps30 and in autophagy-defective human MCF7 breast carcinoma cells. The autophagy-promoting activity of beclin 1 in MCF7 cells is associated with an ability to inhibit MCF7 cellular proliferation, in vitro clonigenicity, and tumorigenesis in nude mice. Furthermore, endogenous Beclin 1 protein expression is frequently undetectable or low in malignant human breast epithelial cell lines and tissue, but is expressed ubiquitously at high levels in normal breast epithelia. Thus, beclin 1 is a mammalian autophagy gene with tumor suppressor function that is expressed at decreased levels in human breast cancer. These findings indicate that there is an evolutionarily conserved genetic link between autophagy and tumor suppressor pathways, and raise the possibility that decreased expression of autophagy proteins may contribute to the development or progression of breast arid other human malignancies.

Autophagy is an evolutionarily conserved process that occurs in both yeast and mammalian cells in which there is bulk degradation of cellular contents via an autotphagosomal-lysosomal pathway. The process of autophagy liberates free amino acids and nucleotides and enable cells to survive under nutrient deprivation conditions as well as to undergo structural remodeling during differentiation. Protein degradation through an autophagy pathway has also been postulated to serve as a mechanism for negative regulation of cell growth. In support of this theory, cancerous transformation in vitro is associated with decreased rates of autophagic degradation. Malignant cell lines display less autophagic activity than their normal counterparts and are less prone to increase autophagic activity in response to serum deprivation or high cell density. Furthermore, in rat liver carcinogenesis models, there is an inverse correlation between stage of malignancy and autophagic activity. However, it is not known whether reduced autophagy in tumor cells directly contributes to deregulated cell growth, or alternatively, is the result of malignant transformation.

SUMMARY OF THE INVENTION

This invention provides a method of diagnosing a predisposition to carcinoma in a subject comprising: a) obtaining a nucleic acid sample from the subject; and b) determining whether one or more of the subject's beclin alleles or regulatory regions to those alleles are deleted or different from the wild type so as to reduce the subject's expression of polypeptide having tumor suppressor activity.

This invention also provides the above-described method, wherein one or more beclin alleles contain splice site junction mutations.

This invention provides also the above-described methods, wherein the determining of step (b) comprises determining whether one or more beclin promoter regions are hypermethylated.

Further, this invention provides the above-described methods, wherein the determining of step (b) comprises determining whether one or more beclin enhancer regions differ from the wild type.

This invention further provides the above-described methods, wherein the determining of step (b) comprises determining whether one or more beclin 5' or 3' nontranslated regions differ from the wild type.

This invention also provides the above-described methods, wherein the determining of step (b) comprises determining whether one or more beclin alleles have a premature termination codon.

This invention also provides the above-described methods, wherein a majority of the nucleotides corresponding to positions 1042–1185 of FIG. 1B have been deleted.

Further, this invention provides the above-described methods, wherein the subject was preselected based upon an abnormality at chromosome position 17q21.

This invention also provides the above-described methods, wherein the nucleic acid sample is obtained from the subject's blood.

This invention further provides a method of diagnosing a predisposition to carcinoma in a subject, comprising determining whether the subject has an abnormal subcellular distribution of Beclin.

In addition, this invention provides a method of diagnosing a predisposition to carcinoma in a subject, comprising contacting the contents of one or more of the subject's cells with one or more antibodies or fragments thereof specific to Beclin.

This invention provides a method for inhibiting viral replication comprising contacting an effective amount of Beclin with the virus infected cell, thereby inhibiting the viral replication where the method for inhibiting viral replication comprising contacting induction of the expression of Beclin with the virus infected cell, thereby inhibiting the viral replication.

A method of treating a viral infection in a subject, wherein the viral infection is alleviated by the expression of Beclin which comprises administering to the subject an effective amount of the pharmaceutical composition effective to express Beclin, thereby treating the viral infection in the subject.

In addition, this invention provides a method for treating cancer comprising inducing increased expression of Beclin, where the method for treating cancer comprises administering to the subject a therapeutically effective amount of beclin son as to restore cell growth control.

This invention provides a pharmaceutical composition which comprises Beclin and a pharmaceutically acceptable carrier.

BRIEF DESCRIPTION OF THE FIGURES

FIGS. 1A and 1B

Deduced amino acid sequence and nucleotide sequence of human beclin.

FIG. 1A

The deduced amino acid sequence (SEQ I.D. NO.:1) was used to scan various data banks. The boxed area represents the Bcl-2 binding domain of human Beclin (see Table 1) and the underlined area corresponds to the region that is predicted to have a coiled-coil conformation.

FIG. 1B

The nucleotide sequence (SEQ I.D. NO.:2) of human Beclin. The partial nucleotide sequence of mouse Beclin obtained from sequencing clone F1 was aligned with an overlapping clone GT197 isolated from human breast (Rommens, 1995). Primers immediately upstream and downstream of the predicted open reading frame were used to amlify he coding sequence of human beclin from a normalized human infant brain cDNA library (Soares, M. B., et al., 1994).

FIGS. 2A, 2B, 2C and 2D

Figures 2A, 2B:
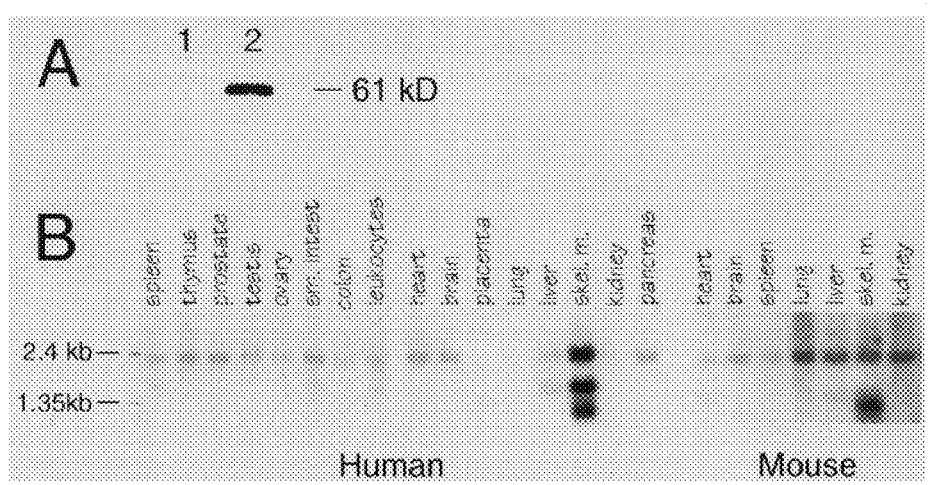

Beclin mRNA and protein expression. For FIGS. 2C and 2D, cells were co-transfected with 4 μg of pSG5/human bcl-2 and 4 µg of pSG5/beclin using lipofectin and fixed after 48 hours with 100% ETOH. Beclin expression was detected with a monoclonal anti-flag M2 Ab (1:20) and FITC-conjugated horse anti-mouse IgG Ab and Bcl-2 expression was detected with a polyclonal rabbit anti-Bcl-2 Ab and rhodamine-conjugated goat anti-rabbit Ab. Individual co-transfected cells were analyzed with confocal laser microscopy. In FIG. 2B, equal amounts of loading (2 µg of poly A) was confirmed by hybridization to a B-actin probe.

FIG. 2A

Western blot analysis of cell lysates prepared from BHK cells infected with a recombinant Sindbis virus chimera containing a flag epitope tagged human beclin insert (lane 2) or a control recombinant Sindbis virus chimera (lane 1) and probed with an anti-flag antibody M2 antibody (IBI) using well-known methods.

FIG. 2B

Northern blot analysis of beclin mRNA expression in human and mouse tissues. Human and mouse multiple tissue blots (Clontech) were hybridized respectively, according to manufacturer's instructions (Clontech) with a $^{32}$P-labeled 485 base pair probe corresponding to nucleotides 1–485 of human or mouse beclin. Beclin-specific probes hybridized to 2.3 kb transcripts in all examined tissues.

FIG. 2C

Immunofluorescence staining of human bcl-2 in a BHK cell.

FIG. 2D

Figure 2C:
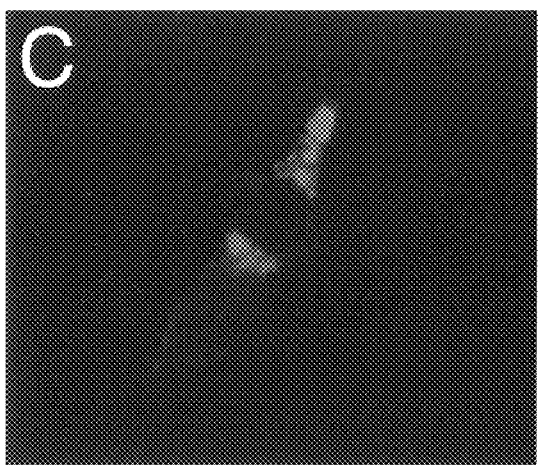
Figure 2D:
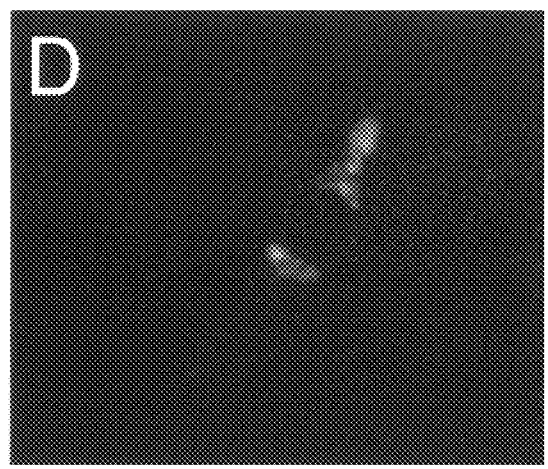

Immunofluorescence staining of human beclin in the same BHK cell shown in FIG. 2C.

FIGS. 3A, 3B, 3C, 3D, 3E, 3F, 3G, 3H, and 3I

Interactions of Bcl-2 and Beclin in vivo demonstrated using FRET microscopy. For the experimental cells, there were three types of labeling: acceptor and donor (n=7), donor alone (n=10), and acceptor alone (n=10). Each labeling type was imaged using the three filter sets: the donor filter set, the acceptor filter set, and the combination set (i.e. FRET set) which best detects the FRET signal. Several cells of each type were imaged so that there were many possible triplets of cells consisting of one each of acceptor plus donor, donor alone and acceptor alone. All possible triplets were analyzed; triplets which generated divide by zero erros of negative energy transfers were excluded. The same method was applied to the control cells where there were 13 acceptor plus donor cells, 10 donor cells alone and 10 acceptor cells alone.

Figure 3G:
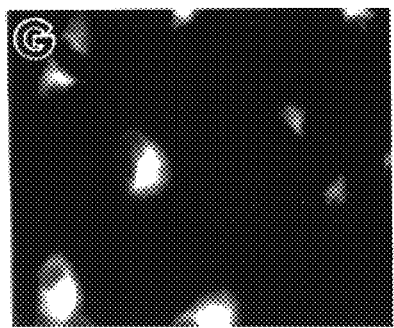

FIGS. 3A, 3D, and 3G

Donor (FITC) filter set was used.

Figure 3H:
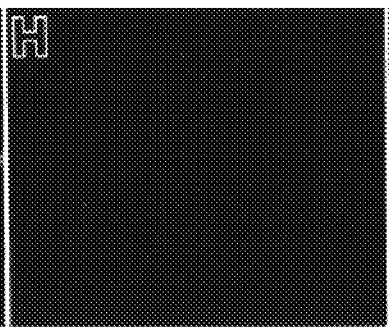

FIGS. 3B, 3E, and 3H

FRET filer set was used.

Figure 3I:
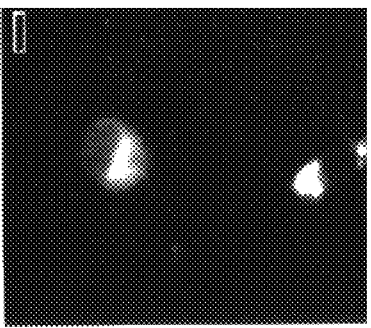

FIGS. 3C, 3F, and 3I

Acceptor (Rhodamine) filter set was used.

FIGS. 3A, 3B, 3C, 3D, 3E, and 3F

Cos cells co-transfected with flag epitope-tagged Beclin and Bcl-2, labeled with anti-flag (donor, FITC) and anti-Bcl-2 (acceptor, Rhodamine) specific antibodies, respectively.

FIGS. 3G, 3H, and 3I

Cos cells transfected with Bcl-2 labeled with antibodies against SERCA (Research Design, Inc.) (donor, FITC) and Bcl-2 (acceptor, Rhodamine). Cos cells were co-transfected with pSG5/flag-Beclin and pSG5/BCL-2, labeled as in FIGS. 2C and 2D, and FRET microscopy was performed as described herein.

Figure 4C:
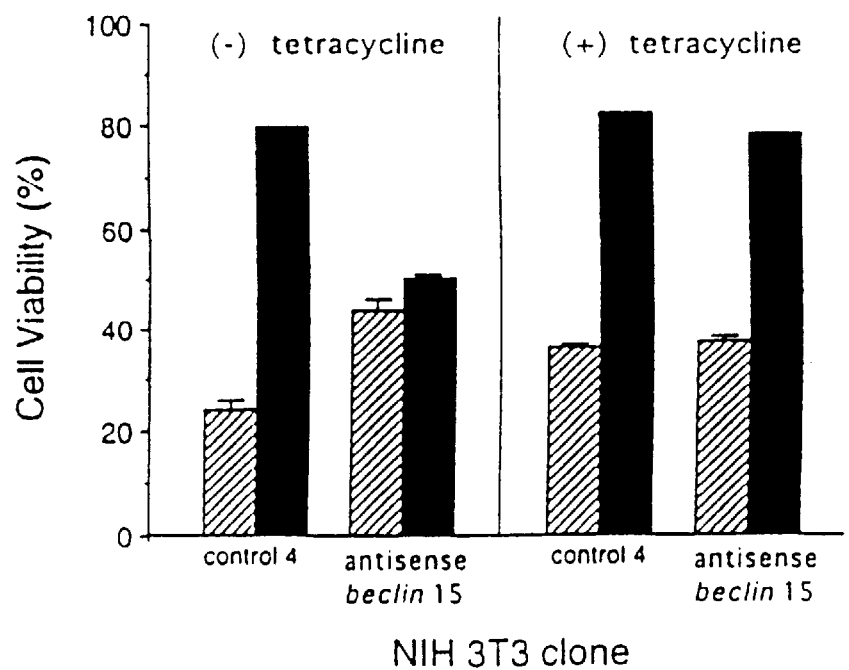

FIGS. 4A, 4B, and 4C

Effect of beclin and antisense beclin on Sindbis virus-induced apoptosis. Recombinant chimeric viruses SIN/antisense bcl-2, SIN/antisense beclin were constructed using methods described for the construction of SIN/flag-beclin and infected at a multiplicity of infection (MOI) of one plaque-forming unit per cell. Cell viability was determined by trypan blue exclusion at serial time points after infection in FIG. 4A and FIG. 4B, and at 24 hours after infection in FIG. 4C. The results of triplicate wells are shown (mean= S.E.) Similar results were obtained in more than 5 independent experiments for FIG. 4A and FIG. 4B and in three independent experiments in FIG. 4C.

FIG. 4A

Cell viability of BHK cell death after infection with recombinant Sindbis viruses containing bcl-2 in either the sense (SIN/bcl-2) or antisense orientation (SIN/antisense bcl-2) or beclin in either the sense (SIN/beclin) or antisense orientation (SIN/antisense beclin).

FIG. 4B

Cell viability of AT3/Bcl-2 cells after infection with SIN/CAT, SIN/beclin, SIN/antisense beclin, or SIN/antisense bcl-2.

FIG. 4C

Cell viability of NIH 3T3 antisense beclin and NIH 3T3 control cells after infection with Sin/bcl-2 (shaded bars) or SIN/bcl-2 stop (hatched bars) in the presence or absence of tetracycline. NIH 3T3 clones were cultured for three days in the presence or absence of 1 µg/ml tetracycline prior to infection.

Figure 5A:
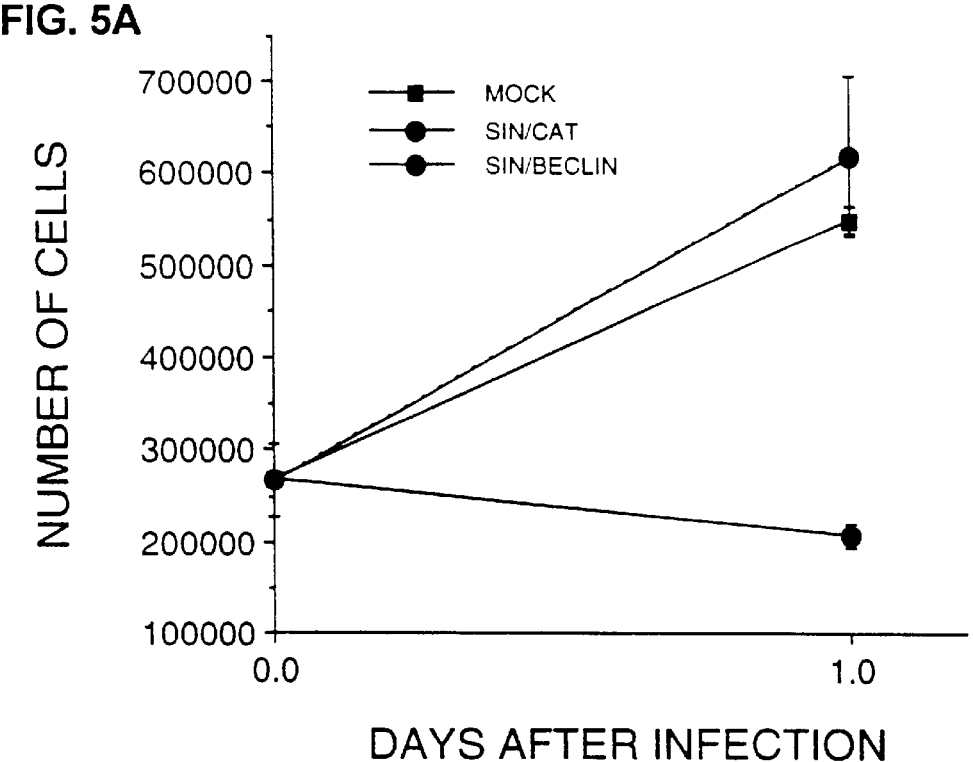
Figure 5B:
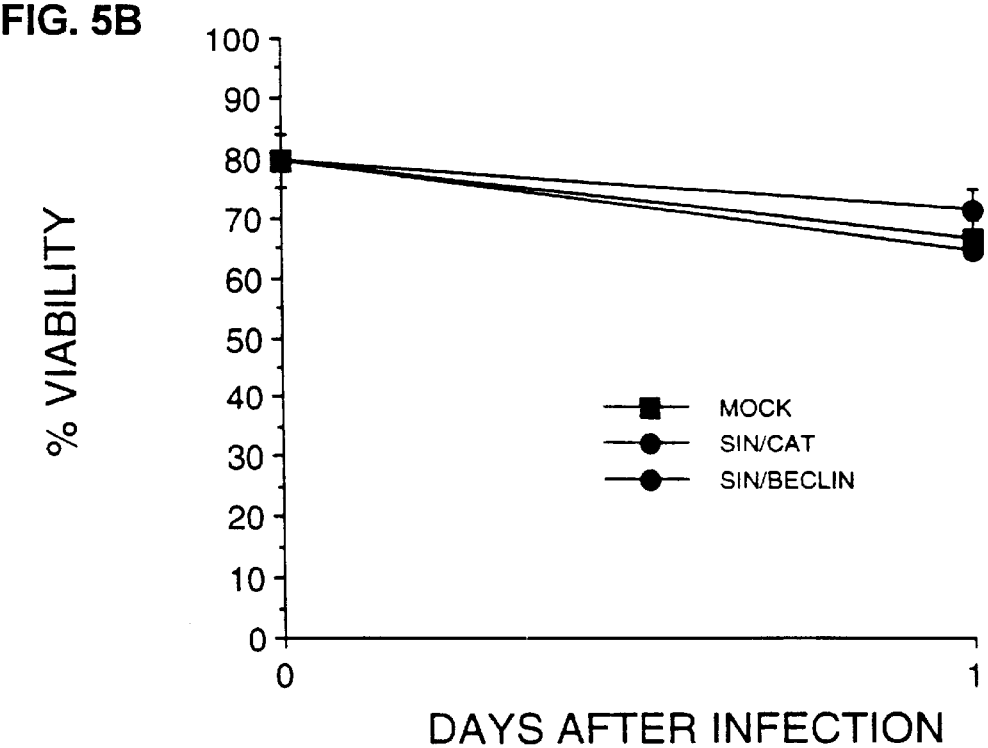
Figure 5C:
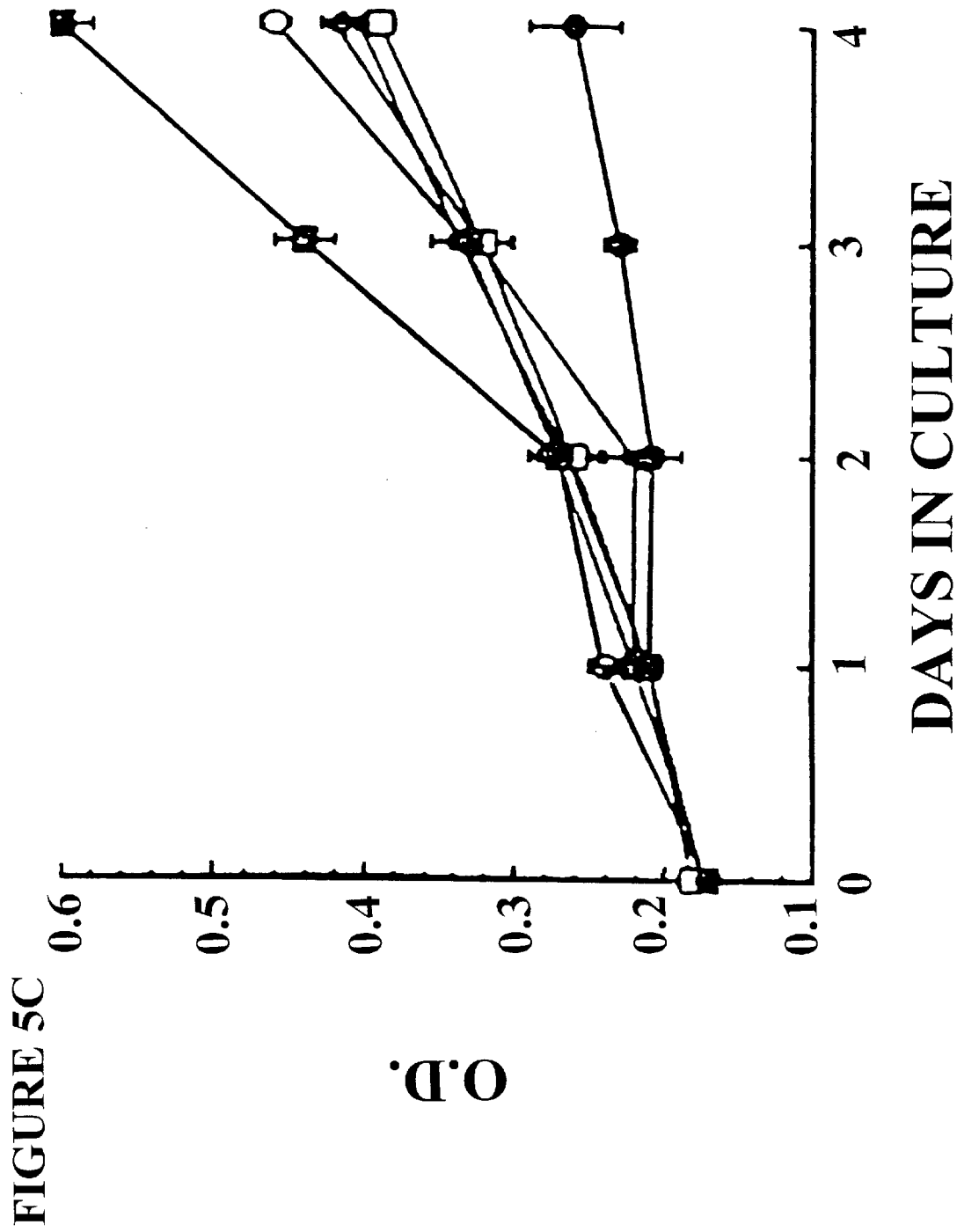

FIGS. 5A, 5B, and 5C

Effect of beclin on AT3 and mouse fibroblast NIH 3T3 cellular proliferation. For FIGS. 5A and 5B, 5×10$^5$ cells were seeded in 35 mm wells, and 24 hours later, infected at a MOI of 1. Results are presented as means±s.e. For FIG. 5C, cells were cultured for three days±tetracycline prior to seeding 5×10$^5$ cells/well in 96 well plates. At several time points in culture, cells proliferation was measured by performing MTT assays (MTT proliferation kit, Boehringer Mannheim) according to the manufacturer's instructions. Results are presented as mean O.D.±s.e for triplicate wells. Similar results were obtained in three independent experiments.

FIG. 5A

Determination of total cell number of AT3/bcl-2 cell number.

FIG. 5B

Determination of percentage of cell viability of AT3/blc-2 cell viability after infection with SIN/CAT (open circles), SIN/beclin (solid circles) or mock infection (solid squares).

FIG. 5C

NIH beclin clone 10 (circles), NIH antisense beclin clone 15 (squares) and NIH control clone 4 (triangles) proliferation in the presence (open symbols) or absence (cloned symbols) of tetracycline.

Figure 6A:
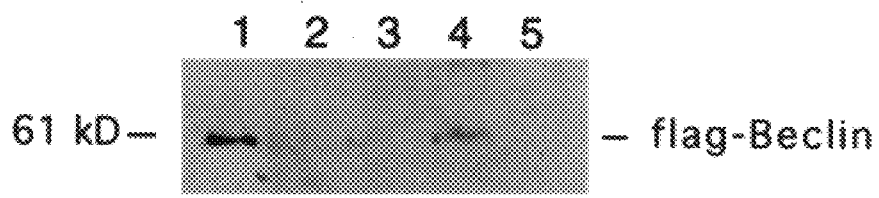
Figure 6B:
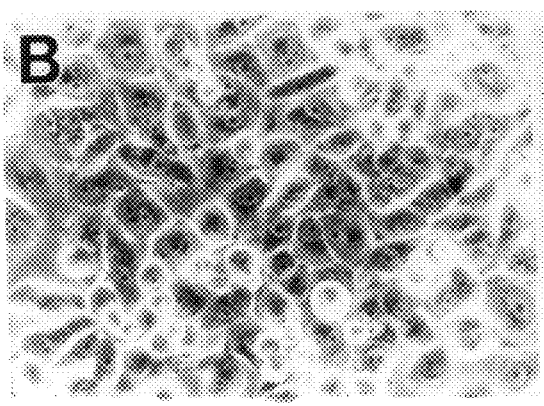
Figure 6C:
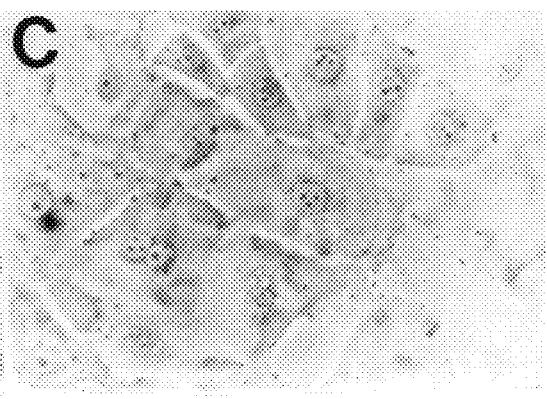

FIGS. 6A, 6B, and 6C

Effect of beclin transfectlon on the morphology of human MCF7 breast carcinoma cells.

FIG. 6A

Western blot analysis of flag-Beclin expression in MVF7 clones transfected with BC252SV40/beclin. BHK cell lysates infected with a recombinant Sindbis virus expressing flag-tagged Beclin is used as a positive control (lane 1). MCF7 Beclin clones 1, 4 and 17 (lanes 2, 3 and 4 respectively) and a control MCF7 clone (lane 5). Clone 17, lane 4 demonstrates Beclin immunoreactivity.

FIG. 6B

Phase contrast micrographs of MCF7 control clone 5 cells.

FIG. 6C

MCF7 Beclin clone 17 cells at 375×magnification.

FIG. 7

Diagram of plasmid pSG5/beclin (ATCC Accession No. 97664). The 1.4 kb insert encoding Beclin was inserted into Eco RI sites in the plasmid, pSG5 (Stratagene).

FIGS. 8A and 8B

Nucleotide sequence of 5' untranslated region of human beclin (A) and 3' untranslated region of human beclin (B).

FIG. 8A

The sequence of the insert in the plasmid TA/clone 5 (SEQ I.D. NO.:3).

FIG. 8B

The sequence of the insert On the clasmid TA/clone 13 (SEQ I.D. NO.:4).

FIG. 9A

Figure 9A:
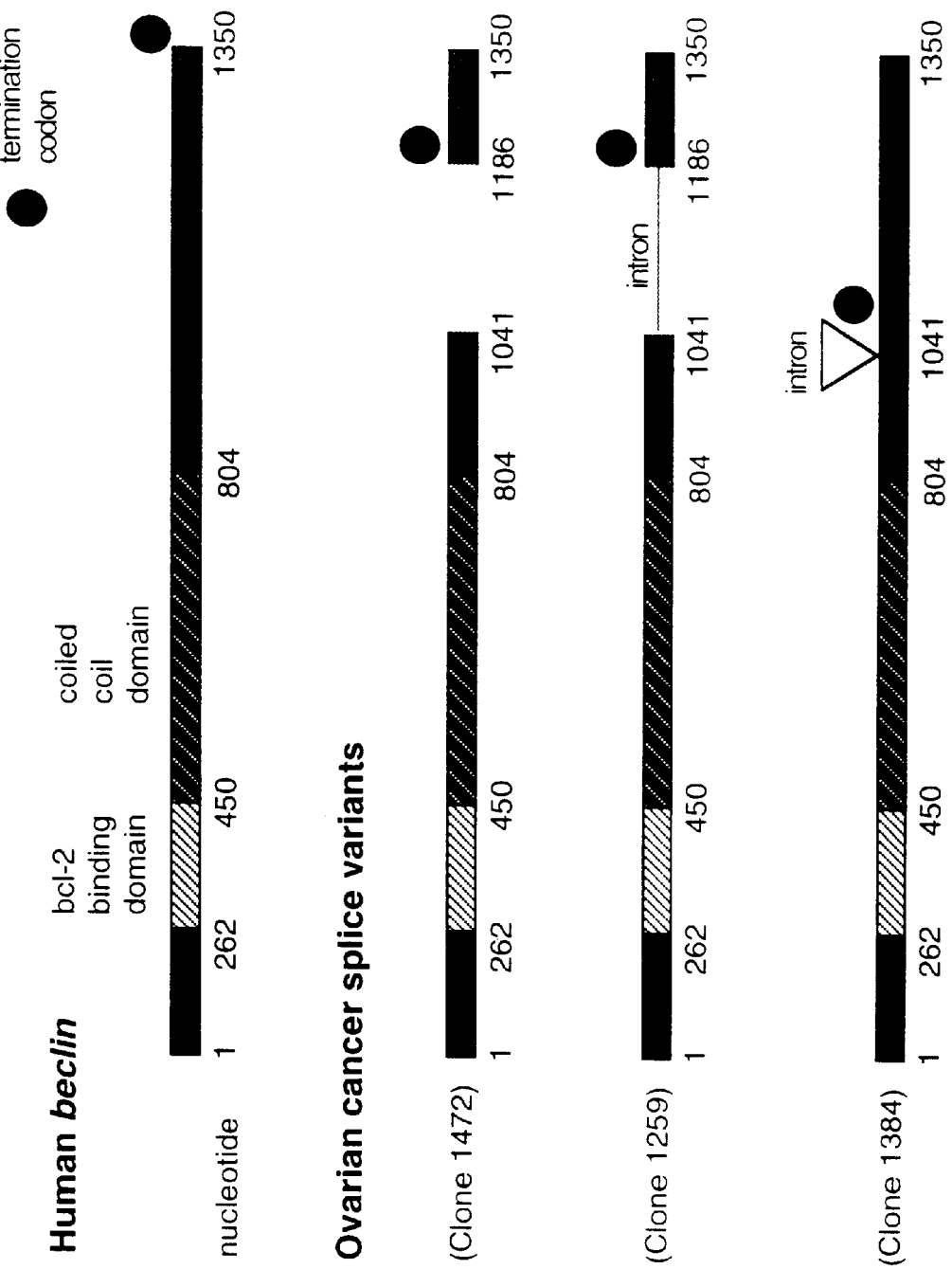

Schematic diagram of wild-type beclin aberrant beclin transcripts found in sporadic epithelial ovarian cancer. The clone number listed on the left of each of the three ovarian cancer splice variants refer to cloned transcripts that represent each type of aberrant splice pattern, and corresponds to the insert sequences provided in FIGS. 9C–9E.

FIG. 9B

Nucleotide sequence (SEQ I.D. NO.:5) and its predicted translation of wild-type human beclin (SEQ I.D. NO.:6 and 7). In another polymorphic form, the nucleotide at position 308, shown as a (lower case) "c" may instead be a T, thus resulting in a valine.

FIG. 9C

Nucleotide sequence (SEQ I.D. NO.:8) and its predicted translation of mutant beclin clone 1472 (SEQ I.D. NO.:9). In another polymorphic form, the nucleotide at position 308, shown as a (lower case) "c" nay instead he a T, thus resulting in a valine.

FIG. 9D

Nucleotide sequence (SEQ I.D. NO.:10) and its. predicted translation of mutant beclin clone 1259 (SEQ I.D. NO.:11). In another polymorphic form, the nucleotide at position 308, shown as a (lower case) "c" may instead be a T, thus resulting in a valine.

FIG. 9E

Nucleotide sequence (SEQ I.D. NO.:12) and its predicted translation of mutant beclin clone 1384 (SEQ I.D. NO.:13). In another polymorphic form, the nucleotide at position 308, shown as a (lower case) "c" may instead be a T, thus resulting in a valine.

Figure 10A:
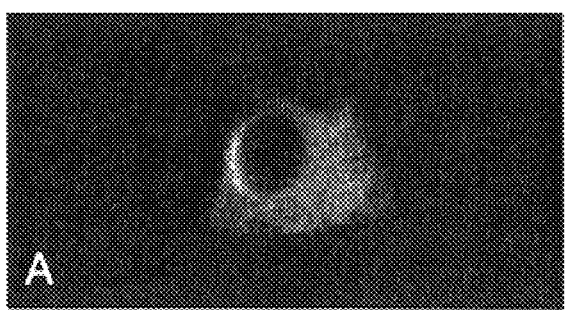
Figure 10B:
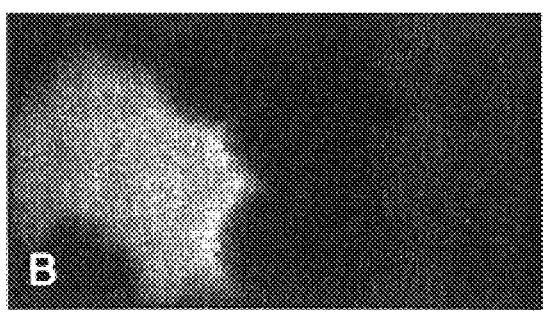

FIGS. 10A and 10B

MCF7 cells were transfected with pSG5 expression vectors containing flag epitope-Tagged Beclin or flag epitope-tagged mutant BeclinΔ1042–1185, fixed after 24 hours with 100% ETOH, and subjected to immunofluorescence staining to detect flag-Beclin expression with an anti-flag antibody M2 (VWR Scientific).

FIG. 10A

Subcellular localization of wild-type Beclin.

FIG. 10B

Subcellular localization of mutant beclin deleted of nucleotides 1042–1185 (BeclinΔ1042–1185).

FIG. 11

Western blot analysis of Beclin protein expression. Western blot analysis of human Beclin protein expression in matched normal and tumor breast tissue from patients with sporadic invasive breast carcinoma. Twenty-five microliters of homogenized breast tissue (diluted 1:1 in SDS sample buffer) was subjected to SDS-Page, transferred to nitrocellulose, probed with a polyclonal anti-human Beclin peptide (amino acid 1–15) antibody 843 (custom production by Eurogenetics, Belgium), and Beclin protein was detected with ECL (Amersham) according to manufacturer's instructions. The positive control represents baby hamster kidney cell lysates prepared 24 hours after Infection with a Sindbis virus vector which overexpresses human Beclin.

Figure 12A:
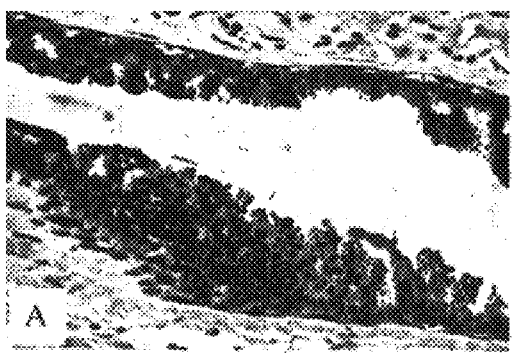
Figure 12B:
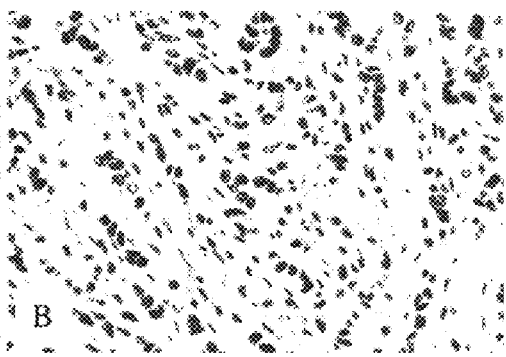

FIGS. 12A and 12B

Figure 11:
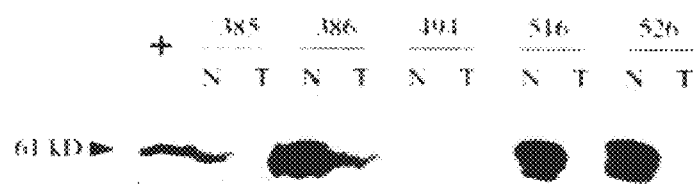

Immunocytochemical analysis of Beclin protein expression in normal breast tissue (FIG. 12A) and malignant breast tissue (FIG. 12B) from patient 516 (see FIG. 11 Western blot) using the anti-human Beclin antibody 843 and the ABC immunoperoxidase method. Normal epithelial cells (FIG. 12A) display marked Beclin immunoreactivity whereas malignant epithelial cells (FIG. 12B) display no Beclin immunoreactivity.

FIG. 13

Deduced amino acid sequence of human Beclin. The boxed area represents the Bcl-2-binding domain of human Beclin (Table 1), and the underlined area corresponds to the region that is predicted to have a coiled-coil conformation.

FIG. 14

Beclin mRNA and protein expression. (A) Northern blot analysis of beclin mRNA expression in human and mouse tissues. Sm., small; m., muscle. (B) Immunoperoxidase staining of an adult human hippocampus section with a polyclonal antibody against a human Beclin peptide. The arrow marks a Beclin-positive neuron. Magnification, ×450.

FIG. 15

Expression of flag-Beclin protein constructs by the virus vectors SIN/beclin, SIN/beclinstop, and SIN/beclinΔBcl-2BD, (A and B) Western blot analyses of virus-infected BHK cell lysates with either anti-flag epitope antibody M2 (A) or polyclonal rabbit anti-Beclin antiserum (B). Lane 1, SIN/beclin; lane 2 SIN/beclinstop; lane 3, SIN/beclinΔBcl-2BD1; lane 4, empty Sindbis virus vector. (C to E) Immunoperoxidase stainingusing anti-flag epitope antibody M2 of mouse brains 2 days after infection with SIN/beclin (C), SIN/beclinstop (D), or SIN/beclinΔBcl-2BD (E). Magnification X111.

FIG. 16

Confocal laser scanning microscopy of COS7 cells expressing Bcl-2 and Beclin. (A and B) Cell cotransfected with pSG5/bcl-2 and pSG5/flag-beclin and stained with anti-flag epitope (A) and anti-human Bcl-2 (B) antibodies. (D and E) Cell cotransfected with pSG5/bcl-2 and pSG5/flag-beclinDBcl-2BD and stained with anti-flag epitope (D) and anti-human Bcl-2 (E) antibodies. (C and F) Computerized overlays of panels A and B(C) and panels D and E(F); yellow color corresponds to overlap of FITC and rhodamine staining. Confocal slides were 1 μm thick.

FIG. 17

Effects of Beclin and Bcl-2 and Bcl-2 on the survival of mice infected with Sindbis virus strain TE12. (A) Survival curve of mice infected with SIN/beclin, SIN/beclinstop, and SIN/bcl-2stop. Data represent combined survival probabilities for three independent litters.

FIG. 18

Viral growth of SIN/beclin, SIN/beclinstop, and SIN/beclinΔBcl-2BD in mouse brain. Each data point represents geometric mean viral titer±SEM of three to six mouse brains.

FIG. 19

Viral RNA-positive cells in mouse brains infected with SIN/beclin, SIN/beclinstop, and SIN/beclinΔBcl-2BD. Each data point represents the mean±SEM number of Sindbis virus message-sense RNA-positive cells per square millimeter of brain for three to six mouse brains.

FIG. 20

Apoptotic nuclei in mouse brains infected with SIN/beclin, SIN/beclinstop, and SIN/beclinΔBcl-2BD. Each data point represents the mean±SEM number of ISEL-positive nuclei per square millimeter of brain for three to six mouse brains.

FIG. 21

Figure 19:
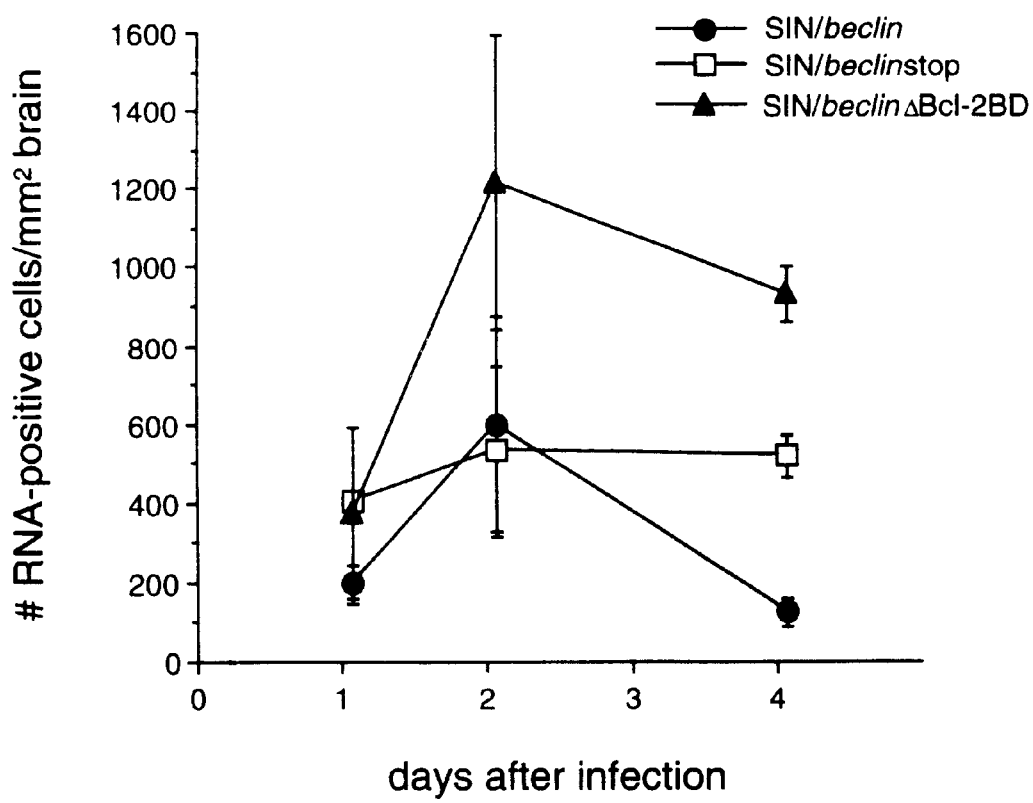
Figure 20:
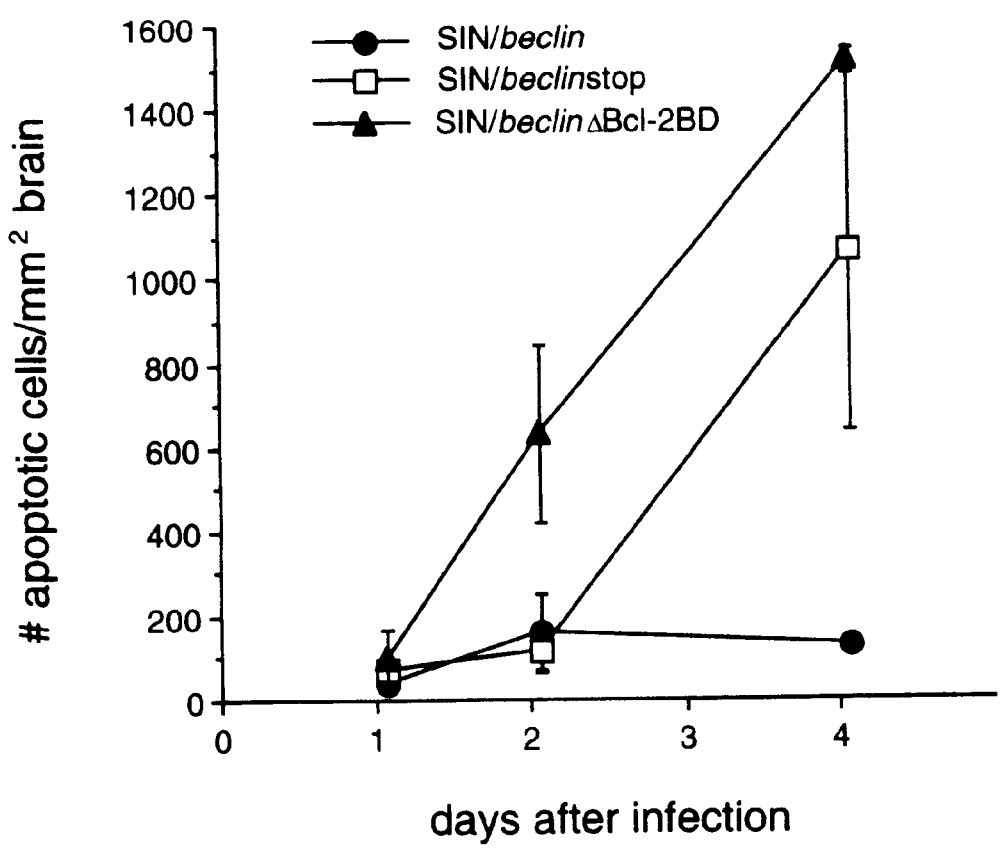

Representative photomicrographs of fields used for computerized quantitative image analysis of viral RNA (A to C)—and ISEL (D to F)—positive cells in mouse brains infected with SIN/beclin (A and D), SIN/beclinstop (B and E), and SIN/beclinΔBcl-2BD (C and F) in FIG. 19 and 20, respectively. All photomicrographs are from he colliculus region of brain sections 4 days after infection and correspond to the images observed at a magnification of ×10. Arrowheads denote representative cells that were scored as positive by the Image-ProPlus software program.

FIG. 22

Shows the growth curve of the virus, a gammaherpesvirus 68, in human MCF7 breast carcinoma cells that are transfected with an empty vector (MCF7/control cells) or with a vector expressing human beclin (MCF/beclin cells).

FIG. 23

Complementation of apg6/vps30 by beclin 1 in yeast autophagy. a, Western blot with polyclonal anti-flag antibody demonstrating flag epitope-tagged human Beclin 1 expression in JCY3000+pRS424.beclin1 yeast transformants. Positive control (lane 1) represents lysate of mammalian cells transfected with mammalian flag-beclin 1 expression vector. Negative controls (lanes 2, 3, 4) represent SEY6210, JCY3000, and JCY3000+pRS424. vps30 yeast, respectively. Lanes 5 and 6 represent independent JCY3000 yeast clones (clones beclin 1.3 and beclin 1.5) with homologous recombination replacement of flag beclin 1 for the apg6/vps30 ORF in the plasmid pRS424.vps30. b, Photomicrographs of autophagic body formation in yeast subjected to nitrogen deprivation in the presence and absence of 1 mM PMSF. SEY6210 is wild-type, and JCY3000 is disrupted of apg6/vps30. Arrows denote representative cells which would be scored as positive in experiment shown in c. c, Quantitative effects of apg6/vps30 and beclin 1 transformation on autophagic body formation in apg6/vps30-disrupted yeast in the presence of PMSF. Autophagic bodies were defined as visible bodies within the vacuole of the yeast (see arrows in b). A minimum of 100 cells was counted for each sample for each yeast strain. The results shown represent the mean±S.E.M. for triplicate samples. Similar results were obtained in three independent experiments.

FIG. 24

Promotion of autophagy by enforced beclin 1 expression in human MCF7 breast carcinoma cells. Representative electron micrographs of MCF7.control clone 38 (a,c) and MCF7.beclin1 clone 17 cells (b, d, e) grown in nutrient-rich media (a, b) or subjected to 3.5 hours of serum and amino acid deprivation (c–e). Asterisks in e denote representative autophagic vacuoles which would be counted in experiment shown in f. Scale bars=2_m. f, Quantitative effects of beclin 1 on basal and nutrient-deprivation induced autophagy of MCF7 cells. Solid bars indicate mean±S.E.M. number of autophagic vacuoles per cell for cells growing in normal media. Hatched bars indicate mean±S.E.M. number of autophagic vacuoles per cell for cells subjected to 3.5 hours of serum and amino acid deprivation. Open bars indicate mean±S.E.M. number of autophagic vacuoles per cell for cells pre-treated for 30 minutes with 10 mM 3-methyladenine, and then subjected to 3.5 hours of serum and amino acid deprivation. The mean number of autophagic vacuoles per cell was determined by counting the total number of autophagic vacuoles in each cell for 100 cells per clone per treatment group. Autophagic vacuoles were defined a (double-membrane containing vacuolar structures containing recognizable cytoplasmic contents (see representative vacuoles in e).

FIG. 25

Effects of enforced beclin 1 expression on growth properties and tumorigenicity of MCF7 cells. a, Western blot analysis of flag epitope-tagged beclin 1-transfected MCF-7 clones using anti-flag M2 antibody. (+) control represents lysates of BHK cells infected with Sindbis virus vector expressing flag-Beclin $1^2$. (−) control represents MCF7.control clone 38. b, Representative photomicrographs demonstrating morphologic appearance of MCF7.control clones (left panel, clone 5) and MCF7.beclin1 clones (right panel, clone 17) 48 hours after seeding at similar densities. c, Proliferation of MCF7.control clones (closed symbols) and MCF7.beclin1 clones (open symbols). Y axis represents O.D. values measured by MTT assay. Results shown represent mean+S.E.M. for triplicate wells. Similar results were obtained in three independent experiments. d, Clonigenicity in semi-solid medium (soft-agar) of MCF7.control and MCF7.beclin1 clones. Results shown represent mean±S.E.M. for pooled triplicate wells from 3–4 independent experiments. e, Tumor formation in NCR nude mice injected subcutaneously with MCF.control and MCF-.beclin1 clones. Numbers on top of bar represent number of autopsy-confirmed tumors at eight weeks/number of rice injected wish each clone. Immunoperoxidase staining to detect flag-Beclin 1 in MCF7.control clone 5 (top row) and MCF.beclin1 clone 17 cells (bottom row) prior to injection into nude mice (left column) and in tumors arising in nude mice (right column) using anti-flag M2 antibody. Arrow denotes cluster of flag-Beclin 1 immunoreactive cells.

FIG. 26

Decrease in Beclin 1 protein expression in human breast cancer cell lines and tissue. a, Western blot analysis using anti-Beclin 1 and anti-actin antibodies of representative breast cancer cell lines. b, Western blot analysis using anti-Beclin 1 and anti-actin antibodies of matched normal and malignant breast tissue from representative patients with sporadic invasive breast carcinoma. c, Immunoperoxidase staining using anti-Beclin 1 antibody of paraffin-embedded sections of matched normal and malignant breast tissue from two patients shown in b. In b and c, N=normal breast tissue, T=tumor tissue.

FIG. 27

Western Blot analysis of Beclin 1 expression in MCF7 cell. treated with tamoxifen.

DETAILED DESCRIPTION OF THE INVENTION

In order to facilitate an understanding of the Experimental Details section which follows, certain frequently occurring methods and/or terms are described in Sambrook, et al. (1989).

Throughout this application, references to specific nucleotides are to nucleotides present on the coding strand of the nucleic acid. The following standard abbreviations are used throughout the specification to indicate specific nucleotides:
C=cytosine
A=adenosine
T=thymidine
G=guanosine In an embodiment, a "gene" includes a nucleic acid molecule, the sequence of which includes all the information required for the normal regulated production of a particular protein, including the structural coding sequence, promoters and enhancers.

In an embodiment a wildtype human Beclin includes a polypeptide which has an amino acid sequence identical to that present in a naturally-occurring form of human Beclin. In an embodiment, a mutant human Beclin includes a polypeptide having an amino acid sequence which differs by one or more amino residues from any naturally occurring form, including deletions mutants containing less than all of the residues present in the wildtype polypeptide, substitution homologs wherein one or more residues are replaced by other residues, and addition homologs wherein on or more amino acid residues are added to a terminal or medial portion of the polypeptide.

The nucleic acids and oligonucleotides described and claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

The present invention provides for an isolated nucleic acid which encodes a wildtype human Beclin. This invention further provides an isolated nucleic acid which encodes a mutant human Beclin. The above-described isolated nucleic acids can be DNA, specifically cDNA or genomic DNA, and RNA.

In an embodiment, a "mutant human Beclin" includes polypeptides that whose nucleic acid sequence or amino acid seqeunce differs from that of the naturally-occuring wildtype human Beclin. For example, due to a point mutation, the translated polypeptide differs from the naturally-occuring wildtype protein. Further, a subject may have low expression of the naturally-occurring protein so that the cells with this low-expressing protein cannot inhibit cell proliferation.

This invention also provides for a vector comprising the above-described nucleic acid operatively linked to a promoter of RNA transcription.

Numerous vector backbones are known in the art and are useful for expressing proteins. Such vectors include plasmid vectors, cosmid vectors, yeast artificial chromosome (YAC), bacteriophage or eukaryotic viral DNA. For example, one such class of vectors comprises DNA elements derived from viruses such as bovine papilloma virus, polyoma virus, adenovirus, vaccinia virus, baculovirus, retroviruses (RSV, MMTV or MoMLV), Semliki Forest virus or SV40 virus. Such vectors may be obtained commercially or assembled from the sequences described by methods well-known in the art.

Figure 7:
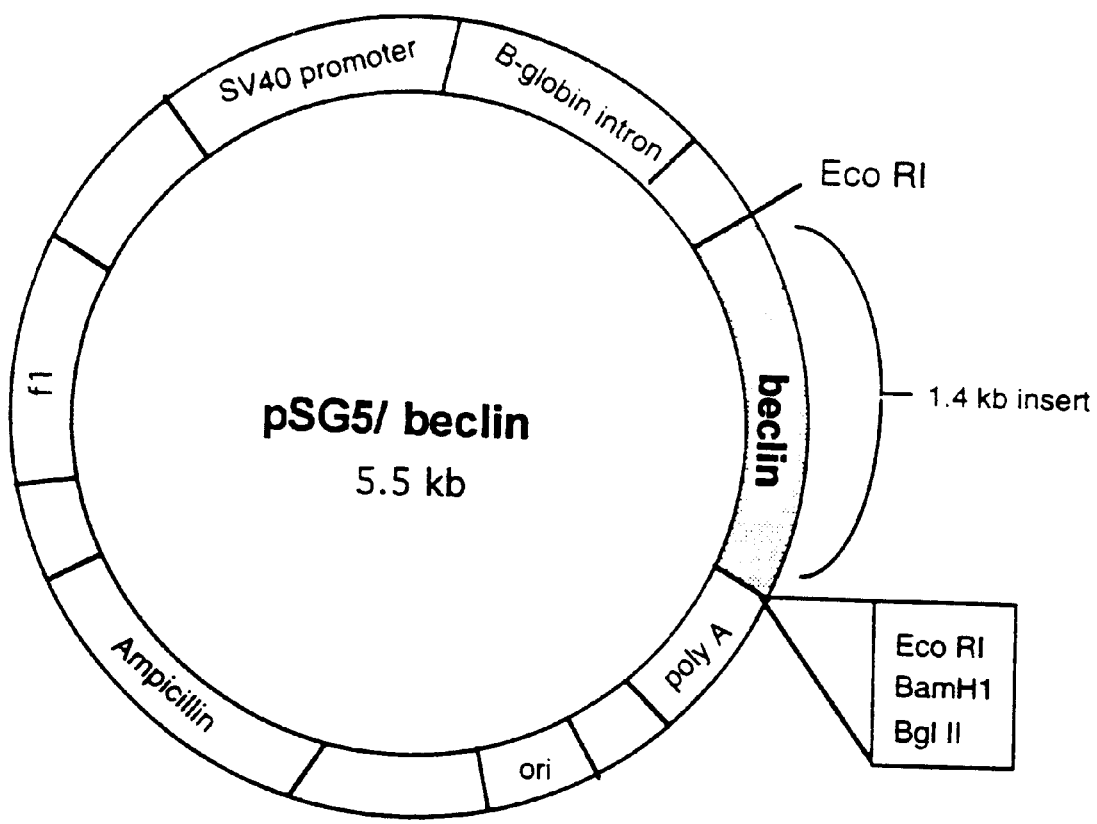

This invention specifically provides a plasmid designated pSG5/beclin. Plasmid pSG5/beclin was made by cleaving DNA which encodes a wildtype human Beclin and inserting the DNA into the Eco RI site of pSG5 (FIG. 7). pSG5/beclin was deposited on Jul. 18, 1996 with the American Type Culture Collection (ATCC), 12301 Parklawn Drive, Rockville, Md. 20852, U.S.A., under the provisions of the Budapest Treaty For The International Recognition Of The Deposit Of Microorganisms For The Purposes Of Patent Procedure. pSG5/beclin has been accorded ATCC Accession Number 97664.

These vectors may be introduced into a suitable host cell to form a host vector system for producing the inventive proteins. Methods of making host vector systems are well known to those skilled in the art.

Suitable host cells include, but are not limited to, bacterial cells (including gram positive cells), yeast cells, fungal cells, insect cells and animal cells. Suitable animal cells include, but are not limited to HeLa cells, Cos cells, CV1 cells and various primary mammalian cells. Numerous mammalian cells may be used as hosts, including, but not limited to, the mouse fibroblast cell NIH-3T3 cells, CHO cells, HeLa cells, Ltk cells and COS cells. Mammalian cells may be transfected by methods well known in the art such as calcium phosphate precipitation, electroporation and microinjection.

This invention also provides a host vector system for the production of a polypeptide which comprises the above-described vector in a suitable host.

This invention also provides a method of producing a polypeptide which comprises growing the above-described host vector system, under suitable conditions permitting production of the polypeptide and recovering the polypeptide so produced. Further, this invention also provides a method of obtaining a polypeptide in purified form which comprises (a) introducing the above-described vector into a suitable host cell, (b) culturing the resulting host cell so as to produce the polypeptide, (c) recovering the polypeptide produced into step (b); and (d) purifying the polypeptide so recovered. In the above-described method, the vector comprises a plasmid, cosmid, yeast artificial chromosome (YAC), bacteriophage or eukaryotic viral DNA and the suitable host cell comprises a bacterial, insect, plant or mammalian cell.

This invention also provides a purified, wildtype human Beclin. In an embodiment, wildtype human Beclin includes a polypeptide which has an amino acid sequence identical to that present in a naturally-occurring form of human Beclin.

This invention also provides an oligonucleotide of at least 15 nucleotides capable of specifically hybridizing with a unique sequence of nucleotides within a nucleic acid which encodes a wildtype Beclin without hybridizing to any sequence of nucleotides within a nucleic acid which encodes a mutant human Beclin. Further, this invention also provides an oligonucleotide of at least 15 nucleotides capable of specifically hybridizing with a unique sequence of nucleotides within a nucleic acid which encodes a mutant Beclin without hybridizing to any sequence of nucleotides within a nucleic acid which encodes a wildtype human Beclin. The above-described oligonucleotides may DNA or RNA. Methods of manufacturing such oligonucleotides and using the oligonucleotides are well-known in the art.

This invention also provides a method for determining whether a subject has a predisposition for cancer which comprises (a) obtaining an appropriate nucleic acid sample from the subject; and (b) determining whether the nucleic acid sample from step (a) is, or is derived from, a nucleic acid which encodes a mutant human Beclin so as to thereby determine whether a subject has a predisposition for cancer. Various methods of determining whether he nucleic acid sample is, or is derived from, a nucleic acid which encodes a mutant human Beclin exist.

In one example, the nucleic acid sample in step (a) comprises mRNA corresponding to the transcript of DNA encoding a mutant Beclin, and wherein the determining of step (b) comprises (i) contacting the mRNA with the above-described oligonucleotide, which is capable of specifically hybridizing with a unique sequence or nucleotides within a nucleic acid which encodes a mutant Beclin without hybridizing to any sequence of nucleotides within a nucleic acid which encodes a wildtype human Beclin, under conditions permitting binding of the mRNA to the oligonucleotide so as to form a complex, (ii) isolating the complex so formed, and (iii) identifying the mRNA in the isolated complex so as to thereby determine whether the mRNA is, or is derived from, a nucleic acid which encodes a mutant human Beclin.

In another example, the determining of step (b) comprises (i) contacting the nucleic acid sample of step (a), and the isolated nucleic acid which encodes a wildtype human Beclin with restriction enzymes under conditions permitting the digestion of the nucleic acid sample, and the isolated nucleic acid into distinct, distinguishable pieces of nucleic acid, (ii) isolating the pieces of nucleic acid; and (iii) comparing the pieces of nucleic acid derived from the nucleic acid sample with the pieces of nucleic acid derived from the isolated nucleic acid so as to thereby determine whether the nucleic acid sample is, or is derived from, a nucleic acid which encodes a mutant human Beclin.

In another example, the determining of step (b) comprises (i) sequencing the nucleic acid sample of step (a); and (ii) comparing the nucleic acid sequence of step (i) with the above-described isolated nucleic acid having a sequence substantially the same as the nucleotide sequence of FIG. 1B, so as to thereby determine whether the nucleic acid sample is, or is derived from, a nucleic acid which encodes a mutant human Beclin.

In another example, the nucleic acid sample in step (a) comprises mRNA corresponding to the transcript of DNA encoding mutant Beclin, and wherein the determining of seep (b) comprises (i) translating the mRNA under suitable conditions to obtain an amino acid sequence; and (ii) comparing the amino acid sequence of step (i) with the above-described isolated nucleic acid which has the amino acid sequence shown in FIG. 1A so as to thereby determine whether the nucleic acid sample is, or is derived from, a nucleic acid which encodes a mutant human Beclin.

In another example, the determining of step (b) comprises (i) amplifying the nucleic acid present in the sample of step (a); and (ii) detecting the presence of the mutant human Beclin in the resulting amplified nucleic acid.

The above-described methods of determining are well-known to those skilled in the art. In an embodiment, the isolated nucleic acid or the oligonucleotide is labeled with a detectable marker, wherein the detectable marker is a radioactive isotope, a fluorophor or an enzyme.

Further, in a specific embodiment, the sample comprises blood, tissue or sera.

Further, the cancer includes, but is not limited to, ovarian, breast or prostrate cancers.

This invention also provides a method for determining whether a subject has cancer, which comprises (a) obtaining an appropriate nucleic acid sample from the subject; and (b) determining whether the nucleic acid sample from step (a) is, or is derived from, a nucleic acid which encodes a mutant human Beclin so as to thereby determine whether a subject has cancer.

Various methods of determining whether the nucleic acid sample is, or is derived from, a nucleic acid which encodes a mutant human Beclin exist.

In one example, the nucleic acid sample in step (a) comprises mRNA corresponding to the transcript of DNA encoding a mutant Beclin, and wherein the determining of step (b) comprises (i) contacting the mRNA with the above-described oligonucleotide, which is capable of specifically hybridizing with a unique sequence of nucleotides within a nucleic acid which encodes a mutant Beclin without hybridizing to any sequence of nucleotides within a nucleic acid which encodes a wildtype human Beclin, under conditions permitting binding of the mRNA to the oligonucleotide so as to form a complex, (ii) isolating the complex so formed, and (iii) identifying the mRNA in the isolated complex so as to thereby determine whether the mRNA is, or is derived from, a nucleic acid which encodes a mutant human Beclin.

In another example, the determining of step (b) comprises (i) Contacting the nucleic acid sample of step (a), and the isolated nucleic acid which encodes a wildtype human Beclin with restriction enzymes under conditions permitting the digestion of the nucleic acid sample, and the isolated nucleic acid into distinct, distinguishable pieces of nucleic acid, (ii) isolating the pieces of nucleic acid; and (iii) comparing the pieces of nucleic acid derived from the nucleic acid sample with the pieces of nucleic acid derived from the isolated nucleic acid so as to thereby determine whether the nucleic acid sample is, or is derived from, a nucleic acid which encodes a mutant human Beclin.

In another example, the determining of step (b) comprises (i) sequencing the nucleic acid sample of step (a); and (ii) comparing the nucleic acid sequence of step (i) with the above-described isolated nucleic acid having a sequence substantially the same as the nucleic acid sequence shown in FIG. 1B, so as to thereby determine whether the nucleic acid sample is, or is derived from, a nucleic acid which encodes a mutant human Beclin.

In another example, the nucleic acid sample in step (a) comprises mRNA corresponding to the transcript of DNA encoding mutant Beclin, and wherein the determining of step (b) comprises (i) translating the mRNA under suitable conditions to obtain an amino acid sequence; and (ii) comparing the amino acid sequence of step (i) with the above-described isolated nucleic acid which has the amino acid sequence shown in FIG. 1A so as to thereby determine whether the nucleic acid sample is, or is derived from, a nucleic acid which encodes a mutant human Beclin.

In another example, the determining of step (b) comprises (i) amplifying the nucleic acid present in the sample of step (a), and (ii) detecting the presence of the mutant human Beclin in the resulting amplified nucleic acid.

The above-described methods of determining are well-known to those skilled in the art. In an embodiment, the isolated nucleic acid or the oligonucleotide is labeled with a detectable marker, wherein the detectable marker is a radioactive isotope, a fluorophor or an enzyme.

Further, in a specific embodiment, the sample comprises blood, tissue or sera.

Further, the cancer includes, but is not limited to, ovarian or breast cancers.

This invention also provides for a method for inhibiting cell proliferation in cells, suppressing tumor activity or inducing autophagy by introducing the isolated nucleic acid which encodes a wildtype human Beclin into the cells, specifically wherein the cells are cancerous. Various methods of introducing nucleic acids into cells are well-known to those skilled in the art.

This invention also provides a method for treating a subject who has cancer which comprises introducing the isolated nucleic acid which encodes a wildtype human Beclin, into the subject so as to thereby treat the cancer. Various methods of Introducing nucleic acids into cells are well-known to those skilled in the art. In one example, one can introduce the isolated nucleic acid by (a) recovering cancer cells from the subject, (b) introducing the isolated nucleic acid of claim 1 into the cells; and (c) reintroducing the cells of step (b) into the subject so as to treat the subject who has cancer. Many types of cancer cells exist and are well-known in the art, specifically, breast, ovarian, skeletal, cervical, colon, prostate or lung cells.

This invention also provides a pharmaceutical composition comprising a purified wildtype human Beclin and a pharmaceutically acceptable carrier. This invention further provides a pharmaceutical composition comprising the polypeptide obtained from using the above-described method of obtaining a polypeptide in a purified form and a pharmaceutically acceptable carrier.

This invention also provides a method for treating a subject who has cancer comprising administration of an effective amount of the above-described pharmaceutical compositions to the subject who has cancer. The administration of the pharmaceutical compositions may be by topical, oral, aerosol, subcutaneous administration, infusion, intralesional, intramuscular, intraperitoneal, intratumoral, intratracheal, intravenous injection, or liposome-mediate delivery.

This invention also provides a method for detecting the presence of human chromosomal region 17q21 in a sample of genomic DNA which comprises (a) contacting the sample with the isolated nucleic acid which encodes a wildtype human Beclin, under conditions permitting formation of a complex between any genomic DNA present in the sample that is complementary to such nucleic acid, and (b) detecting the presence of any complex formed in step (a), the presence of such a complex indicating the human chromosomal region 17q21 is present in the sample. Further, one may contacting the sample with an oligonucleotide, which is capable of specifically hybridizing with a unique sequence of nucleotides within a nucleic acid which encodes a mutant Beclin without hybridizing to any sequence of nucleotides within a nucleic acid which encodes a wildtype human Beclin, under conditions permitting formation of a complex between any genomic DNA present in the sample that is complementary to such oligonucleotide, and (b) detecting the presence of any complex formed in step (a), the presence of such a complex indicating the human chromosomal region 17q21 is present in the sample. The nucleic acid may be labeled with a detectable marker, wherein the detectable marker is a radioactive isotope, a fluophor or an enzyme.

This invention also provides a method for detecting a mutant human Beclin in a subject which comprises (a) obtaining an appropriate nucleic acid sample from the subject, and (b) determining whether the nucleic acid sample from step (a) is, or is derived from, a nucleic acid which encodes mutant human beclin so as to thereby detect a mutant human Beclin in the subject.

Various methods of determining whether the nucleic acid sample is, or is derived from, a nucleic acid which encodes a mutant human Beclin exist.

In one example, the nucleic acid sample in step (a) comprises mRNA corresponding to the transcript of DNA encoding a mutant Beclin, and wherein the determining of step (b) comprises (i) contacting the mRNA with the above-described oligonucleotide, which is capable of specifically hybridizing with a unique sequence of nucleotides within a nucleic acid which encodes a mutant Beclin without hybridizing to any sequence of nucleotides within a nucleic acid which encodes a wildtype human Beclin, under conditions permitting binding of the mRNA to the oligonucleotide so as to form a complex, (ii) isolating the complex so formed, and (iii) identifying the mRNA in the isolated complex so as to thereby determine whether the mRNA is, or is derived from, a nucleic acid which encodes a mutant human Beclin.

In another example, the determining of step (b) comprises (i) contacting the nucleic acid sample of step (a), and the isolated nucleic acid which encodes a wildtype human Beclin with restriction enzymes under conditions permitting the digestion of the nucleic acid sample, and the isolated nucleic acid into distinct, distinguishable pieces of nucleic acid, (ii) isolating the pieces of nucleic acid; and (iii) comparing the pieces of nucleic acid derived from the nucleic acid sample with the pieces of nucleic acid derived from the isolated nucleic acid so as to thereby determine whether the nucleic acid sample is, or is derived from, a nucleic acid which encodes a mutant human Beclin.

In another example, the determining of step (b) comprises (i) sequencing the nucleic acid sample of step (a); and (ii) comparing the nucleic acid sequence of step (i) with the above-described isolated nucleic acid having a sequence substantially the same as the nucleic acid sequence shown in FIG. 1B, so as to thereby determine whether the nucleic acid sample is, or is derived from, a nucleic acid which encodes a mutant human Beclin.

In another example, the nucleic acid sample in step (a) comprises mRNA corresponding to the transcript of DNA encoding mutant Beclin, and wherein the determining of step (b) comprises (i) translating the mRNA under suitable conditions to obtain an amino acid sequence; and (ii) comparing the amino acid sequence of invention also provides a method for treating a subject unable to control step (i) with the above-described isolated nucleic acid which has the amino acid sequence shown in FIG. 1A so as to thereby determine whether the nucleic acid sample is, or is derived from, a nucleic acid which encodes a mutant human Beclin.

In another example, the determining of step (b) comprises (i) amplifying the nucleic acid present in the sample of step (a); and (ii) detecting the presence of the mutant human Beclin in the resulting amplified nucleic acid.

The above-described methods of determining are well-known to those skilled in the art. In an embodiment, the isolated nucleic acid or the oligonucleotide is labeled with a detectable marker, wherein the detectable marker is a radioactive isotope, a fluorophor or an enzyme.

Further, in a specific embodiment, the sample comprises blood, tissue or sera.

This apoptosis in the cells of the subject which comprises introducing the isolated nucleic acid of FIG. 1, into the subject so as to treat the subject unable to control apoptosis in the cells of the subject. In a specific embodiment, the cells are cancerous. Various method of introducing isolated nucleic acids into cells exist and are well-known in the art. In one example, one can introduce the isolated nucleic acid by (a) recovering cancer cells from the subject, (b) introducing the isolated nucleic -acid of clam 1 into the cells; and (c) reintroducing the cells of step (b) into the subject so as to treat the subject who has cancer.

This invention also provides a method of treating a subject unable to control apoptosis in the cells of the subject comprising administration of an effective amount of the above-described pharmaceutical compositions to the subject, wherein the administration comprises, topical, oral, aerosol, subcutaneous administration, infusion, intralesional, intramuscular, intraperitoneal, intratumoral, intratracheal, intravenous injection, or liposome-mediate delivery. This invention provides a method for treating a subject so as to restore cell growth control in the cells of the subject which comprises introducing the isolated nucleic acid of of FIG. 1, into the subject so as to treat the subject unable to control cell growth in the cells of the subject. In a specific embodiment, the cells are cancerous. Various method of introducing isolated nucleic acids into cells exist and are well-known in the art. In one example, one can introduce the isolated nucleic acid by (a) recovering cancer cells from the subject, (b) introducing the isolated nucleic acid of claim 1 into the cells; and (c) reintroducing the cells of step (b) into the subject so as to treat the subject who has cancer.

This invention provides a method for inhibiting viral replication in a subject comprising contacting an effective amount of Beclin with the virus infected cell, thereby inhibiting the viral replication or by inducing the expression of Beclin within the virus infected cell thereby inhibiting the viral replication.

This invention provides a method for treating a viral infection in a subject, wherein the viral infection is alleviated by the expression of Beclin comprising administration of an effective amount of a pharmaceutical composition effective to express Beclin, wherein the administering of beclin comprises (a) recovering infected cells from the subject (o) introducing the isolated beclin into the cells and (c) reintroducing the cells of step (b) into a subject sos as to treat the infected subject.

In the practice of any of the methods of the invention or preparation of any of the pharmaceutical compositions an "therapeutically effective amount" is an amount which is capable of inhibiting hairlessness or T-cell deficiency. Accordingly, the effective amount will vary with the subject being treated, as well as the condition to be treated. For the purposes of this invention, the methods of administration are to include, but are not limited to, administration cutaneously, subcutaneously, intravenously, parenterally, orally, topically, or by aerosol.

As used herein, the term "suitable pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

This invention also provides for pharmaceutical compositions capable of inhibiting neurotoxicity together with suitable diluents, preservatives, solubilizers, emulsifiers, adjuvants and/or carriers. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g.; glycerol, polyethylene glycerol), antioxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the compound, complexation with metal ions, or incorporation of the compound into or onto particulate preparations of polymeric compounds such as polylactic acid, polglycolic acid, hydrogels, etc, or onto liposomes, micro emulsions, micelles, unilamellar or multi lamellar vesicles, erythrocyte ghosts, or spheroplasts. Such compositions will influence the physical state, solubility, stability, rate of in vivo release, and rate of in vivo clearance of the compound or composition.

Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

When administered, compounds are often cleared rapidly from the circulation and may therefore elicit relatively short-lived pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

Further, in a specific embodiment, the virus comprises an RNA virus, a Sindbis virus, a mutated Sindbis virus or an influenza virus.

This invention provides a method of diagnosing a predisposition to carcinoma in a subject comprising: a) obtaining a nucleic acid sample from the subject; and b) determining whether one or more of the subject's beclin alleles or regulatory regions to those alleles are deleted or different from the wild type so as to reduce the subject's expression of polypeptide having tumor suppressor activity.

In an embodiment, a predisposition to carcinoma in a subject means that the subject based upon the diagnostic result(s) has a greater likelihood of developing a carcinoma than an otherwise similar subject lacking the diagnostic result In an embodiment, a predisposition to carcinoma in a subject means that the subject based upon the diagnostic result(s) has a greater likelihood or developing carcinoma of greater severity than an otherwise similar subject lacking the diagnostic result. One skilled in The art would recognize the statistical nature of diagnosing a predisposition to carcinoma. In an embodiment, Bayes Theorem is applied to assessing the increased likelihood of carcinoma.

Beclin allele and regulatory element differences from the wild type include, but are not limited to, deletions, additions, substitutions, and chemical modification of beclin. Chemical modifications of beclin and/or its regulatory elements include, but are not limited to, nucleotide phosphorylation, methylation, and/or hydroxylation. Sites of nucleotide differences include, but are not limited to, introns, exons, enhancers, promoters, splice junctions, splice site consensus sequences, RNA-cleavage/polyadenylation sites, cap sites, and other protein binding sites. In an embodiment, protein binding sites are located by "footprinting", wherein a protein shields the nucleic acid from cleavage by restriction enzymes.

Beclin allele or regulatory differences also include, but are not limited to, sequence changes that alter the relative distance of the beclin allele from its regulatory elements. In an embodiment, an insertion increases the distance of beclin from an enhancer. In another embodiment, a deletion, increase the proximity of beclin to its promoter.

Regulatory regions include, but are not limited to, promoters and enhancers.

This invention also provides the above-described method, wherein one or more beclin alleles contain splice site junction mutations.

This invention further provides the above-described methods, wherein There are one or more mutations in the 100 base pair region centered about the splice acceptor site consensus sequence located upstream of the exon spanning the nucleotides corresponding to positions 1042–1185 of FIG. 1B or one or more mutations in the 100 base pair region centered about the splice donor site consensus sequence located downstream of the exon spangling the nucleotides corresponding to positions 1042–1185 of FIG. 1B.

Splice site junction mutations include but are not limited to deletions, additions, and/or substitutions at or near the splice site consensus sequence. In an embodiment, the splice site consensus sequence overlaps both the adjoining intron and exon. In an embodiment, the mutations at or near the splice site consensus sequence reduce the recognition of the splice site by splicing factors. One skilled in the art would recognize that mutations in splice site consensus sequences can reduce or eliminate spicing at these locations. Further, one skilled in the art would recognize that if the wild type splice site has been mutated, the other sites may become used as solice sites with increased frequency. Further, one skilled in the art would also recognize that mutations can result in the creation of new splice sites. One skilled in the art would be able to determine from the mRNA or cDNA thereto whether the mRNA or cDNA is a product of aberrant splicing.

Primers were used to amplify exon-intron boundaries corresponding to regions of possible splice site mutations in ovarian cancer. Aberrant beclin cDNAs have been identified in ovarian tumors indicative of splice site mutations upstream or downstream of the exon spanning from 1082–1185. To facilitate identification of the genomic DNA beclin splice site mutations responsible for these mutant transcripts, two sets of primers for use in PCR amplification of relevant exon-intron boundaries were designed. These two sets of primers are:

1. Analysis of exon-intron boundaries for 1041/1042 splice site junctions:
   Foward primer (nucleotides 984–1003) of beclin) (SEQ I.D. NO:14) CCGACTTGTTCCTTACGGAA
   Reverse primer (nucleotides 1166–1147 of beclin) (SEQ I.D. NO:15) CGTGTCTCGCCTTTCTCAAC
2. Analysis of exon/intron boundaries for 1185/1186 splice site junction:
   Forward primer (nucleotides 1070–1089 of beclin) (SEQ I.D. NO:16) TGCGGTTTTTCTGGGACAAC
   Reverse primer (nucleotides 1325–1306 of beclin) (SEQ I.D. NO:17) CAAGCAAGACCCCACTTAAG In addition, this invention provides the above-described methods, wherein the determining of step b comprises determining whether one or more beclin promoter regions differ from the wild type.

One skilled in the art would recognize that mutations in beclin promoter regions may result in reduced expression of Beclin and thus reduced tumor suppressor function. Such changes would lead to a predisposition to carcinoma.

This invention provides also the above-described methods, wherein the determining of step b comprises determining whether one or more beclin promoter regions are hypermethylated.

In an embodiment, hypermethylation is associated with regions of DNA that have reduced activity or no activity. In an embodiment methylation of beclin promoter sequences is likely to reduce transciption of beclin. In an embodiment, methylation of other regions of beclin, besides the promoter, including the coding region would also be indicative of reduced Beclin activity. In an embodiment methylation of beclin or its regulatory regions occurs at CG pairs. In another embodiment, methylation of beclin or Its regulatory regions occurs at sites containing a high a frequency of CG pairs.

In an embodiment, methylation is assessed by using restriction endonucleases whose recognition sequences contain CG. For example, HpaII and MspI both recognize CCGG. However, HspII cleaves only unmethylated DNA while MspI cleaves both methylated and unmethylated DNA. Using these two restriction enzymes, one skilled in the art could infer from the size of the restriction fragments the presence of methylation. in beclin or its regulatory elements.

Further, this invention provides the above-described methods, wherein the determining of step b comprises determining whether one or more beclin enhancer regions differ from the wild type.

In an embodiment, enhancer regions may be located upstream or downstream of Beclin. In an embodiment, mutations in beclin enhancer regions would reduce Beclin production and this lead to an increased predisposition for carcinoma.

This invention further provides the above-described methods, wherein the determining of step b comprises determining whether one or more beclin 5' or 3' nontranslated regions differ from the wild type.

In an embodiment, nontranslated regions are responsible for regulating the levels of gene activity. In an embodiment, mutations in these regions would be expected to reduce Beclin production and thus lead to an increased predisposition for carcinoma.

This invention also provides the above-described methods, wherein the determining of step b comprises determining whether one or more beclin alleles have a premature termination codon.

In addition, this invention provides the above-described methods, wherein the determining of step b comprises determining whether there is a premature termination codon in the nucleic acid corresponding to positions 1180–1240 of FIG. 1B.

In an embodiment, alleles having a premature termination colon would lead to truncated products having no tumor suppressor activity or reduced tumor suppressor activity. In another embodiment, a premature termination codon between positions 1180–1240 of FIG. 1B would be expected to affect a region of Beclin that is important for Its tumor suppressor functions.

This invention also provides the above-described methods, wherein the determining of step b comprises contacting the nucleic acid sample with a primer that specifically hybridizes to the junction between the exon corresponding to positions 1042–1185 of FIG. 1B and the exon adjoining downstream thereto.

This invention also provides the above-described methods, wherein the determining of step b comprises contacting the nucleic acid sample with a primer that specifically hybridizes to the junction between the exon corresponding to positions 1042–1185 of FIG. 1B and the exon adjoining upstream thereto.

In addition, this invention provides the above-described methods, wherein the determining of step b comprises contacting the nucleic acid sample with a primer that specifically hybridizes to the junction between the exon corresponding to positions 1042–1185 of FIG. 1B and the intron adjoining downstream thereto.

This invention further provides the above-described methods, wherein the determining of step b comprises contacting the nucleic acid sample with a primer that specifically hybridizes to the junction between the exon corresponding to positions 1042–1185 of FIG. 1B and the intron adjoining upstream thereto.

In an embodiment, a primer that specifically hybridizes to The junction between the exon corresponding to positions 1042–1185 of FIG. 1B and the adjoining downstream or upstream exon would exhibit reduced hybridization if there was a mutation in this region. Such reduced hybridization would be diagnostic of a splice site mutation in this region.

In an embodiment, a primer that specifically hybridizes to the junction between the exon corresponding to positions 1042–1185 of FIG. 1B and the adjoining downstream or upstream intron would exhibit reduced hybridization if there was & mutation in this region. Such reduced hybridization would be diagnostic of a splice site mutation in this region.

This invention also provides the above-described methods, wherein a majority of the nucleotides corresponding to positions 1042–1185 of FIG. 1B have been deleted.

Further, this invention provides the above-described methods, wherein the subject was preselected based upon an abnormality at chromosome position 17q21.

This invention also provides the above-described methods, wherein the abnormality at chromosome position 17q21 comprises a deletion.

Abnormalities at chromosome position 17q21 may be detected by numerous methodologies which include, but are not limited to, karyotyping and in situ hybridization.

This invention also provides the above-described methods, wherein the nucleic acid sample is obtained from the subject's blood.

Nucleic acid samples can be obtained from numerous sources which include, but are not limited to, blood, saliva, tissue, and hair follicles.

This invention further provides a method of diagnosing a predisposition to carcinoma in a subject, comprising determining whether the subject has an abnormal subcellular distribution of Beclin.

This invention also provides the above-described methods, wherein the abnormal subcellular distribution of Beclin comprises Beclin being distributed diffusely in both the nucleus and cytoplasm.

In addition, this invention provides a method of diagnosing a predisposition to carcinoma in a subject, comprising contacting the contents of one or more of the subject's cells with one or more antibodies or fragments thereof specific to Beclin.

Further, this invention provides the above-described methods, wherein one or more of the antibodies is the antibody with designation number 843 and one or more of the antibodies is the antibody with designation number 844.

This invention also provides the above-described methods, wherein the antibody's failure to bind to Beclin indicates that the subject has a predisposition to carcinoma.

In an embodiment, the antibodies are monoclonal. In another embodiment, the antibodies are polyclonal. On skilled in the art would also recognize that fragments of antibodies are suitable for binding to antigen. In yet another embodiment, the antibodies are labeled. Methods of labeling antibodies include, but are not limited to, fluorescence, radioactivity, and enzymatic assays. In an embodiment, the antibody is linked to an enzyme that catalyzes a reaction leading directly or indirectly to a detectable product.

In an embodiment, Western blotting using an antibody to Beclin is used to detect Beclin. In an embodiment, the failure of the antibody to bind to Beclin indicates that Beclin is absent. In another embodiment, the failure of the antibody to bind to Beclin indicates that Beclin is truncated or altered at the region recognized by the antibody. In a further embodiment, two or more antibodies are used that recognize different epitopes of Beclin so as to distinguish between the truncation or alteration of Beclin at or near an epitope and the absence of Beclin. In an embodiment, the complete failure of Beclin to be detected by Western blotting is diagnostic of an increased risk of carcinoma.

Two synthetic peptides were synthesized corresponding to amino acids 1–15 of human Beclin (SEQ I.D. NO.:18) (MEGSKTSNNSTMQV) and amino acids 374–389 of human Beclin (SEQ. I.D. NO.:19) (CVQQFKEEVEKGETRF). Polyclonal antibodies to these two peptides, named 843 and 844 were produced by rabbit immunizations with peptide linked to KLH carrier. 843 exhibits strong immunoreactivity with the Beclin peptide amino acids 1–15 in ELISA and 844 demonstrates strong immunoreactivity wish the Beclin peptide amino acids 374–389. In addition, 843 reacts with full-length wild-type and mutant Beclin proteins by Western blot analysis and by immunohistochemical staining of normal and malignant human breast and ovarian tissues. To date Beclin immunoreactivity using 843 has been demonstrated to be present in normal, breat epithelial cells, normal ovarian epithelial cells, vascular smooth muscle cells, skeletal muscle cells, and neurons. Approximately 50% of sporadic invasive breast and ovarian cancer cases have tumor epithelial cell staining for Beclin with 843 and approximately half of these cases have no tumor epithelial staining with 843. Studies are in progress to determine whether 844 also reacts with Beclin protein in Western blot and immunohistochemical analyses.

843 1s useful to detect total Beclin protein expression in human cells and human tissue by Western blot or immunocytochemical analysis. Because loss of Beclin protein expression is likely to be important in breast, ovarian, and prostate tumorigenesis, this antibody would be useful to detect susceptibility to these cancers.

844 would be useful to distinguish normal Beclin protein expression from mutant Beclin protein expression where the mutant Beclin protein contains a deletion of amino acids 374–389. Such mutant Beclin proteins are predicted to occur in ovarian cancer, on the basis of translation of mutant cDNA beclin sequences found in these tumors. Therefore, it is predicted that antibody 844 cannot react with mutant Beclin proteins made from mutant cDNA sequences found in ovarian cancer cases. Thus, the presence of Beclin protein that reacts with 843 but not 844 by either Western blot or immunohistochemical analysis would be diagnostic of the presence of a mutant Beclin protein lacking amino acids 374–389 of wild-type Beclin protein.

In embodiments, this invention provides the above-described methods, wherein the carcinoma is breast cancer, ovary cancer, and/or prostate cancer. Other carcinomas may also be diagnosed including, but not limited to, skin, colon, rectal, lung, breast, stomach, liver, uterine, bladder, and prostate cancers.

This invention is illustrated in the Experimental Details section which follows. This section is set forth to aid in understanding the invention but is not intended to, and should not be construed to, limit in any way the invention as set forth in the claims which follow thereafter.

EXPERIMENTAL DETAILS

FIRST SERIES OF EXPERIMENTS

Cell proliferation and apoptosis may share common pathways. Yet, in death repressor pathways, no direct links have been identified between cellular genes that inhibit apoptosis and cellular genes that inhibit proliferation. To investigate the mechanism by which anti-apoptotic genes function, the yeast two hybrid system was used to screen an adult mouse brain cDNA library for genes encoding proteins that interact with Bcl-2. Both Bcl-2 and its related family member, Bcl-x, interact with a novel 60 kd protein, Beclin, encoded by a gene on a specific region of chromosome 17q21 that is postulated to contain a tumor suppressor gene important in sporadic breast and ovarian cancer. Loss of function mutations in the conserved BH1 domains of Bcl-2 and Bcl-$x_L$ disrupt binding with Beclin, and antisense beclin blocks the ability of bcl-2 to protect cells from Sindbis virus-induced apoptosis. Furthermore, beclin overexpression inhibits the proliferation of rat prostate adenocarcinoma AT3 cells and mouse NIH 3T3 fibroblast cells as well as the formation of human MCF7 breast tumor in nude mice. Together, these finds suggest that beclin is a novel bcl-2-interacting, candidate tumor suppressor gene that may link regulation of cellular proliferation with death repressor pathways.

The common deletion unit, located approximately 60 kb centromeric to BRCA1 that is postulated to contain an additional tumor suppressor gene important for ovarian and possibly breast cancer, contains 12 previously identified genes (Friedman, et al., 1995). Six of them are known genes or human homologs of other species, gamma tubulin, homolog of *D. melanogaster* enhancer of zeste, pseudogene of HMG17, homolog of Pacific electric ray VAT1, glucose-6phosphatase and Ki antigen. The remaining six genes are novel genes, one of which is the gene referred to as beclin that is described in this invention.

The mapping of beclin to this common deletion unit on chromosome 17q21, coupled with data that Beclin interacts with Bcl-2 and has anti-proliferative effects, raises the possibility that Beclin may function as a tumor suppressor gene important in ovarian and breast cancer.

Example 1

Yeast Two Hybrid cDNA Library Screen To Isolate Bcl-2-interacting Proteins. To further understand the mechanism by which bcl-2 protects against apoptosis, the yeast two hybrid system was used to screen a mouse brain library for complementary cDNAs encoding proteins that bind to Bcl-2. A bait plasmid (pGBT9/bcl-2) was constructed by fusing human bcl-2 (lacking the C' terminal signal-anchor sequence to ensure translocation to the nucleus) to the GAL4 DNA-binding domain, which was cotransformed with an oligo (dT) and random hexamer primed adult mouse brain cDNA fusion library in a GAL4-activating domain vector, pGAD10. pGBT9/bcl-2 was co-transformed with $1 \times 10^6$ cDNAs from a mouse brain library fused to a GAL-4 activation domain vector (Clontech), plated onto SD medium lacking tryptophan and leucine, and after incubation at 30° C. for 4 days, screened for LacZ activity using a colony lift filter assay. Putative interacting clones were isolated by manipulation in leuB *E. Coli*, and further tested against pGBT9 and control plasmids. Of one million transformants, one true positive colony (F1) was identified by the X-Gal filter assay. A positive β-gal reaction between pGBT9/bcl-2 and clone F1 was obtained within 15–20 minutes. The sequence of the Eco RI insert in clone F1 was obtained using Sequenase and by automated dideoxy sequencing. Sequencing analysis of the cDNA plasmid rescued from this colony revealed a termination codon 42 base pairs downstream from the GAL 4 activation domain, several predicted short open reading frames between nucleotides 124 and 1843, and a longer predicted open reading frame spanning from nucleotide 1855 to 2500(the 3' end of the insert), suggesting that either the 14 amino acid fusion protein was interacting with Bcl-2, or one of the downstream open reading frames encoded a protein that contains its own activation domain and interacts with Bcl-2. To identify the Bcl-2-interacting region of F1, nucleotides 1–1854 and 1855–2500 were fused to the GAL4 activation domain in pGAD424 and tested for interactions with Bcl-2. Nucleotides 1855–2500, but not 1–1800, encoded a protein that specifically interacts which Bcl-2 (Table 1) but not with control GAL4 DNA binding domain plasmids containing p53, lamin (Table 1) or Sindbis virus glycoproteins.

A database search revealed that the sequence of F1:1855–2500 overlapped with several clones isolated from a normalized infant human brain cDNA library in the Merck EST database as well as clones from human breast (GT197) (Rommens, 1995) and human fibroblast cells (B32) (Friedman, 1994). Clones GT197 and B32 were both isolated in the generation of transcription maps of the breast cancer susceptibilty locus on chromosome 17q21 and are mapped to a region located approximately 100 kilobases centromeric to the gene BRCA1. They lie within a 400 kb deletion unit mapped in sporadic ovarian cancers that contains 12 genes, including six genes with known function and six novel genes (Tangir, J., et al., 1996). This minimal deletion unit centromeric to BRCA1 is postulated to contain a tumor suppressor gene important for sporadic breast and ovarian cancer. These clones contain only partial open reading frames of a novel gene that encodes a protein with coiled coils. The gene was assigned the name beclin, because of the interaction of its encoded protein with bcl-2 (becl) and the predicted coiled coil structure of its encoded protein (in suffix).

The overlapping partial clones in Genbank were aligned with the mouse beclin sequence to obtain a predicted sequence of the full-length open reading frame for human beclin. Human beclin was isolated from a normalized human brain infant cDNA library (Soares, 1994). Human Beclin is homologous with the *C. elegans* T19E7.3 gene product (GENBANK accession U42843) and the *S. cerevisiae* gene product Lph7p (GENBANK accession U43503) (38% and 37% identical ove 145 and 137 residues, respectively), indicating a high degree of evolutionary conservation.

TABLE 1

Summary of yeast two-hybrid assay results

| | GAL4 BD | | | | | | |
|---|---|---|---|---|---|---|---|
| GAL4 AD | Empty | Bcl-2 | Bcl-$X_L$ | Bcl-$X_S$ | Bax | Lamin | p53 |
| Empty | − | − | − | + | − | − | − |
| F1 | − | + | + | ND | − | − | − |
| F1:2-1855 | − | − | − | ND | − | − | − |
| F1:1956-2563 (Mus Beclin 1-708) | − | + | + | ND | − | − | − |
| Hu Beclin 1-708 | − | + | + | ND | − | − | − |
| Hu Beclin 1-450 | − | + | + | ND | − | − | − |
| Hu Beclin 1-258 | − | − | − | ND | − | − | − |
| Hu Beclin 262-450 | − | + | + | ND | − | − | − |
| Hu Beclin 451-708 | − | − | − | ND | − | − | − |
| Hu Beclin 1-1353 | − | − | − | ND | − | − | − |

The sequences encoding amino acids 1–218 of human bcl-2, 1–212 of bcl-$x_L$, 1–149 of bcl-$x_S$, and 1–171 of bax were cloned into pGBT9 in frame with the GAL4-binding domain. To avoid problems with targeting or proteins to the nucleus, the sequence encoding C' terminal transmembrane domains were omitted. To construct pGBT9/bcl-2, human bcl-2 was amplified by PCR from the plasmid pZIP/bcl-2, subcloned into pCR$^{TMII}$, and the correct sequence of bcl-2 was confirmed prior to cloning an EcoR I-Sal I fragment into pGBt9. To construct pGBT9/bcl-$x_L$, pGBT9/bcl-$x_S$, and pGBT9/bax, the EcoR I-Xho I fragment were excised from pGEG202 plasmids previously described and cloned into the Eco RI—Sal I sites of pGBT9. Control pB=GBT9 plasmids containing lamin (pLAM 5') and P53 (ppVA3) inserts were obtained from Clontech. pGBT9/bcl-2 was co-transformed with 1×10$^6$ cDNAs from a mouse brain library fused to a GAL-4 activation domain vector (Clontech), plated onto SD medium lacking tryptophan and leucine, and after incubation at 30° C. for 4 days, screened for LacZ activity using a colony lift filter assay. Putative interacting clones were isolated by manipulation in leu3 E. Coli, and further tested against pGBT9 and control plasmids. A positive B-gal reaction between pGBT9/bcl-2 and clone was obtained using Sequence and by automated dideoxy sequencing. Additional clones containing fragments of F1 or human beclin fused to the GAL4-activation domain were constructed using PCR primers which incorporated Eco RI and Sal I restriction sites into the forward and reverse primers, respectively.

Additional yeast two hybrid studies were performed to confirm that beclin, like mouse beclin, encodes a protein that interacts with human Bcl-2, and to further define the Bcl-2-interacting region of human Beclin (see Table 1). Additional clones containing fragments of F1 or human beclin fused to the GAL4-activation domain were constructed using PCR primers which incorporated Eco Ri and Sal I restriction sites into the forward and reverse primers, respectively.

Sequencing Of Human Beclin. Primers immediately upstream and downstream of the predicted open reading frame were used to amplify the coding sequence of human beclin from a normalized human infant brain cDNA library (Soares, 1994). The resulting PCR products from several independent reactions were cloned into pCR$^{TMII}$ and sequenced in both directions using Sequenase (US Biochemicals) as well as automated sequencing. The resulting nucleotide sequence (FIG. 1B) and deduced amino acid sequence (FIG. 1A) were used to scan various data banks (Genbank, EMBL, SwissProt, PIR) for homologous sequences using the BLAST algorithms (Altschul, 1990). The amino acid sequence was also analyzed by the PROS-TTE program to identify functional motifs and by the COILS program to identify coiled coil regions (Lupas, 1991).

Yeast Two Hybrid Analyses of Beclin-Bcl-2 Family Member Interactions. To investigate whether Beclin interacts with other Bcl-2 family members that positively or negatively regulate apoptosis, bax, bcl-$x_S$ and bcl-$x_L$ cDNAs were fused into the GAL4 binding domain vector and tested for interactions with Beclin in the yeast two hybrid system. (See Table 1).

The sequences encoding amino acids 1–218 of human bcl-2, 1–212 of bcl-$x_L$, 1–149 of bcl-$x_S$, and 1–171 of bax were cloned into oGBT9 in frame with the GAL4-binding domain. To avoid problems with targeting of proteins to the nucleus, the sequences encoding C'terminal transmembrane domains were omitted. To construct pGBT9/bcl-2, human bcl-2 was amplified by PCR from the plasmid pZIP/bcl-2, subcloned into pCR$^{TMII}$, and the correct sequence of bcl-2 was confirmed prior to cloning an Eco RI-Sal I fragment into pGBT9. To construct pGBT9/bcl-$x_L$, pGBT9/bcl-$x_S$, and pGBT6/Bax, the Eco RI—Xho I fragments were excised from pGEG202 plasmids previously described (Sato, et al., 1994) and cloned into the Eco RI—Sal I sites of pGBT9. Control pGBT9 plasmids containing lamin (pLAM5') and p53 (pVA3) inserts were obtained from Clontech.

The Bcl-$x_S$ GAL4 DB construct activated transcription by itself, and therefore could not be tested for interactions with Beclin. The same region of Beclin (aa 88–150) that interacted with Bcl-2, also interacted with Bcl-$x_L$ (Boise, 1993), a related Bcl-2 family member that inhibits apoptosis. In contrast, Beclin did not react with Bax (Oltvai, 1993), a family member that promotes apoptosis. The selective interaction of Beclin with Bcl-2 family members that have death repressor activity suggests a possible functional role of Beclin in anti-apoptotic pathways.

Full-length human Beclin does not interact with Bcl-2 in the yeast two-hybrid system. This most likely reflects lack of translocation to the nucleus in yeast secondary to association with yeast intracellular membranes since full-length human Beclin expressed in mammalian cells is associated with the insoluble membrane fraction after cell lysis.

To evaluate whether Bcl-2-Beclin and Bcl-$x_L$-Beclin interactions are related to the ability of Bcl-2 and Bcl-$x_L$ to inhibit apoptosis, pGBT9 vectors were constructed containing bcl-2 and bcl-$x_L$ constructs with mutations in the conserved BH1 domain that are known to block death repressor activity. A G→A mutation at amino acid position 145 of Bcl-2 completely abrogates Bcl-2 death-repressor activity in Interleukin-3 deprivation, γ-irradiation and glucocorticoid-induced apoptosis (Yin, 1994), and also blocks Bcl-2 binding to beclin in the yeast two hybrid system (Table 2). Similarly, substitutions of amino acids 136–138 of Bcl-$x_L$ (VNW→AIL) completely abolishes death repressor activity in Sindbis virus-induced apoptosis (Cheng, 1996), and also blocks Bcl-$x_L$ binding to Beclin. Thus, mutations that block anti-death activity of bcl-2 and bcl-$x_L$ also block binding to beclin.

TABLE 2

Effect of BH1 domain mutations on the ability of Bcl-2 and Bcl-$x_L$ to bind to beclin in the yeast two-hybrid assay

|  |  |  | Inhibition of Apoptosis | Beclin Binding |
|---|---|---|---|---|
| WT BCL-2 | (SEQ I.D. NO.:20) | ELFRDGVNWGRIVAFFEFGG | + | + |
| WT BCL-$X_L$ | (SEQ I.D. NO.:21) | ELFRDGVNWGRIVAFFSFGG | + | + |
| MT BCL-2 | (SEQ I.D. NO.:22) | ---------A---------- | − | − |
| MT BCL-$X_L$ | (SEQ I.D. NO.:23) | ------AIL----------- | − | − |

Oligonucleotide-directed mutagenesis of bcl-2 and bcl-$x_L$ was accomplished by a two-step polymerase chain reaction. Mutants were cloned into pCR$^{TMII}$ (In Vitrogen) and mutations were confirmed by dideoxy sequencing prior to cloning into pGBT9. PGBT9/bcl-2 and pGBT0/bcl-$x_L$ mutants were cotransformed with fragments of human beclin (1–450, 262–450, 1–708) fused to the GAL4-activation domain. Transformants were screened by B-galactosidase assays to determine whether mutations affected Beclin binding.

Analysis Of Beclin Expression In Mammalian Cells. Human beclin is predicted to encode a novel 450 amino acid protein, containing a coiled coil region with 25–28% homology with myosin-like proteins (FIG. 1A). Western blot analysis of lysates prepared from BHK cells infected with a Sindbis virus vector that expresses flag epitope-tagged Beclin confirms that human beclin encodes a 60 kd protein (FIG. 2A).

To construct the plasmid SIN/flag-beclin, human beclin was amplified by PCR from a human brain cDNA library, using primers that incorporated upstream and downstream Bst EII sites and an upstream sequence encoding the flag epitope. The Bst EII flag-beclin fragment was ligated into the Bst EII restriction site of the previously described double subgenomic SIN vector, ds633. Recombinant virus stocks were generated from SIN/flag-beclin plasmid as described. BHK cells were infected with SIN/flag-beclin or control constructs at a multiplicity of infection (MOI) of 1 plaque-forming unit per cell and harvested 15 hours after infection.

PROSITE analysis of human beclin identified several potential phosphorylation and myristoylation sites, but no other functional sequence motifs. RNA blot analysis revealed that expression of beclin mRNA is widespread in both mouse and human adult tissues. A beclin-specific probe hybridized to a 2.3 kb transcript present at highest levels in human skeletal muscle, but at detectable levels in all tissues examined (FIG. 2B). In some tissues, additional 1.7 and 1.4 kb transcripts were observed, suggesting the presence of alternately spliced transcripts.

To examine the subcellular localization of Beclin in mammalian cells and to determine whether Beclin colocalizes with Bcl-2, baby hamster kidney cells were transmitted with the plasmids, pSG5/bcl-2 and pSC-5/beclin, that express Bcl-2 and a flag-epitope tagged Beclin, respectively. Immunofluorescence staining with an anti-flag epitope antibody and an anti-Bcl-2 antibody revealed that both proteins were expressed in the perinuclear membrane/endoplasmic reticulum region (FIG. 2C). Confocal laser microscopic analysis of BHK cells cc-transfected with flag-epitope-tagged Beclin and Bcl-2 revealed that Beclin (FIG. 2D), like BCL-2 (FIG. 2C), displays a punctate pattern of immunoreactivity that is characteristic of association with intracellular organelles. Thus, Bcl-2 and Beclin colocalize in transfected mammalian cells.

Beclin's Ability To Interact With Bcl-2. When expressed in transient transfection assays, flag-tagged full-length human Beclin displays punctate immunoreactivity pattern suggestive of association with Intracellular organelles and is associated with the insoluble fraction after cell lysis. In contrast, a flag-tagged truncated Beclin (a.a. 1–236) (corresponding to the region isolated in the yeast two hybrid screen) displays a diffuse cytoplasmic staining pattern and is soluble after cell lysis (Liang and Levine, unpublished data). These differences between full-length and truncated Beclin are thought to account for differences in ability to translocate to yeast nuclei and interact with Bcl-2 in the yeast two hybrid assay.

The ability of human Beclin to bind to Bcl-2 in the yeast two-cybrid system maps to amino acids 88–150 (nucleotides 262–50). Interestingly, the coding sequence for this region of Beclin is deleted in some human infant brain cDNA clones in the Merck EST database, suggesting that Beclin exists in at least two forms-including one form that contains a Bcl-2 binding domain and one form that lacks a Bcl-2 binding domain.

To examine whether a full-length human Beclin interacts with Bcl-2 in mammalian cells, a fluorescence resonance energy transfer (FRET) studies of COS cells co-transfected with Bcl-2 and flag epitope-tagged Beclin was performed. Beclin is a coiled colled protein that may be associated with the cytoskeleton and it partitions with the insoluble fraction following cell lysis. For this technical reason, biochemical analyses of in vivo interactions between Bcl-2 and Beclin are difficult to perform. FRET is a flurorescence technique which can be used as a spectroscopic ruler to study and quantify the interactions of cellular components with each other (Stryer, L., 1978; Wu, P. and Brand, L., 1994; Wang, S. F., et al., 1993; Selvin, P. R., 1995; Gadella, T. W., 1994). In FRET, a fluorophor (donor) in an excited state may transfer its excitation energy to a neighboring chromophor (acceptor) nonradiatively through dipole-dipole interactions. The efficiency of this process varies most importantly as the inverse of the sixth power of the distance separating the donor and acceptor chromophores, and in practice, requires the distance between the donor and the acceptor flurophores to be close (usually not exceeding 50 Angstroms). The dependence of the energy transfer efficiency on the donor-acceptor separation provides the basis for the utility of this phenomenon in the study of cell component interactions. FRET has been used by a number of investigators to examine interactions of cellular constituents (reviewed in Stryer, L., 1978; Wu, P. and Braid, L., 1994; WAng, S. F., et al., 1993; Selvin, P. R., 1995; Gadella, T. W., 1994) such as endosomal fusion events, ligand-dependent growth factor receptor aggregations, interactions of viral and cellular proteins with regulators of apoptosis (Liang, X. H., et al., 1994; Mahajan, N., et al., 1996; Herman, B., et al., 1997), and interactions of cellular cytoskeletal components (Root, D., 1997).

FRET can be detected by exciting the labeled specimen with light of wavelengths corresponding to the absorption spectrum of the donor and then detecting light emitted at the wavelengths corresponding to the emission spectrum of the acceptor. FRET manifests itself by both quenching of donor fluorescence in the presence of acceptor and in sensitized emission of acceptor fluorescence. FRET microscopy was performed as described herein. The donor (FITC) filter set consisted of excitation (ex)=450–490 nm; dichroic mirror (dm)=510 nm; emission (em)=515–555 nM. The acceptor (Rhodamine) filter set consisted of [ex=546 nm; dm=580 nm; long pass]. Images obtained with these two filter sets were used to directly quantify the intensities of each fluorophore. The FRET filter set consisted of [ex=450–490 nm; dm–580 nm; em=580 long pass]. The signal recorded from this filter set is the FRET signal and is from energy that has transferred from FITC to Rhodamine molecules. A background image containing no cells was taken with each filter set and subtracted from images with cells. A mapping program written in house was used to map fluorescent cells and to quantify the intensity within each cell. Quantitative analysis of these mapped images required solving three equations, one for each filter set, which accounted for the excitation and detection of both labels in all three filter sets as well as the concentrations of the donor and acceptor molecules and the probability of energy transfer. The measured quantities are expressed as follows in which the first letter (upper case) indicates the filter set (A=acceptor, F=FRET; D=donor) and the second letter (lower case) indicates the labels preset (a=acceptor alone; f=acceptor and donor; d=donor alone). A solution of the equations is E=1/[aconc(RK=1)] where aconc=(AdFf–FdAf)/[(AdFa/Aa)–Fd]; R=(DaFf/Fa–Df/[aconc ((Fa/Aa)–FdDa/DdAa)–Ff+FdDf/Dd]; and K is proportional to the product of the ratio of the quantum yield of the two labels and the ratio of the absolute detection efficiencies of the two labels.

Flag epiope-taged Beclin was labled with donor fluorophor (FITC) and Bcl-2 was labeled with acceptor fluorophor (Rhodamine) (FIGS. 3A–I). As a control, the endoplasmic reticulum $Ca^2$+ATPases (SERCA) with donor (FITC) and Bcl-2 with acceptor (Rhodamine) were used. Quantitative analysis of microscopic images (following corrections for cross-talk between filler sets and donor and acceptor concentrations) showed significantly more energy transfer in experimental cells with labeled Beclin and Bcl-2 than in control cells with labeled SERCA and Bcl-2. (The quantitative measure of FRET used is a value, E, proportional to he probability of energy transfer between any donor molecule and any acceptor molecule). For the experimental cells, $E_{beclin-Bcl-2}$=0.00325±0.00153 (N=410) and for the control cells, $E_{SERCA-Bcl-2}$=0.00065±0.00043 (N=775) (p=<0.0001; t test). These data demonstrate that Beclin and Bcl-2 exhibited FRET, providing evidence of an interaction between these two proteins in mammalian cells.

Role Of Beclin In Virus-Induced Apoptosis. Overexpression of many Bcl-2 family members (Boise, 1993; Oltvai, 1993) or Bcl-2 interacting proteins (Farrow, Takayama) results in either the acceleration or inhibition of apoptosis. The Sindbis virus vector system was employed, which has been previously used to study the anti-apoptotic function of several Bcl-2 family members (Cheng, 1996), to evaluate the effects of beclin overexpression on virus-induced apoptosis. This system uses Sindbis virus both as an inducer of apoptosis and as a vector, and provides a means of rapidly testing the ability of candidate death-regulatory genes to suppress or accelerate virus-induced apoptosis (Cheng, E. H., et al., 1996); Levine, B., et al., 1996). Chimeric recombinant Sindbis viruses were constructed that contain human beclin or bcl-2 inserts in the sense and antisense orientations. Bcl-2 expressed from the recombinant Sinabis virus delayed death in BHK cells, as indicated by 50% cell viability compared to 0% with control viruses at 30 hours post-infection. However, neither Beclin nor antisense beclin expressed from recombinant viruses delayed or accelerated virus-induced death (FIG. 4A). While Bcl-2 overexpression results in a significant delay in SIN-induced cell death of BHK cells, neither antisense beclin RNA nor beclin overexpression delays or accelerates virus-induced death. Therefore, rather than acting as an independent regulator of apoptosis, Beclin may be a functional component of a pathway that is mechanistically involved in the death repressor activity of Bcl-2.

Role Of Beclin In Cellular Proliferation. To test this hypothesis, Beclin was tested to see if it plays a role in the ability of Bcl-2 to inhibit virus-induced apoptosis in mammalian cells. A bcl-2-transfected rat prostate adenocarcinoma cell Line (AT3/bcl-2 cells) that is resistant to Sindbis virus-induced apoptosis (Levine, 1996, was infected with chimeric Sindbis viruses containing beclin in either the sense or antisense orientation.

To construct the plasmid SIN/flag-beclin, human beclin was amplified by PCR from a human brain cDNA library, using primers that incorporated upstream and downstream Bst EII sites and an upstream sequence encoding the flag epitope. The Bst EII flag-beclin fragment was ligated into the Bst EI restriction site of the previously described double subgenomic SIN vector, ds633, and recombinant virus stocks were generated from SIN/flag-beclin plasmid as described. The recombinant chimeric viruses SIN/antisense bcl-2 SIN/antisense beclin were constructed using identical methods. The construction of SIN/CAT has been described previously.

At 72 hours after infection, 77% of cells infected with SIN/beclin and 66% of cells infected with a control chimeric virus, SIN/CAT were still alive (FIG. 4B) In contrast, only 35% of cells infected with SIN/antisense beclin were still alive. The magnitude of this increase in cell death is similar to that seen after infection with a virus containing bcl-2 antisense RNA. The ability of antisense beclin, like antisense bcl-2, to partially inhibit bcl-2 protection against Sindbis virus-induced apoptosis demonstrates a functional role for Beclin in the death repressor activity of Bcl-2.

In the course of the above experiments, an apparent inhibition of cellular proliferation in both BHK cells and AT3/bcl-2 cells infected with SIN/beclin was observed. The number of AT3/bcl-2 cells 24 hours after infection with SIN/beclin was reduced by more than 50% as compared to the number of AT3/bcl-2 cells that were mock-infected or infected with SIN/CAT (FIG. 5A), whereas no significant differences were observed in AT3/bcl-2 cell viability among the three groups (FIG. 5B). A similar antiproliferative effect of beclin was observed in control AT3/neo cells, although these cells die quickly after infection with SIN/beclin and it is difficult to accurately quantitate cell proliferation in the face of rapid cell death.

These findings were confirmed in AT3 cells using a different experimental system, mouse fibroblast NIH 3T3 cell lines that conditionally express beclin or antisense beclin, using tetracycline-repressible expression vector.

The vectors were made by amplifying a full length human beclin from a human brain cDNA library (Soares, M. B., 1994) using PCR primers which incorporated Nhe I resriction sites, and cloned into the Nhe I cloning sites of the conditional expression vector, BC252SV40 (provided by Axel Pollack, GSF-Institut fur Klinische Molekularbiologie). BC252SV40 consists of pHEBO, an EBV-derived promoter (TP1) in which the EBNA2 binding site was replaced by the tet07 element and an expression cassette for the tTA transactivator under the control of a CMV promoter, and a hygromycin selection marker. tTA binds to tet07 in the absence of tetracycline, but not in its presence, and induced the transcription of genes under control of tet07. The plasmids BC252SV40, BC252SV40/beclin, and BC252SV40/antisense beclin were transfected into NIH 3T3 cells using PFX6 (inVitrogen) according to the manufacturer's instructions, and stable transfectants were selected for with 300 µg/ml hygromycin and maintained in 1 µg/ml tetracycline. Antisense beclin-transfected clones were screed for inducible antisense flag-beclin mRNA expression by performing RT-PCR in the presence and absence of tetracycline, using forward primer that hybridizes with the nucleotide sequence encoding the flag epitope tag and a reverse primer corresponding to nucleotides 746–765 of human beclin. Beclin-transfected clones were screened for inducible flag-beclin mRNA expression by RT-PCR and flag-Beclin protein expression by performing immunoblot analysis with an anti-flag M2 antibody (20 µg/ml) using previously described methods (Liang, X. H., 1995).

A tetracycline-responsive NIH 3T3 clone stably transfected with antisense beclin and a control NIH 3T3 clone transfected with an empty vector were infected with recombinant chimeric Sindbis viruses that express either wild-type Bcl-2 (SIN/bcl-2) or Bcl-2 containing a stop codon near the 5' terminus (SIN/bcl-2 stop) (FIG. 4C) In the presence of tetracycline (when antisense beclin expression is suppressed) protection against virus-induced death was observed in both SIN/bcl-2 infected NIH/antisense beclin cells as well as in control cells. However, in the absence of tetracycline (when antisense beclin is expressed), no protection against Sindbis virus-induced death was conferred by bcl-2 in NIH 3T3/antisense beclin cells. Thus, similar to the observation in AT3 cells, antisense beclin expression also blocks the death repressor activity of bcl-2 in NIH 3T3 cells.

Cell proliferation of tetracycline-responsive NIH 3T3/beclin and NIH 3T3 antisense beclin clones and NIH 3T3 control transfectants in the presence or absence of tetracycline was measured (FIG. 5C). Tetracycline had no effect on the proliferation of control NIH 3T3 cells transfected with empty vector. In the presence of tetracycline, NIH 3T3/beclin cells and NIH 3T3/antisense beclin cells proliferated at the same rate as control transfectants. However, when tetracycline was removed from the culture medium, the rate of cell growth was significantly delayed in beclin-expressing cells and conversely, was accelerated in antisense beclin-expressing cells. These data demonstrate a role for beclin in the regulation of NIH 3T3 cell growth.

In view of genetic data suggesting that chromosome 17q21 contains a second tumor suppressor gene (in addition to BRCA1) important in sporadic breast and ovarian cancer (reviewed in Tangir, J., er al., 1996; Vogelstein, B., et al., 1994), the effect of beclin gene transfer on human MCF7 breast carcinoma cells was evaluated. Wild-type MCF7 cells (which are derived from a tumor containing 17q21 LOH) (Holt, J. T., et al., 1996) were transfected with the BC252SV40 expression vector containing wild-type Beclin and hygromycin-resistant clones were selected. As expected after transfection with a gene that may negatively regulate cell growth, in several independent transfections, very few hygromycin-resistant colonies were obtained that grew beyond 10–20 cells and which could be tested for gene expression. Among five hygromycin-resistant colonies that could be expanded, four had flag-Beclin message RNA detectable by RT-PCR but only one of these clones had detectable flag-Beclin expression by Western blot analysis (clone 17) (FIG. 6A). The tetracycline-regulatable expression vector, BC2525V40 previously described was used for MCF7 transfections with beclin. However, no tetracycline-responsive hygromycin resistant MCF7 Beclin clones were obtained; result are presented using MCF7 Beclin clone 17 which constitutively expresses flag-Beclin. This clone was chosen for further analysis.

Morphologic changes suggestive of a less transformed phenotype were observed in: MCF7 cells that express Beclin. Whereas control cells were small, retractile, and often rounded (FIG. 6B), MCF7 Beclin cells were significantly larger, more flat in appearance and more firmly attached to the tissue culture plate (FIG. 6C) Control cells grew. to a higher density (FIG. 6B), while cells that expressed Beclin were contact-inhibited and grew as a monolayer in culture (FIG. 6C).

Similar morphologic changes were observed in many MCF7 colonies obtained after transfection with BC2525V40/beclin which could never be expanded for analysis of gene expression and further investigations, but not in MCF7 colonies obtained after transfection with the empty BC2525V40 vector.

To further evaluate anchorage-independent growth, the ability of MCF7 Beclin 17 and MCF7 control 5 clones to form colonies in soft agar was examined (see Table 3). Whereas MCF7 Beclin 17 cells were unable to form colonies In soft agar, the number c(f colonies formed by MCF7 control 5 cells averaged over 1100 per 5×104 cells plated.

TABLE 3

Effect of beclin transfection on MCF7 colony formation in soft agar and tumorigenicity in nude mice.

| Clone | # colonies ± s.e. | # mice w/ tumors/# mice injected | mean tumor volume (mm$^3$) ± s.e. | mean tumor weight (mg) ± s.e. |
|---|---|---|---|---|
| MCF7 Beclin 17 | 0 ± 0 | 2/14* | 92 ± 17** | 80 ± 0** |
| MCF7 control 5 | 1047 ± 189 | 8/9 | 375 ± 135 | 360 ± 200 |
| MCF7 control 7 | ND | 6/8 | 641 ± 178 | 490 ± 200 |
| MCF7 control 9 | ND | 4/6 | 530 ± 100 | 490 ± 300 |

*p = 0.002 vs. MCF7 control clones; Chi-square analysis
**p = NS

Soft agar assays were performed as described (Jiang, W., et al., 1993) and results are presented as the means±s.e. number of colonies per 5×10$^4$ plated cells/well for six wells. For tumorigenicity assays, five week-old female CD1nu/nu mice (Charles River Laboratories) were implanted with 1.7 mg estrogen/60 day release pellets (innovative Research of America) and injected subcutaneously with 5×10$^4$ MCF7 tumor cells. Mice were monitored biweekly for the development of tumors and tumor size was measured in two dimensions (length [a] and width [b]). Tumor volume was calculated according to V=ab$^2$/2.Mice were necropsied after eight weeks, and mean tumor volumes and weights were determined from the subgroup of mice with tumors present upon necropsy.

The ability of Beclin to suppress clonigenicity in soft agar assays suggested that it may also suppress tumorigenicity in vivo. Therefore, the ability of MCF7 Beclin 17 and three control clones to form tumors in five week old female nude mice implanted with slow-release pellets was compared. After an eight-week observation period, 66–77% of mice injected with control clones developed autopsy-confirmed tumors, as compared with only 14% of mice injected with Beclin-expressing cells, demonstrating that Beclin expression significantly decreases the incidence of tumor formation. The tumors that did develop in mice injected with MCF7 Beclin 17 cells tended to have reduced tumor volume and weight compared to those in mice injected with control MCF7 clones, but these differences were not statistically significant. No difference were observed with respect to the rate of tumor growth or tumor histology.

In summary, the yeast two hybrid system was used to isolate a cDNA that encodes a predicted coiled coil protein, Beclin, that interacts with members of the Bcl-2 family that negatively regulate apoptosis. A functional role for Beclin in anti-apoptotic pathways is suggested both by Bcl-2 and Bcl-$x_L$ mutational studies showing a correlation between disruption of anti-apoptotic function and binding to Beclin, and by studies in which beclin antisense RNA partially blocks Bcl-2-mediated protection against virus-induced apoptosis. While the function of beclin, when expressed ac normal levels in mammalian cells, is still unknown, its overexpression can inhibit cellular proliferation. These observations are consistent with the hypothesis that Bcl-2 may inhibit apoptosis by interacting with a gene product that exerts effects on cellular proliferative machinery. Furthermore, these findings, coupled with previous studies that have mapped beclin transcripts to a breast and ovarian cancer susceptibility locus on chromosome 17q21 (Rommens, 1995; Friedman, 1994; Friedman, 1995), warrant additional investigation to determine whether beclin, and its interactions with Bcl-2, play a role in human cancer.

REFERENCES FOR FIRST SERIES OF EXPERIMENTS

1. Altschul, S. F., et al. (1990) J. Mol. Biol. 215: 403–410.
2. Boehme, S. A. and Lenardo, M. J. (1993) Eur. J. Immunol 23: 1552–1560.
3. Boise, L. H., et al. 1993) Cell 74: 597–608.
4. Borner, C. (1996) J. Biol. Chem. 271: 12695–12698.
5. Boyd, J., et al. (1994) Cell 79: 341–351.
6. Buttyan, R. (1991) Genetic response of prostate cells to androgen deprivation: insights into the cellular mechanisms of apoptosis. In Tomei LD, Cope FO (eds): Apoptosis: The Molecular Basis of Cell Death. Plainview, NY: Cold Spring Harbor Laboratory Press 157–173.
7. Cheng, E. H., et al. (1996) Nature 379: 554–556.
8. Chittenden, T. (1995) Nature 374: 733–736.
9. Clarke, A., et al. (1992) Nature 359: 328–330.
10. Cropp, C. S, et al. (1993) Cancer Res. 53: 3382–3385.
11. Eccles, D. M., et al. (1992) Oncogene 7: 2069–2072.
12. Evan, G. I., et al. (1995) Curr. Opin. Cell Biol. 7: 825–834.
13. Evan, G. I., et al. (1996) Cell 69: 119–128.
14. Evan, G. I., et al. (1995) Curr. Opin. Cell Biol. 7: 825–834.
15. Farinelli, S. E. and L. A. Greene (1996) J. Neurosci. 16: 1150–1162.
16. Farrow, S. N., et al. (1995) Nature 374: 731–733.
17. Fernandez-Sarabia, M. J., et al. (1993) Nature 366: 274–275.
18. Freeman, R. S., et al. (1994) Neuron 12: 343–355.
19. Friedman, L. S., et al. (1994) Cancer Res. 54: 6374–6382.
20. Friedman, L. S., et al. (1995) Genomics 25: 256–263.
21. Futreal, P. A., et al. (1994) Science 266: 120–122.
22. Futreal, P. A., et al. Cancer Res. 52: 2624–2627.
23. Gadella, T. J., et al. (1994) Biophys Chem. 48: 221.
24. Hall, J. M., et al. (1990) Science 250: 1684–1689.
25. Hanada, M., et al. (1995) J. Biol. Chem. 270: 11962–11969.
26. Herman, B., et al. (1997) J. Fluorescence 7: 85.
27. Hockenbery, D., et al. (1993) Cell. 75:241–251.
28. Hosking, L., et al. (19) 5) Nature Genet 9: 343–344.
29. Jacks, T., et al. (1992) Nature 359: 295–300.
30. Jiang, W., e. al. (1993) Oncogene 8: 3447.
31. Kane, D. J., et al. (1993) Science. 262:1274–1276.
32. Kiefer, M. C., et al. (1995) Nature 374: 736–739.
33. King, K. L. and Cidlowski, J. A. (1995) J. Cell. Biochem. 58: 175–180.
34. Lam, M. et al. (1994) Proc Natl Acad Sci USA 91:6569–6573.
35. Lee, E-H, et al. (1992) Nature 359: 288–294.
36. Levine, B. et al. (1996) Proc. Natl. Acad. Sci USA 93: 4810.
37. Levine, B., et al. (1993) Nature 361: 739–742.
38. Liang, X. H., et al. (1994) Oncogene 8: 2645.
39. Liang, X. H., et al. (1995) J. Cell Biochem. 57: 509.
40. Linette, G. P., et al. (1996) Proc. Acad. Sci USA 93: 9545.
41. Lupas, A., et al. (1991) Science 252: 1162–1164.
42. Mahajan, N., et al. (1996) Mol. Cell Biol. 7s: 347a.
43. Matzel, S., et al. (1996) J. Exp. Med. 183: 2219–2226.
44. Meikrantz, W. and Schlegel, R. (1996) J. Biol. Chem. 271: 10205.
45. Merajver, S. D., et al. (1995) Nature Genet. 9: 439–443.
46. Miki, Y., et al. (1994) Science 266: 66–71.
47. Miura, M., et al. (1993) Cell 75:653–660.
48. Oltvai, Z., et al. (1993) Cell 74: 609–619.
49. O'Reilly, L. A., et al. (1996) EMBO J. 24: 6979.
50. Park, J. R., and Hockenberry, D. M. (1996) J. Cell. Biochem. 60: 12–17.
51. Qin, X., et al. (1994) Proc Natl Acad Sci USA 91: 10918–10922.
52. Reed, J. C., et al. (1990) J. Cell. Biochem. 60: 23–32.
53. Rommens, J. M., et al. (1995) Genomics 28: 530–542.
54. Root, D. (1997) Proc. Natl. Acad. Sci USA 94: 5685.
55. Russell, S. E. H., et al. (1990) Oncogene 5: 1581–1583.
56. Saito, H., et al. (1993; Cancer Res. 53: 3382–3385.
57. Sambrook, et al. (1989) Molecular Cloning-A Laboratory Manual, 2nd Edition, Cold Spring Harbor Laboratory Press.
58. Sato, T., et al. (1994) Proc. Natl. Acad Sci USA 91: 9238–9242.
59. Sedlak, T. W., et al. (1995) Proc. Natl. Acad. Sci. USA 92: 7834–7838.
60. Selvin, P. R. (1995) Methods in Enzymol 246: 400.
61. Shan, B. and Lee, W. H. (1994) Mol Cell Biol 14: 8166–8173.

62. Shi, L., et al. (1994) Science 263: 1143–1145.
63. Shibasaki, F., et al. (1997) Nature 386: 728.
64. Soares, M. B., et. al. (1994) Proc. Natl. Acad. Sci USA 91: 9228–9232.
65. Stryer, L. (1978) Annu Rev. Biochem. 47: 819.
66. Szabo, C. I. and Kirg, M. C. (1996) Hum. Mol. Genet. 4 review: 1811–1817.
67. Takayama, S., et al. (1995) Cell 80: 279–284.
68. Takhashi, H., et al. (1995) Cancer Res. 55: 2998–3002.
69. Tanaka, N., et al. (1994) Cell 77: 829–839.
70. Tangir, J., et al. (1996) Oncogene 12: 735–740. Tsujimoto, Y., et al. (1985) Science 228: 1440–1443.
71. Vairo, B., et al. (1996) Oncogene 13: 1511.
72. Wang, X. F., et al. (1993) Bioimaging 1: 30.
73. Wang, H-G., et al. (1994) Oncogene 90: 2751–2756.
74. White, E., et al. (1991) J. Virol. 65: 2968–2978.
75. Wu, P. and Brand, L. (1994) Anal. Biochem. 218: 1.
76. Wu, X., and Levine, A. J. (1994) Proc Natl. Acad Sci USA 91: 3602–3606.
77. Wyllie, A. H., et al. (1987) J. Cancer 56: 251–259.
78. Yan-Feng, et al. (1993) Int.J.Cancer 54: 546–551.
79. Yang, E., et al. (1995) Cell 80: 285–291.
80. Yin, X. M., et al. (1994) Nature 369: 321–323.

SECOND SERIES OF EXPERIMENTS

Sequencing of 5' and 3' nontranslated regions of human beclin. The 5' and 3' untranslated sequences of human beclin in may be obtained by performing RACE using the Clontech MARATHON KIT and MARATHON-READY mammary cDNA. The 5' untranslated sequence consists of 120 bp and is shown in FIG. 8A. The 3' untranslated sequence consists of 654 bp and is shown in FIG. 8B.

Identification of aberrant beclin transcripts in sporadic ovarian cancer. To determine whether beclin fulfills the criteria of a tumor suppressor gene important for ovarian cancer (e.g. functional inactivation of both beclin alleles), reverse transcriptase-PCR of RNA obtained from :our sporadic epithelial ovarian cancers with monoallelic deletions of the beclin-spanning region of chromosome 17q21 and from four normal ovaries was performed. As one allele of beclin is already deleted in these ovarian tumors, the demonstration of an inactivating mutation on the remaining present allele would fulfill the Knudson two hit hypothesis criteria (Knudson et al., 1985) and constitute proof that beclin is a tumor suppressor gene.

In all four of the ovarian tumors with deletions of one beclin allele, sequence analysis of PCR-amplified beclin cDNA products revealed heterozygosity in the region of beclin between nucleotides 1042 and 1185. To further evaluate this, the PCR products were cloned into the TA cloning vector, and several individual subclones for each sample (N>10) were sequenced. Analysis has been completed of three of the four ovarian tumor samples and four normal ovaries. All three of the ovarian cases had aberrant splice products present, whereas none of these splice products were found in the four normal ovaries. In addition, these splice products have not been detected (using a similar approach) in RNA extracted from normal brain, normal colon, normal breast, or five different tissue culture cell lines. The splicing patterns detected in the three ovarian cancer cases are depicted schematically in FIG. 9A. In all instances, the splicing variation occurred beginning a nucleotide 1042 and resulted in a premature termination codon. Three different patterns were observed simultaneously in one case (deletion of nucleotides 1042–1185 with resulting frameshift/stop codon; intronic insertion after 1042, with deletion of 1042–1185, with resulting frameshift/stop codon; and intronic insertion between nucleotides 1041 and 1042 with resulting frameshift/stop codon). The other two tumors had only deletions of 1042–1185. This type of aberrant splice pattern is highly suggestive of a splice site mutation at either the acceptor splice site upstream of the exon beginning at 1042 or at the donor splice site downstream of the exon ending at nucleotide 1185. Studies are in progress (see below.) to sequence these splice junction regions in genomic DNA from the same tumor samples to identify the precise genomic mutations responsible for this aberrant beclin splicing. Such genomic DNA mutations will likely be identified in this region of beclin; such a finding would further confirm that beclin is an important tumor suppressor gene for sporadic ovarian cancer.

Altered subcellular distribution of aberrant beclin cDNA transcripts found in ovarian cancer. To begin to compare the phenotype of the alternative beclin splice products found in ovarian tumors (described in the previous section) with full-length wild-type beclin, flag epitope-tagged beclin deleted of nucleotides 1042–1185 (flag-beclinΔ1042–1185) and flag-wild-type beclin were cloned into the mammalian expression vector, pSG5. After transfection of monkey COS-7 cells and human breast carcinoma MCF7 cells, the pattern of immunostaining of flag-BeclinΔ1042–1185 differed significantly from flag-wild-type Beclin. Wild-type Beclin is found exclusively in the cytoplasm, predominantly in the perinuclear region, except for G2/M-specific nuclear localization in MCF7 cells. In contrast, BeclinΔ1042–1185 is found diffusely in both the cytoplasm and the nucleus in asynchronous COS and MCF7 cells (see FIG. 10). The ability of this aberrant isoform to enter the nucleus in a cell cycle-independent fashion (versus cell cycle-dependent fashion of wild-type Beclin) may have important implications for potential mechanisms by which it might have different biologic effects than full-length Beclin. Studies are in progress to directly compare the tumor suppressor function of BeclinΔ1042–1185 with wild-type Beclin.

Loss of Beclin expression in invasive breast carcinoma. To examine whether Beclin may be functionally inactive in human sporadic Dreast cancers, a comparison was done of the levels of Beclin protein expression in marched normal and malignant breast tissue from the same cases, using a polyclonal anti-Beclin peptide (aa 1–15) antibody, 843 (N=20). As shown in the Western blot in FIG. 11, 843 reacts specifically with a 61 kd protein in human breast tissue that migrates identically on SDS-Page gels to human Beclin expressed in transfected cells. By Western blot analysis, 15 of 17 samples with detectable Beclin in normal tissue had absent (N=7) or significantly reduced Beclin (N=8) in the tumor tissue. (Some normal tissues were negative presumably due to the absence or limited number of epithelial cells in the tissue sample; the absence of protein in these samples was confirmed by Western blot analysis of actin expression.). Since equivalent volumes of normal and tumor tissue (rather than equivalent amounts of extracted protein) were analyzed, and normal tissue contains primarily fat cells whereas tumor tissue contains primarily epithelial cells, Western blot analysis using an anti-actin antibody confirmed hag tumor samples invariably contained significantly higher concentrations of protein. Thus, the decreased level of Beclin protein expression in tumors cannot be explained by a decrease in the amount of total protein loaded.

To confirm that the decreased Beclin protein expression in tumors observed on Western blot analysis reflected loss of expression in epithelial cells, immunocytochemical staining was performed to detect Beclin protein using antibody 843 in paraffin-embedded sections from 10 of the matched normal and malignant breast samples analyzed by Western blot. In all 10 cases, there was strong Beclin immunoreactivity in all normal breast epithelial cells. However, in 5 of the 10 cases, Beclin immunoreactivity was completely absent in the malignant epithelial cells. (An example of Beclin staining in normal epithelia but not malignant epithelia from one representative case of breast cancer (patient 516) is shown in FIG. 12.) Thus, these findings suggest that Beclin protein expression is lost in about half of invasive breast cancer cases, and are consistent with the genetic evidence hat beclin is a tumor suppressor gene important for breast cancer.

B. Studies in Progress

Sequencing of beclin splice site junctions in ovarian, breast, and prostate cancer. The detection of aberrant beclin splice products in ovarian cancer (see FIG. 9), suggests that one mechanism of beclin inactivation in ovarian, breast, and/or prostate tumors is through mutations in the splice site regions at the 5' or 3' intron-exon boundaries of the beclin exon spanning from nucleotide 1042–1185. This possibility may be evaluated by amplifying by PCR beclin genomic DNA fragments spanning the exon-exon boundaries at 1041/1042 and at 185/1186 from ovarian tumors containing 17q21 LOH and from peripheral blood from the same patients and performing DNA sequencing of the PCR products. Breast and prostate tumor samples from 17q21 LOH may be screened, and once 17q21 LOH samples are identified, such samples may be subjected to the same analyses to detect similar splice site mutations in breast and prostate samples. It is anticipated that these analyses will identify somatic mutations in ovarian, breast, and prostate tumors in beclin splice site regions. Furthermore, it is predicted that these somatic mutations will lead to aberrant beclin cDNA transcripts which have loss-of-tumor suppressor function. The presence of aberrant beclin cDNA transcripts in samples containing beclin splice site mutations may be confirmed by sequencing RT-PCR-amplified beclin RNA, and the loss-of-tumor suppressor function of such transcripts may be confirmed by studying their ability to suppress the ability of human breast carcinoma MCF7 cells to form tumors in nude mice.

Sequencing of beclin 5' and 3' untranslated regions (UTR's), DNA in ovarian, breast, and prostate cancer samples with monoallelic deletions of beclin. The observation that Beclin protein expression is absent in about 50% of cases of breast cancer supports the hypothesis that mutations may occur in cancer in regions of the beclin gene that regulate levels of expression. Such regions may include the 5' and 3' UTRs and the promoter and enhancer regions. To identify potential mutations in the 5' and 3' UTRs of beclin, genomic DNA extracted from ovarian, breast, and prostate cancers containing 17q21 LOH may be amplified by PCR using primers that span either the 5' UTR or 3' UTR and the PCR products may be sequenced. Genomic DNA from peripheral blood from the same cases may be analyzed in a similar fashion to detect whether any somatic mutations are present in the tumor DNA. It is anticipated that these studies will identify muations in the 5' or 3' NTR regions of human beclin n breast, ovarian, and/or prostate cancer samples which lead to decreased levels of Beclin protein expression In the tumors.

Sequencing of beclin promoter and enhancer regions in ovarian, breast, and prostate cancer samples with monoallelic deletions of beclin. Sequences of complete genomic Beclin may be determined. From the sequence of the full-length beclin gene, available software may be used for identification of potentially important regulatory sequences, including promoters and enhancers. (e.g. Reese's neural network algorithm for identifying promoters, MOTIFS type software for identifying elements often occurring within enhancers and promoters, and other public and commercial programs maintained in packages compiled by the Columbia Genome Center Informatics Section). One may perform mutation analysis of all beclin regulatory sequences in genomic DNA from ovarian, breast, and prostate cancer samples with 17q21 LOH to detect mutations in the remaining allele. Genomic DNA from the promoter and enhancer regions may be amplified by PCR and PCR products may be sequenced. The sequences may be compared to control DNA from normal cells for each patient with cancer. It is anticipated that these studies will identify mutations in the promoter or enhancer regions of the beclin gene that affect regulation of beclin gene expression in breast, prostate, or ovarian cancer.

Analysis of methylation status of beclin DNA promoter in ovarian, breast, and prostate cancer samples with monoallelic deletions of beclin. Aberrant methylation of normally unmethylated CpG islands has been associated with transcriptional inactivation of defined tumor suppressor genes in human cancers, including p16, p15, E-cadherin, and von Hippel-Lindau and is postulated to be the mechanism of inactivation of the tumor suppressor gene p73 in neuroblastomas (Kaghad et al., 1997). Further experiments will determine whether hypermethylation of the beclin promoter occurs in the remaining allele in breast, ovarian, and prostate cancer cases with 17q21 LOH. DNA extracted from breast, ovarian and prostate cancer cases may be subjected to the PCR assay for methylation status of CpG islands described in the methods sections. It is anticipated that these studies will find that the promoter region of beclin is hypermethylated, thereby constituting an epigenetic mechanism for silencing beclin expression in ovarian, breast, and/or prostate cancers.

Mutation analysis of coding regions of beclin in ovarian, breast, and prostate cancer samples with monoallelic deletions of beclin. Although the analyses completed to date on ovarian and breast cancer samples specifically suggest mutations in splice site junctions or in regulatory regions of beclin, most tumor suppressor genes contain a variety of different types of mutations in different cancers. In addition, coding region mutations which lead to decreased protein stability could also explain the loss of Beclin protein expression observed in human breast cancers. Therefore, it is predicted that beclin may also be mutated in the coding regions in some ovarian, breast, and prostate cancers. To detect coding region mutations in genomic DNA from ovarian, breast, and prostate cancers with 17q21 LOH, each exon may be amplified by PCR separately using primers designed within the introns just beyond the splice sites and directed inwardly toward the exons. PCR products may be sequenced and compared to similarly amplified genomic DNA from peripheral blood. It is anticipated that these studies will identify coding region mutations in beclin in ovarian, breast, and prostate cancer.

Functional analysis of beclin mutations. The functional inactivation of beclin on both alleles in certain types of cancer would be definitive evidence that beclin is a tumor suppressor gene important in that type of cancer, and that such mutations may play a role in the development of that type of cancer. All of the mutational analyses performed above may be done using tumor samples that contain deletions of one allele of beclin. Thus, demonstration of an inactivating mutation on the remaining allele would be sufficient to classify beclin as a tumor suppressor gene important for the type of cancer in which such a mutation is found. Inactivation mutations include mutations in regulatory regions that lead to loss of Beclin protein expression or mutations in the coding region which lead to premature stop codons. Such mutations are functionally important and constitute definitive evidence for a mechanism whereby mutations in beclin can lead to the development of human cancer. The importance of mutations in the coding region that do not lead to premature stop codons may be determined by performing tumor suppressor functional assays with Beclin proteins containing such mutations. These assays may be performed as described in the methods section. One may make breast carcinoma cell lines that conditionally express the mutated form(s) of Beclin, and compare the ability of these cell lines to form tumors in nude mice with the ability of cell lines expressing wild-type Beclin. These studies would help determine whether muations observed in human cancers inactivate the tumor suppressor function of beclin.

Mutational analyses of beclin in ovarian, breast, and prostate carcinoma cell lines. in addition to performing mutation analyses of primary tumors containing 17q21 LOH, future experiments would also examine whether ovarian, breast, and prostate carcinoma cell lines contain mutations in beclin in ether the regulatory regions, coding regions, or splice site junctions. An identical approach may be used as that described above for tumor samples.

G2/M specific nuclear localization of Beclin and Bcl-2 in MCF7 cells. Observations in MCF7 cells suggest that Beclin has tumor suppressor activity in this cell type. To explore potential mechanisms by which Beclin may regulate the growth of MCF7 cells, it was investigated whether Beclin, like Bcl-2, undergoes cell-cycle dependent nuclear localization. In contrast to the usual pattern of association with cytoplasmic membranes in non-epithelial cells, Bcl-2 expression has been shown to increase during G2/M and to localize to mitotic chromosomes in cultured SV40-immortalized normal mammary epithelial cells and in epithelial cell lines derived from breast, ovary, colon, cervical, and pancreatic carcinomas.

Immunocytochemical and DNA staining of asynchronous and G2/M-arrested transiently transfected cells was performed to determine whether Beclin and Bcl-2 co-localize to mitotic nuclei in MCF7 cells. Similar to findings reported previously, very few MCF7 cells displayed any endogenous Bcl-2 staining in interphase, and when observed, staining was cytoplasmic. In contrast, after taxol treatment (which arrests cells in G2/M), the majority of MCF7 cells displayed endogenous nuclear Bcl-2 staining. In MCF7 cells transfected with Bcl-2 and flag-Beclin, the subcellular localization of Bcl-2 and flag-Beclin immunoreactivity was identical in each co-transfected cell and varied according to the stage of the cell cycle. In interphase cells, the pattern of immunoreactivity for Bcl-2 and flag-Beclin was identical to that described above in COS7 cells, with a punctate cytoplasmic appearance. In contrast, untreated MCF7 cells spontaneously traversing G2/M or taxol-treated MCF7 cells arrested in G2/M displayed nuclear localization of Bcl-2 and flag-Beclin. The pattern of Beclin staining was similar to that reported previously for Bcl-2. Both Beclin and Bcl-2 display a diffuse nuclear pattern in G2 or early prophase, co-localize with condensed chromosomes in late prophase and metaphase, and display little to no staining in anaphase. The Intensity of the flag-Beclin-staining was greater in mitotic than interphase cells and the number of transfected MCF7 cells that displayed detectable flag-Beclin protein expression was greater in taxol-treated vs. untreated cells, suggesting an increase in Beclin stability in G2/M. Nuclear localization or increased levels of flag-Beclin and Bcl-2 were not observed in co-transfected NIH3T3 cells treated with taxol. Thus, Beclin, like Bcl-2, undergoes G2/M-specific nuclear import and enhanced protein stability in MCF7 cells, but not in a non-epithelial cell line.

Identification of a Beclin Nuclear Export Signal. The cell-cycle regulated nucleocytoplasmic transport of Beclin suggested the examination of whether the leucine rich motif of Beclin (containing a high degree of homology with the nuclear export signals of PKI and HIV-1 Rev) encodes a functional nuclear export signal. Based upon mutagenesis studies with PKI nuclear export signal, one would predict that alanine substitutions of the leucine residues at positions 184 and 187 of Beclin would impair nuclear export. This prediction was tested by performing immuno-fluorescence studies of COS7, NIH3T3, and MCF7 cells transfected with either wild-type flag epitope-tagged Beclin or a flag epitope-tagged mutant Beclin containing alanine substitutions at amino acids 184 and 187 (referred to as NESM1 for nuclear export signal mutant 1). In contrast to the exclusive cytoplasmic localization of wild-type Beclin in interphase cells, Beclin NESM1 displayed both intense punctuate nuclear staining as well as cytoplasmic staining in all three cell types. The ability of two leucine mutations within a nuclear export signal motif to result in cell-cycle independent nuclear localization of Beclin (even in cell types which do not normally undergo cell-cycle dependent nuclear localization) provides evidence that Beclin contains a functional nuclear export signal.

METHODS

Rapid amplification of cDNA ends (RACE) To isolate and sequence the 5' and 3' untranslated regions of the human beclin cDNA, the RACE method was performed using he MARATHON cDNA amplification kit and MARATHON-PEADY human mammary cDNA obtained from Clontech, according to the manufacturer's instructions.

Preparation of tumor and control samples for DNA sequencing. Total RNA from ovarian, breast, and prostate cancer and control tissue and cell lines may be extracted using the RNAzol method according to the manufacturer's instructions (Teletest, Friendswood, Tex.), reverse transcribed using random hexamer primers, and PCR may be performed using primers that amplify full-length human beclin DNA. PCR products may be sequenced as described in the next section. Genomic DNA may be extracted using standard methods (Dracopli et al. 1997) and sequenced as described in the next section.

DNA sequencing. Automated cycle sequencing using dye tagged primers and terminators may be performed on PCR products using methods established at the Columbia University Core DNA Synthesis and Sequencing Facility. Primer walking, shotgun cloning, and sequence assembly may be performed using methods established in the Columbia Genome Center sequencing laboratory. Mutational analysis may be conducted using the methods established in the Columbia Genome Center laboratory for heterozygote analysis on other projects. Normal and modified sequences may be compared using the SEQUENCE NAVIGATOR software (Applied Biosystems, Inc., Foster City, CAT).

Loss-of-heterozygosity (LOH) analysis. LOH analysis of chromosome 17q21 of ovarian tumor samples was performed by the laboratory of Dr. Samuel Mok as described previously (Tangier et al., 1996). To select breast and prostate cancer cases for analysis, LOH studies may be performed on tumor DNA from microdissected tumor samples and normal DNA from peripheral tissue using the methods described by Tangir et al. A panel of eight highly polymorphic tandem repeat markers on chromosome 17q21 (D17S1320, D17S1321, D17S1328, D17S855, D17S1322, D17S1323, D17S1327 and D172136) may be used. The order, map position, relative distance between the markers, and relationship between the markers and beclin and BRCA1 is already known. Cases which have LOH which encompass beclin may be used for further analysis.

Methylation-specific PCR. The PCR assay for methylation stalls of CpG islands described in Herman et al. (Herman et al. 1996) may be used to assess whether beclin genomic DNA from primary tumors and normal tissue s hypermethylated. The methylation-specific PCR assay involves modification of the DNA by sodium bisulfite (converting all unmethylated but not methylated cytosines to uracil) and subsequent amplification with primers specific for methylated versus unmethylated DNA.

Western blot analysis. Western blot analysis of Beclin protein may be performed on protein extracted from normal and malignant breast, ovarian, and prostate tissue and cell lines, using the polyclonal human Beclin peptide antibody (amino acids 1–15) 843 (custom production by Eurogenetics, Belgium) and the ECL methods according to the manufacturer's instructions (Amersham). The amount of protein loaded may be normalized by also probing with an antibody that reacts with actin.

Immunocytochemical analysis. The cell type-specific expression patterns of human Beclin in normal and malignant breast, ovarian, and prostate tissue may be examined using the anti-Beclin 843 antibody and the ABC immunoperoxidase methods, according to the manufacturer's instructions (Vector Laboratories).

Construction of cell lines that conditionally express wild-type and beclin mutants. The human breast carcinoma cell line (derived from a tumor containing 17q21 LOH) may be used. MCF-tet off cells (Clontech) may be transfected with wild-type beclin and with any mutant beclin cDNAs that are detected in ovarian, breast, or prostate cancer to generate stable MCF7 cell lines that express tetracycline-regulatable levels of wild-type and mutant Beclin proteins. These cell lines may be used In the tumorigenicity assays described in the next section.

Tumorigenicity assays. Four week old female nude mice may be injected subcutaneously (s.c.) into the left inframammary pad with 5×106 tumor cells transfected with control plasmids or plasmids containing wild-type or mutant beclin (5 mice per treatment group) and may be implanted with a slow release estrogen pellet (1.7 mg/60 days) in the right dorsal thoracic region. Mice may also be implanted with either a slow release tetracycline pellet or placebo pellet in the left dorsal thoracic region. Tumor size may be measured biweekly and animals may be necropsied at eight weeks after injection for determination of tumor weight, histopathological studies, and analysis of gene expression.

REFERENCES FOR THE SECOND SERIES OF EXPERIMENTS

81. Cropp, C. S., et al. (1993) Identification of three regions on chromosome 17q in primary human breast carcinomas which are frequently deleted. Cancer Res. 53:3382–3385.

82. Dracopli N C, et al. Current Protocols in Human Genetics. John wiley & Sons, Inc. 1997.

83. Eccles, D. M., et al. (1992) Early loss of heterozygosity on 17q in ovarian cancer. Oncogene. 7:2069–2072.

84. Friedman, L. S., et al. (1994) The search for BRCA1. Cancer Res. 54:6374–82.

85. Friedman, L. S., et al. (1995) 22 genes from chromosome 17q21: Cloning, sequencing, and characterization of mutations in breast cancer families and tumors. Genomics 25:256–263.

86. Futreal, P. A., et al. Detection of frequent allelic loss on proximal chromosome 17q21 in sporadic breast carcinoma using microsatellite length polymorphisms. Cancer Res. 52:2624–2627.

87. Futreal, P. A., et al. (1994) BRCA1 mutations in primary breast and ovarian carcinomas. Science 266:120–122.

88. Gao, X., et al. (1995) Loss of heterozygosity of the BRCA1 and other loci on chromosome 17q in human prostate cancer. Cancer Res. 55:1002–1005.

89. Gao, X., et al. (1995) Localization of potential tumor suppressor loci to a <2 Mb region on chromosome 17q in human prostate cancer. Oncogene 11:1241–1247.

90. Herman J G, et al. (1995) Methylation-specific PCR: a novel PCR assay for methylation status of CpG islands. Proc. Natl. Acad. Sci USA 93:9821.

91. Hosking, L., et al. (1995) A somatic BRCA1 mutation in an ovarian tumour. Nature Genet. 9: 343–344.

92. Kaghad, M. et al. (1997) Monoallelically expressed gene related to p53 at 1p36, a region frequently deleted in neuroblastoma and other human cancers. Cell. 90:809–819.

93. Knudson Jr., et al. (1985) Hereditary cancer, oncogenes, and antioncogenes. Cancer Res. 5:1437–1443.

94. Merajver, S. D., et al. (1995) Somatic mutations in the BRCA1 gene in sporadic ovarian tumors. Nature Genet. 9:439–443.

95. Miki, Y., et al. (1994) A strong candidate gene for the breast and ovarian cancer susceptibility gene BRCA1. Science 266:66–71.

96. Russell, S. E. H., et al. (1990) Allele loss from chromosome 17 in ovarian cancer. Oncogene 5, 1581–1583.

97. Saito, H, et al. (1993) Detailed deletion mapping of chromosome 17q21 in ovarian and breast cancers: 2-cM region on 17q21.3 often and commonly deleted in tumors. Cancer Res. 53:3382–3385.

98. Sato, T., et al. (1991) Allelotype of human ovarian cancer. Cancer Res. 51:5118–5112.

99. Takahashi, H., et al. (1995) Mutation analysis of the BRCA1 gene in ovarian cancers. Cancer Res. 55:2998–3002.

100. Tangir, J. , et al. (1996, A 400 kb novel deletion unit centromeric to the BRCA1 gene in sporadic epithelial ovarian cancer. Oncogene 12:735–740.

101. Vogelstein, B., et al. Has the breast cancer gene been found? Cell 79:1–3.

102. Wang, H. G., et al. Bcl-2 targets the protein kinase Raf-1 to mitochondria. Cell 87:629–638.

103. Yang-Feng, T. L., et al. (1993) Allelic loss in ovarian cancer. Int. J. Cancer 54, 546–551.

Third Series of Experiments

The cellular antiapoptotic gene bcl-2 represents a novel class of antiviral host defense molecules which function both by restricting viral replication and by preventing virus-induced cell death. Bcl-2 blocks apoptosis in vitro induced by several different RNA viruses, including Sindbis virus (18, 41), influenza virus (13, 26), reovirus (31), Semliki Forest virus (34), LaCrosse virus (29), and Japanese B encephalitis virus (21). Previously, we have shown that Bcl-2 overexpression in virally infected neurons in vivo also protects mice against fatal encephalitis caused by the prototypic alphavirus, Sindbis virus (17). The protective effects of Bcl-2 against fatal Sindbis virus encephalitis were associated with a reduction both in neuronal apoptotic death and in central nervous system (CNS) viral replication. A similar antiviral effect of Bcl-2 overexpression has been observed during Sindbis virus infection in cultured AT3 cells (41) as well as during influenza virus infection of MDCK cells (26), Japanese B encephalitis virus infection of N18 cells (21), and Semliki Forest virus infection of AT3 cells (34). Although the role of endogenous Bcl-2 in antiviral defense has yet to be evaluated, these studies support the hypothesis that Bcl-2 may be important in protecting cells against viral infections.

Most previous studies examining the effects of Bcl-2 on viral infections have been with neurotropic RNA viruses (e.g., Sindbis virus, reovirus, Semliki Forest virus, LaCrosse virus, and Japanese B virus) (18, 21, 29, 31, 34, 41). Although Bcl-2 may affect viral replication and virus-induced apoptosis with non-neurotropic virus (e.g., influenza virus) (13, 26), host mechanisms to inhibit apoptosis may be of particular importance during viral infections of vital, nonrenewable cell populations such as neurons. In such instances, virus-induced apoptotic death of neurons may result in irreversible CNS pathology and death of the host organism (1, 17, 19, 25). Therefore, while apoptosis in other cell types may be an adaptive host defense strategy that reduces total viral burden for the organism (reviewed in references 11, 16, 36, and 39), unique strategies may have evolved to permit control of CNS viral replication without inducing apoptotic death of infected neurons. It is thus possible that cellular genes that play a role in preventing apoptosis during normal neuronal development (e.g., bcl-2 and bcl-$x_L$) (reviewed in reference 23) may also be important in regulating CNS viral replication and in defending against apoptosis induced by neurotropic viruses.

To further understand how the cellular gene bcl-2 exerts antiapoptotic and antiviral effects during CNS viral infection, we performed a yeast two-hybrid screen to identify Bcl-2-interacting gene products in adult mouse brain. In this study, we describe the identification of a novel Bcl-2-interacting gene product, which we named Beclin because of its predicted coiled-coil structure (hence, the "-in" suffix) and its interaction with Bcl-2 Becl). Like Bcl-2 overexpression, Beclin overexpression in neurons in vivo can inhibit Sindbis virus replication, reduce CNS apoptosis, and provide protection against fatal Sindbis virus infection. A Beclin construct lacking the putative Bcl-2-binding domain provides no protection and has no antiviral activity. The findings identify a novel protein, Beclin, which may play a role in host defense against Sindbis virus infection. In addition, they suggest that interactions with Bcl-2-like proteins may be important for the protective activity of Beclin.

RESULTS

Identification of beclin, a novel gene on chromosome 17q21. Previously, we demonstrated that Bcl-2 inhibits Sindbis) is virus replication 2nd prevents Sindbis virus-induced apoptosis in mouse neurons (17). To further understand the mechanisms by which Bcl-2 protects against Sindbis virus infection in neurons, we performed a yeast two-hybrid screen of an adult mouse brain library for complementary DNAs encoding proteins that bind to the cell death inhibitor Bcl-2. We constructed a bait plasmid (pGBT9/bcl-2) by fusing human bcl-2 (lacking the C-terminal signal-anchor sequence to ensure translocation to the nucleus) to the GAL4 DNA-binding domain, which was cotransformed with an oligo(dT) and random hexamer-primed adult mouse brain cDNA fusion library in a GAL4 activation domain vector, pGAD10. Of 1 million transformants, one positive colony was identified by the 5-bromo-4-chloro-3-indolyl-β-D-galactopyranoside (X-Gal) filter assay. Sequencing analysis of the cDNA plasmid rescued from this colony (F1) revealed a termination condon 42 bp downstream from the GAL4 activation domain, several predicted short open reading frames between nucleotides 124 and 1843 and a longer predicted open reading frame (with a good Kozak consensus sequence and multiple stop codons upstream) spanning from nucleotide 1855 to the 3' end of the insert. Thus, either the 14-aa fusion protein was interacting with Bcl-2 or one of the downstream open reading frames encoded a protein that contains its own activation domain and interacts with Bcl-2. To identify the Bcl-2-interacting region of F1, we fused nucleotides 1 to 1854 and 1855 to 2500 to he GAL4 activation domain in pGAD424 and tested for interactions with Bcl-2. Nucleotides 1855 to 2500, but not 1 to 1854, encoded a protein that interacts with Bcl-2 fused to the GAL4 DNA-binding domain (Table 1) but not with control GAL4 (DNA-binding domain plasmids containing p53, lamin (Table 1), or Sindbis virus glycoproteins (data not shown).

TABLE 1

Summary of yeast two-hybrid assay results

| CAL4 activation domain plasmid[b] | β-Galactosidase reaction with GAL4 binding domain construct[a] | | | | | | |
|---|---|---|---|---|---|---|---|
| | Empty | Bcl-2 | Bcl-$x_L$ | Bcl-$x_S$ | Bax | Lamin | p53 |
| Empty | − | − | − | + | − | − | − |
| F1 | | | | | | | |
| 1-2563 | − | − | − | ND | − | − | − |
| 1-1855 | − | − | − | ND | − | − | − |
| 1856-2563 (Mus Beclin 1-708) | − | + | + | ND | − | − | − |
| Human Beclin 1-708 | − | + | + | ND | | | |
| Beclin 1-450 | − | + | + | ND | − | − | − |
| Beclin 1-258 | − | − | − | ND | − | − | − |
| Beclin 262-450 | − | + | + | ND | − | − | − |
| Beclin 451-708 | − | − | − | ND | − | − | − |
| Beclin 1-1353 | − | − | − | ND | − | − | − |

[a]+, positive reaction within 15 min; −, lack of positive reaction at 24 h; ND, not determined.
[b]Nucleotide positions of genes fused to the plasmid.

A database search revealed that the nucleotide sequence of F1 (1855 to 2500) overlapped with sequences of several clones isolated from a normalized infant human brain cDNA library in the Merck EST (epitope tag sequence) database as well as clones from human breast (GT197) (32) and human fibroblast (B32) cells (8). These clones contain only partial open reading frames of a novel gene that encodes a protein with coiled coils. As explained above, we assigned the name beclin, to this gene because of the interaction of its encoded protein with Bcl-2 and the predicted coiled-coil structure of its encoded protein. Clones GT197 and B32 were both isolated in the generation of transcription maps of the breast cancer susceptibility locus on chromosome 17q21 and are mapped to a region located approximately 100 kb centromeric to the gene BRCA1. They lie within a 400-kb minimal deletion unit mapped by Tangir et al. in sporadic epithelial ovarian cancers (38).

Figure 13:
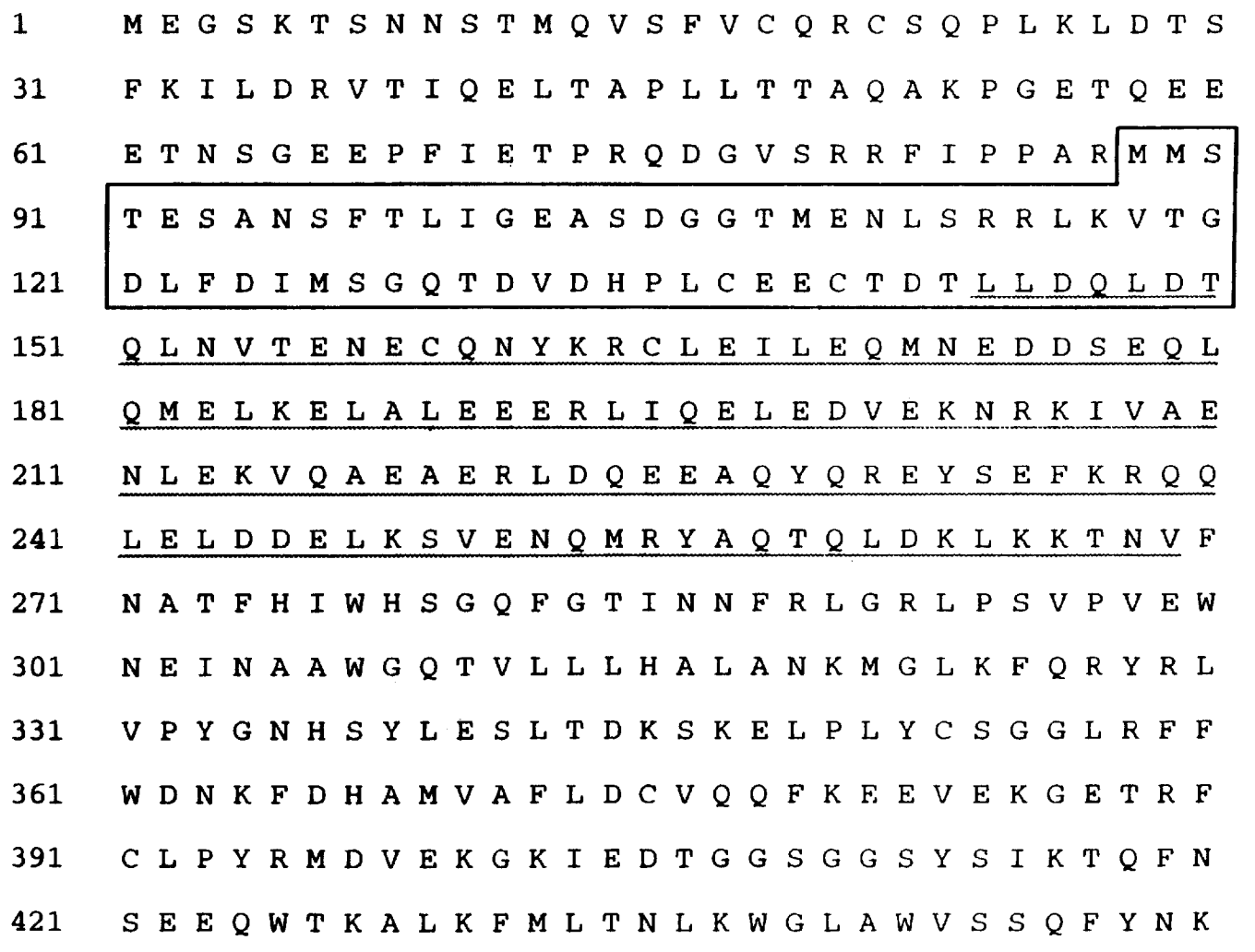

We aligned the overlapping partial clones in GenBank with mouse beclin sequence to obtain a predicted sequence of the full-length open reading frame of human beclin and isolated human beclin from a normalized human infant brain cDNA library (37). Human beclin is predicted to encode a novel 450-aa, 60-kDa protein containing a coiled-coil region with 25 to 28% homology with myosin-like proteins (FIG. 13). It shares 93% identity at the nucleotide level and 98% identity at the amino acid level with the mouse beclin sequence identified in the yeast two-hybrid screen. Human Beclin is also homologous with the *Ceanorhabditis elegans* T19E7.3 gene product (GenBank accession no. U42843) and the *S. cerevisiae* gene product Lph7p (GenBank accession no. U43503) (38 and 37% identical over 145 and 137 residues, respectively), indicating a high degree of evolutionary conservation. PROSITE analysis of human Beclin identified several potential glycosylation, phosphorylation, and myristoylation sites but no other functional sequence motifs.

Figure 14A:
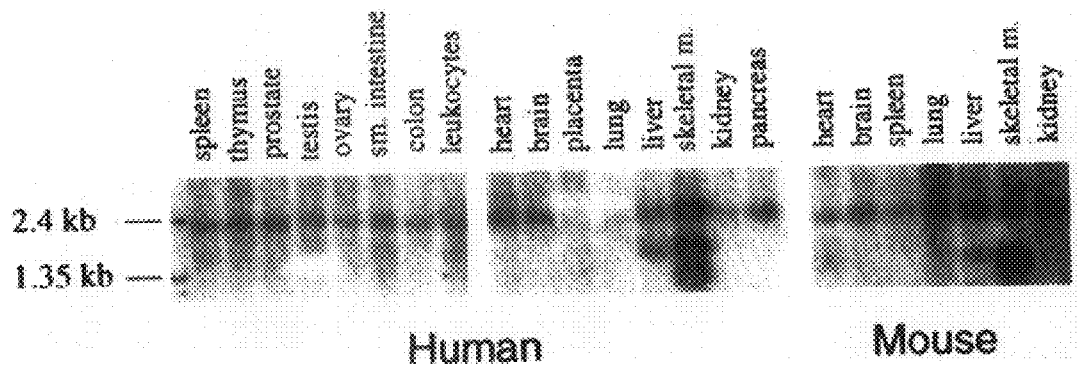

Ubiquitous expression of beclin mRNA in mouse and human tissues. To examine the tissue-specific pattern of beclin expression, we hybridized mouse and human multiple-tissue Northern blots with a beclin-specific probe. RNA bloc analysis revealed that expression of beclin mRNA is widespread in both mouse and human adult tissue (FIG. 14A). A beclin-specific probe hybridized to a 2.2-kb transcript present at highest levels in human skeletal muscle but at detectable levels in all tissues examined. The size of this transcript is approximately the same as that observed previously for clones GT197 and B32 (8, 32). In some tissues, additional 1.7- and 1.4-kb transcripts were observed, suggesting the presence of alternatively spliced transcripts.

Figure 14B:
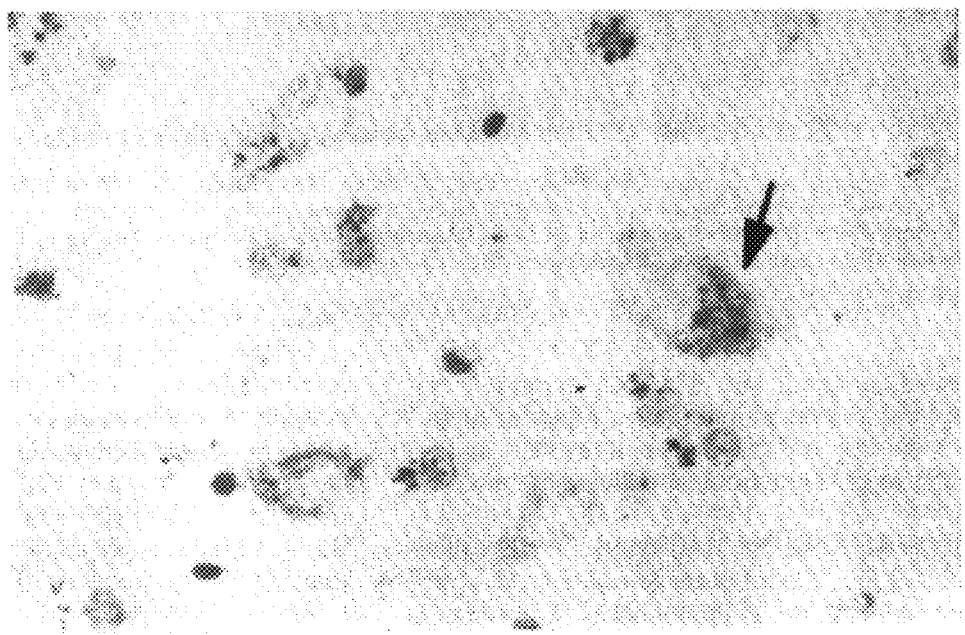

Beclin is expressed in human neurons. To examine whether Beclin protein is expressed in neurons (the primary CNS target cell type for Sindbis virus infection), we performed immuno-peroxidase staining of adult human brain sections. We used rabbit immune serum 843, generated against a human Beclin peptide corresponding to aa 1 to 15. 843 reacts with a 61-kDa protein in lysate prepared from BHK cells after infection with a recombinant Sindbis virus containing a flag epitope-tagged human beclin insert (SIN/beclin) (FIG. 15B). This protein migrates identically to the major band detected with an anti-flag epitope antibody in SIN/beclin-infected BHK cell lysate (FIG. 15A) and to in vitro translated flag-Beclin (data not shown). Immunoperoxidase staining of human brain sections from the hippocampus and frontal cortex revealed Beclin immunoreactivity in many neurons throughout these regions as well as in some glial cells. In neurons, Beclin demonstrated a granular, punctate pattern of staining that was found almost exclusively in the region of the perikaryon (FIG. 14B). Beclin immunoreactivity was also observed in the media of blood vessels, in the ependymal cells, and in the choroid plexus. No staining was observed in human brains stained with rabbit preimmune serum 843 (data nor shown).

Interaction of Beclin and Bcl-2. We performed additional yeast two-hybrid studies to confirm that human beclin, like mouse beclin, encodes a protein that interacts with human Bcl-2 and to further define the Bcl-2-interacting region of human Beclin (Table 1). We found that the region of human Beclin that corresponds to the mouse gene product isolated in the yeast two-hybrid screen (aa 1 to 236) also interacts with Bcl-2. Further deletion mutation analysis revealed that aa 88 to 150 of Beclin were sufficient to mediate an interaction with Bcl-2. Interestingly, the coding sequence for this region of Beclin is deleted in some human infant brain cDNA clones in the Merck EST database, suggesting that Beclin exists in at least two forms, including one that contains a Bcl-2-binding domain and one that lacks this domain. Full length-Beclin does not interact with Bcl-2 in the yeast two-hybrid system. As noted below, when expressed in transient transfection assays, flag-tagged full-length human Beclin displays a punctate immuno-reactivity pattern suggestive of association with intracellular organelles and is associated with he insoluble fraction after cell lysis. In contrast, a flag-tagged truncated Beclin (aa 1 to 236) (corresponding to the region isolated in the yeast two-hybrid screen) displays a diffuse cytoplasmic staining pattern and is soluble after cell lysis. These differences between full-length and truncated Beclin are thought to account for differences in ability to translocate to yeast nuclei and interact with Bcl-2 in the yeast two-hybrid assay.

To directly examine whether full-length human Beclin and Bcl-2 interact in mammalian cells, we performed FRET studies of COS7 cells cotransfected with Bcl-2 and flag epitope-tagged Beclin. Beclin is predicted to be a coiled-coil protein that may be associated with the cytoskeleton, and it partitions with the insoluble fraction following cell lysis. For this technical reason, biochemical analyses of in vivo interactions between Bcl-2 and Beclin cannot be performed. FRET is a fluorescence technique that can be used as a spectroscopic ruler to study and quantify the interactions of cellular components with each other (reviewed in references 6, 12, and 35). In FRET, a fluorophore (donor) in an excited state may transfer its excitation energy to a neighboring chromophore (acceptor) nonradiatively through dipole-dipole interactions. The efficiency of this process varies as the inverse of the sixth power of the distance separating the donor and acceptor chromophores and, in practice, requires the distance between the donor and acceptor fluorophores to be short (usually less than 50 Å). The dependence of the energy transfer efficiency on the donor-acceptor separation provides the basis for the utility of this phenomenon in the study of cell component interactions. FRET has been used by a number of investigators to examine interactions of cellular constituents (reviewed in 6, 12 and 35) such as endosomal fusion events, ligand-dependent growth factor receptor aggregations, interactions of viral and cellular proteins with regulators of apoptosis (20), and interactions of cellular cytoskeletal components (33).

Prior to measuring FRET, we first confirmed the colocalization of full-length Bcl-2 and Beclin in transfected COS7 cells, using confocal laser microscopy (FIG. 16). Bcl-2 is known to associate with the outer mitochondrial membrane, endoplasmic reticulum, and perinuclear membranes, and it displays a punctate pattern of cytoplasmic immunoreactivity (reviewed in reference 28). We found that flag-Beclin invariably displayed a pastern of immunoreactivity identical to that of Bcl-2 in all cotransfected COS7 cells examined by confocal laser microscopic analysis (FIGS. 16A to C). Furthermore, we found that deletion of the putative Bcl-2-binding domain from Beclin did not alter its pattern of immunoreactivity; flag-BeclinΔBcl-2BD appeared to have a pattern of staining similar to that of full-length Beclin, and like full-length Beclin, it colocalized with Bcl-2 in cotransfected cells (FIGS. 16D to F). This granular pattern to Beclin immunoreactivity in the perinuclear region is similar to that observed for endogenous Beclin in human neurons (compare FIGS. 14B, 16A and 16D).

After confirming the colocalization of Bcl-2 and Beclin and of Bcl-2 and BeclinΔBcl-2BD, we used FRET analysis to determine whether BCL-2 and Beclin physically interact. We compared in transfected COS7 cells the amounts of FRET between Bcl-2 and full-length Beclin, Bcl-2 and BeclinΔBcl-2BD, and Bcl-2 and a control protein, SERCA. Quantitative analysis of microscopic images (following corrections for cross-talk between filter sets and donor and acceptor concentrations showed significantly more FRET in cells with labeled full-length Beclin and Bcl-2 ($E_{Beclin-Bcl-2}$=0.000578±0.000262; mean±standard error of the mean [SEM], n=410) than in cells with labeled BeclinΔBcl-2BD and Bcl-2 ($E_{Beclin\Delta Bcl-2BD-BL-2}$=0.000189±0.000151; n=2, 946) (P=0.0068, t test) or in cells with labeled SERCA and Bcl-2 ($E_{SERCA-Bcl-2}$=0.000639±0.0000390; n=775) (P=0.0021, t test). These quantitative analyses indicate that Beclin and Bcl-2 exhibit FRET and provide evidence of an interaction between these two proteins in mammalian cells. Furthermore, deletion of the Bcl-2-binding domain of Beclin mapped in yeast two-hybrid studies does not alter the spatial orientation of transfected Beclin, but it does significantly decrease FRET. This observation suggests that the FRET observed between full-length Beclin and Bcl-2 reflects a specific association of these proteins in vivo, rather than an artifact secondary to overexpression.

Selective interaction of Beclin with death repressor members of the Bcl-2 family. To investigate whether Beclin interacts with other Bcl-2 family members that positively or negatively regulate apoptosis, we fused bax, bcl-$x_S$, and bcl-$x_L$ into the GAL4 binding domain vector and tested for interactions with Beclin in the yeast two-hybrid system (Table 1). The Bcl-$x_S$ GAL4 binding domain construct activated transcription by itself and therefore could not be tested for interactions with Beclin. The same region of Beclin (aa 88 to 150) that interacted with Bcl-2 also interacted with Bcl-$x_L$, a related Bcl-2 family member that inhibits apoptosis (4). In contrast, Beclin did not react with Bax, a family member that promotes apoptosis (27). This pattern of interaction, i.e., with Bcl-2 and Bcl-$x_L$, but not Bax, is identical to that observed for all previously identified Bcl-2-interacting proteins outside the Bcl-2 family (reviewed in reference 30).

Mutations in Bcl-2 and Bcl-$x_L$ that block death repressor activity also block binding to Beclin. Cheng et al. have shown that Bcl-2 and Bcl-$x_L$ overexpression can delay Sindbis virus-induced death of BHK cells (5). To evaluate whether Bcl-2-Beclin and Bcl-$x_L$-Beclin interactions may be related to this ability of Bcl-2 and Bcl-$x_L$ to inhibit Sindbis virus-induced apoptosis, we constructed pGBT9 vectors containing bcl-2 and bcl-$x_L$ constructs with mutations in the conserved BH1 domain that are known to block death repressor activity. A Gly-Ala mutation at amino acid position 145 of Bcl-2 completely abrogates Bcl-2 death repressor activity in interleukin-3 deprivation-, γ-irradiation- and glucocorticoid-induced apoptosis (42) and also blocks Bcl-2 binding to Beclin in the yeast two-hybrid system (Table 2). Similarly, substitution of aa 136 to 138 of Bcl-$x_L$ (VNX→AIL) completely abolishes death repressor activity in Sindbis virus-induced apoptosis (5) and also blocks Bcl-$x_L$ binding to Beclin (Table 2). These mutations in Bcl-2 (G-A145) and Bcl-$x_L$ (VNW→AIL) did not alter the level of Bcl-2 or Bcl-$x_L$ expression in yeast cells (data not shown), indicating that the lack of interaction could not be attributed to effects of the mutations on protein expression in yeast.

These data therefore demonstrate that mutations that block the antideath activity of Bcl-2 and Bcl-$x_L$ also block binding to Beclin.

TABLE 2

Effect of BH1 domain mutations on the ability of Bcl-2 and Bcl-$x_L$ to bind to Beclin in the yeast two-hybrid assay

| Construct[a] | Conserved BH1 domain | Inhibition of apoptosis (reference) | Beclin binding |
|---|---|---|---|
| WT Bcl-2 | ELFRDGVNWGRIVAFFEFGG | + | + |
| WT Lcl-$x_L$ | ELFRDCVNWGRIVAFFSFGG | + | + |
| MT Bcl-2 | ---------A---------- | - (42) | - |
| MT Bcl-$x_L$ | ---------AIL-------- | - (5) | - |

[a]WT, wild-type; MT, mutant.

Beclin protects mice against fatal encephalitis caused by the neurovirulent TE12 strain of Sindbis virus. After identifying Beclin as a novel Bcl-2-interacting protein that is expressed in neurons, we were interested in studying its effects on Sindbis virus infection. To directly evaluate the role of Beclin and its potential interactions with Bcl-2-like proteins in modulating Sindbis virus pathogenesis, we compared the natural histories of mice infected with recombinant chimeric viruses that express either wild-type human Beclin (SIN/beclin), human Beclin lacking the putative Bcl-2-binding domain (SIN/beclinΔBcl-2BD), or human Beclin containing a premature stop codon at nucleotide position 270 (SIN/beclinstop).

To construct these viruses, we used a strategy identical to that previously described for Sindbis virus chimeras that express human Bcl-2 (17), with the exception that we used a more neurovirulent background strain of Sindbis virus, dsTE12. We chose dsTE12 rather than the previously used less virulent strain ds633 because of the possibility that the larger size of the human beclin open reading frame insert would have an attenuating effect on Sindbis virus neurovirulence. Whereas ds633 is neurovirulent only in neonatal mice, dsTE is also neurovirulent in older mice (40). ds633 and dsTE12 differ at one amino acid position in the E2 envelope glycoprotein (Gln-55 in ds633, His-55 in dsTE12) and two amino acid positions in the E1 glycoprotein (Val-72 and Gly-313 in ds633; Ala-72 and Asp-313 in dsTE12). Previous studies with recombinant viruses have mapped the amino acid residue responsible for neurovirulence in older mice to position 55 in E2 (40, 41).

Figure 15A:
Figure 15B:
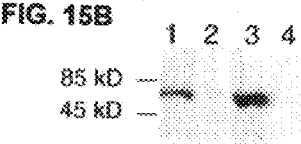
Figure 15C:
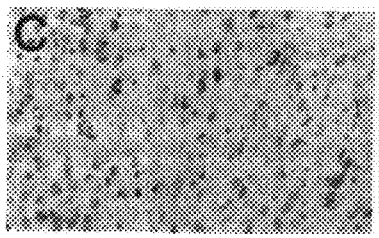
Figure 15D:
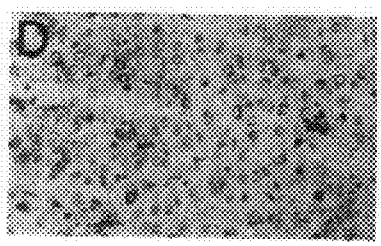
Figure 15E:
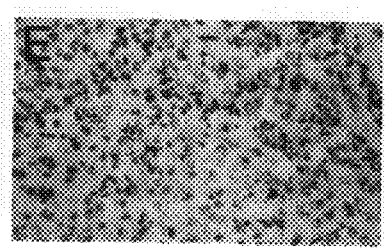
Figure 16A:
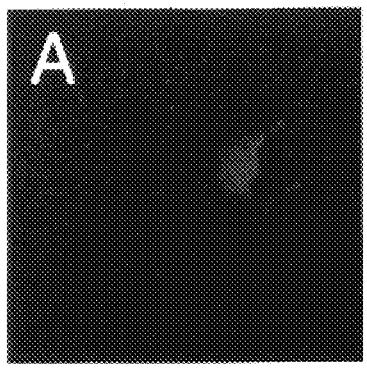
Figure 16B:
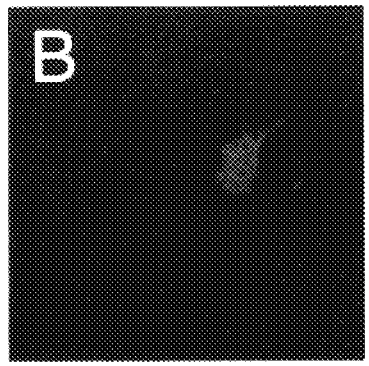
Figure 16C:
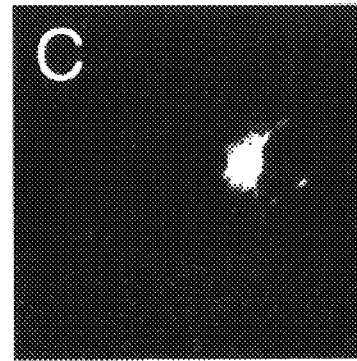
Figure 16D:
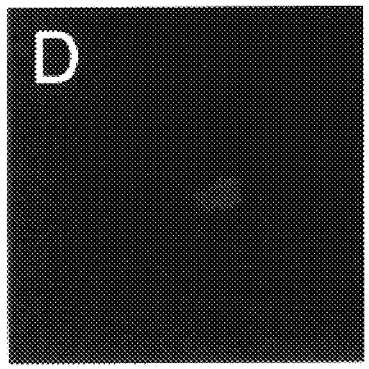
Figure 16E:
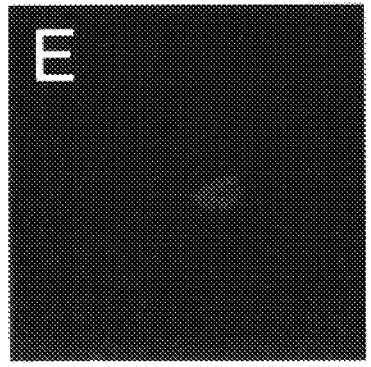
Figure 16F:
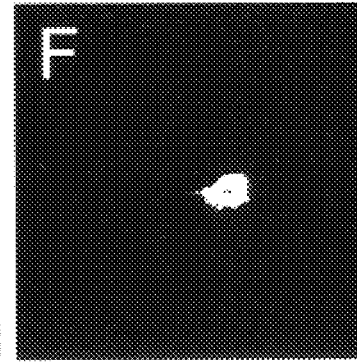

We confirmed that SIN/beclin and SIN/beclinΔBcl-2BD expressed proteins of the predicted molecular weights by performing Western blot analyses of infected BHK cell lysates with botch an anti-flag epitope monoclonal antibody and a polyclonal anti-human Beclin peptide antibody (FIGS. 15A and B). SIN/beclin expressed a 61-kDa protein and SIN/beclinΔBcl-2BD expressed a 52-kDa protein reactive with both anti-flag epitope and anti-Beclin antibodies. We also confirmed that human flag-Beclin and flag-BeclinΔBcl-2BD were expressed in virally infected neurons by performing immunoperoxidase staining of mouse brains at days 1, 2, and 4 after infection (representative photomicrographs shown in FIGS. 15C and E). Although we did not detect any flag-Beclin protein expression by Western blot analysis of BHK cell lysates infected with SIN/beclinstop, flag immunoreactivity was also observed in mouse brains infected with SIN/beclin (FIG. 15D). No flag immunoreactivity was seen in control mouse brains infected with the dsTE12 vector alone (data not shown). Fewer flag-immunoreactive cells were observed in SIN/beclin-infected than in SIN/beclinΔBcl-2- and SIN/beclinstop-infected mouse brains.

Figure 17B:
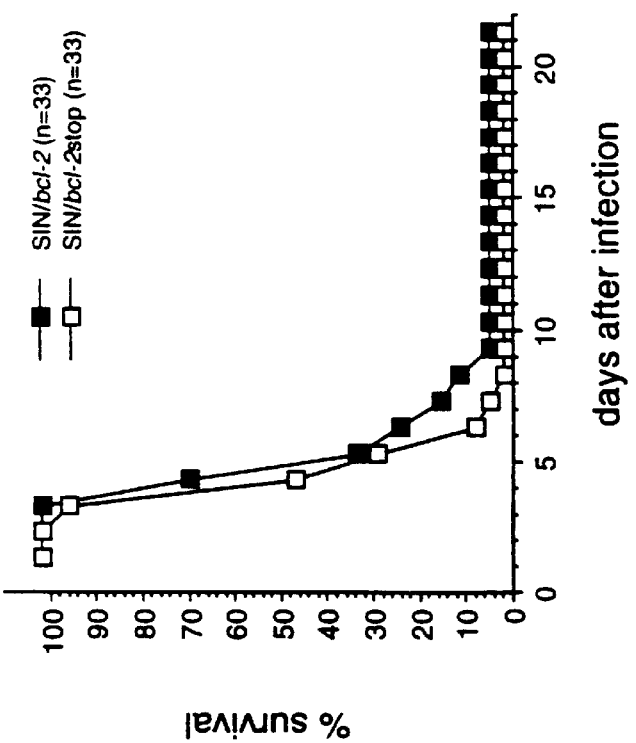
Figure 17A:
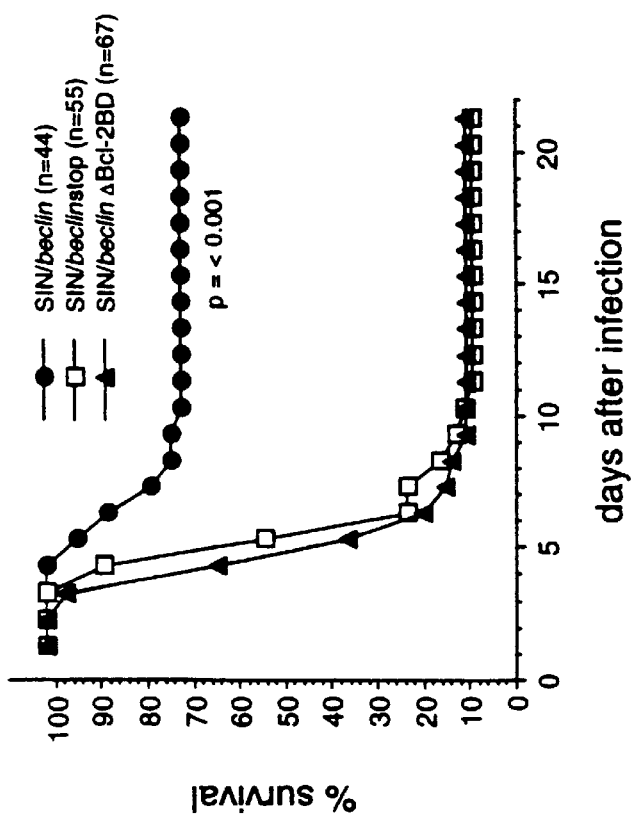

We compared the survival of 10-day-old litters of CD1 mice infected intracerebrally with 1,000 PFU of SIN/beclin, SIN/beclinΔBcl-2BD, and SIN/beclinstop (FIG. 17A). The survival of mice infected with SIN/beclin was 71%, compared with only 9 and 7% after infection with SIN/beclinΔBcl-2BD and SIN/beclinstop. The differences in survival between groups infected with SIN/beclin versus SIN/beclinΔBcl-2BD and Sin/beclin versus Sin/beclinstop were highly significant (P<0.001; life-table analysis). Thus, full-length Beclin overexpression in virally infected neural cells results in marked protection against fatal Sindbis virus encephalitis. Furthermore, the high mortality after infection with a virus expressing a mutant form of Beclin lacking the Bcl-2 binding domain suggests that binding to Bcl-2 or Bcl-2-like proteins is important for the protective effects of Beclin on survival in Sindbis virus encephalitis.

Bcl-2 does not protect against fatal encephalitis caused by TE12. Previously, we showed that Bcl-2, expressed in the ds633 Sindbis virus vector, protected neonatal mice against fatal Sindbis virus infection (17). However, in in vitro studies in AT3/bcl-2 cells, the TE12 strain overcomes protection conferred by Bcl-2 (41). To directly compare the ablities of Beclin and Bcl-2 to protect against encephalitis by TE12 in 10-day-old mice, we cloned human bcl-2 and human bcl-2 containing a premature stop codon after nucleotide position 118 into the dsTE12 vector to generate the constructs SIN/bcl-2 and SIN/bcl-2stop. Unlike Sin/beclin versus SIN/beclinstop (FIG. 17A), there was no difference in the survival of mice infected with SIN/bcl-2 versus SIN/bcl-2stop (FIG. 17B). Together with previous results (17), these data demonstrate that Bcl-2 can protect against fatal encephalitis caused by a strain of Sindbis virus containing a wild-type glutamine at position E2 position 55 but not by a more neurovirulent strain of Sindbis virus containing a histidine mutation at E2 position 55 (E2-55 histidine mutation).

Figure 18:
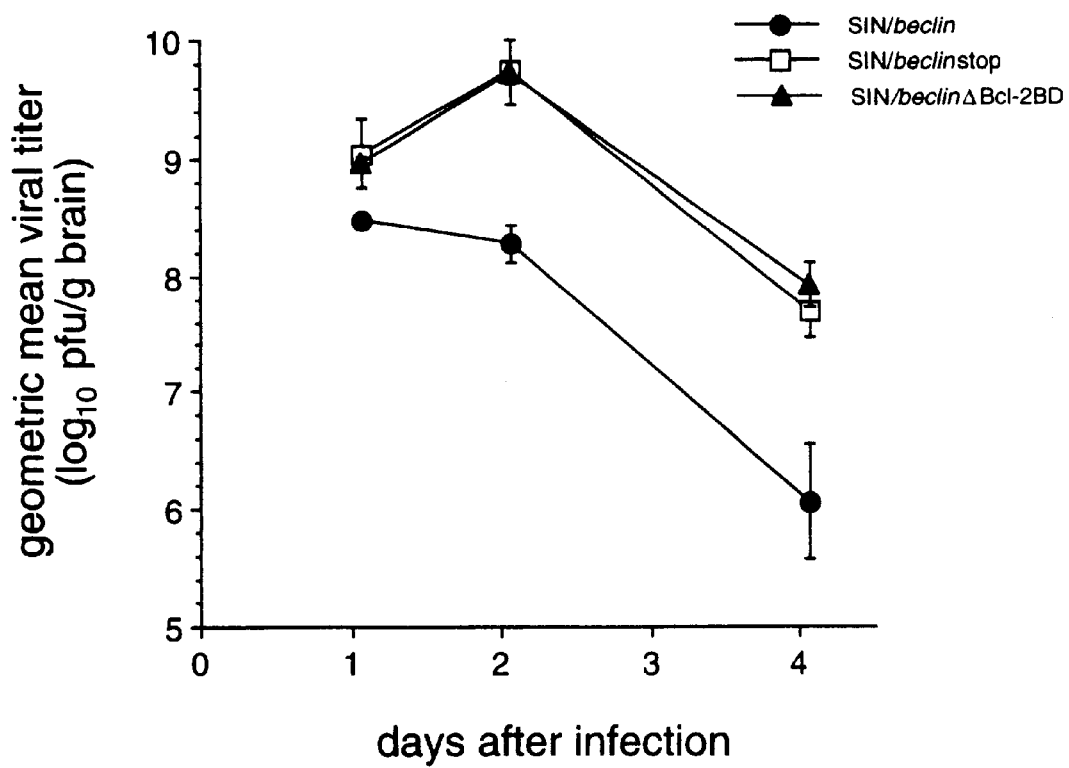

Beclin reduces Sindbis virus replication in mouse brain. To examine whether Beclin overexpression affects Sindbis virus replication, we measured viral titers of mouse brain homogenates and performed in situ hybridization of mouse brain sections to detect message-sense. viral RNA. Mean viral titers were reduced 5-fold at day 1 and 50-fold at days 2 and 4 after infection in brains of mice infected with Sin/beclin compared to the brains of mice infected with SIN/beclinstop or SIN/beclinΔbcl-2BD (FIG. 18). Computerized quantitative image analysis of virus RNA positive cells in infected mouse brains showed an inhibitory effect of Beclin on viral replication that was similar to, but had a temporal pattern somewhat different from, that observed by measurement of viral titers (FIG. 19). The mean number of virus RNA-positive cells was significantly lower in brains infected with SIN/beclin than in brains infected with SIN/beclinstop at day 4 after infection (100±36 versus 494±55; P=0.004, t test) but was equivalent at day 2 after infection (575±272 versus 507±216; P=0.854, t test). The reduction of viral titers but not of virus RNA-positive cells in mouse brains 2 days after infection with SIN/beclin suggests a possible inhibitory effect of Beclin on pcsttranscriptional stages of viral replication. In addition, the viral titers of SIN/beclinΔBcl-2BD-infected mouse brains did not differ significantly from titers of SIN/beclinstop-infected mouse brains, but the number of virus RNA-positive cells was higher at days 2 and 4 in SIN/beclinΔBcl-2BD-infected than in SIN/beclinstop-infected mouse brains. This difference was significant at day 4 (905±72 versus 494±55; P=0.01, t test) but not a day 2 (1,190±375 versus 0.507±216; P=0.190, t test) after infection.

The anatomic distribution of RNA-positive cells did not differ among the difference virus-infected groups; viral RNA-positive cells were found in clusters scattered throughout the brain, most commonly in the subventricular zone, posterior neo-cortex, colliculus, hippocampus, striatum, and olfactory bulb. However, the number of cells seen within a given cluster was usually lowest in SIN/beclin Δ Bcl-2BD-infected mouse brains (see representative photomicrographs in FIG. 21).

Beclin reduces Sindbis virus-induced cell death in mouse brain. To examine whether CNS Beclin overexpression reduces apoptotic cell death, we quantitated the number of apoptotic nuclei in the brains of mice infected with the chimeric viruses SIN/beclin, SIN/beclinstop, and SIN/beclin Δ Bcl-2BD (FIG. 20). Within each mouse brain, almost all apoptotic nuclei were found in regions that had detectable viral RNA by in situ hybridization (FIG. 21) and in regions that had histopathologic evidence of neuronal death. A close association was observed between the mean numbers of apoptotic nuclei at each time point among the three different virus treatment grops and the mean numbers of virus RNA-positive cells (compare results in FIGS. 19 and 20). In mouse brains infected with SIN/beclinstop, little cell death was seen at days 1 and 2 after infection, and the number of apoptotic cells per square millimeter of brain did not differ between these groups. More apoptotic nuclei were present at day 2 after infection in the brains of mice infected with SIN/beclin Δ Bcl-2BD (604±211) than in the brains of mice infected with SIN/beclin (133±90) or SIN/beclinstop (91±52); this deifference was nearly statistically significant (P=0.078, analysis of variance). At day 4 after infection, the mean number of apoptotic cells per square millimeter of brain was markedly increased in SIN/beclinstop (1,490±29) and SIN/beclin Δ Bcl-2BD(1,044±430) versus SIN/beclin-infected mouse brains (101±10; P=0.001, analysis of variance). These data demonstrate that Beclin overexpressio ndecreases apoptotic death in mouse brains infected with TE12 strain of Sindbis virus.

DISCUSSION

In this study, we describe the identification of a novel coiled-coil 60-kDa protein, Beclin, which interacts with the cell death regulator Bcl-2. We demonstrate that Beclin overexpression in virally infected neurons in vivo results in substantial protection against Sindbis virus-induced disease. Mice infected with recombinant Sindbis viruses that express wild-type Beclin have less neural cell apoptosis, decreased viral replication, ad a significant lower mortality rate than mice infected with recombinant viruses that express Beclin deletion mutants. Furthermore, the Bcl-2 binding domain of Beclin is required for the antiviral, antiapoptotic, and survival-promoting effects of Beclin on CNS Sindbis virus infection. These findings suggest that Beclin, via interactions with Bcl-2-like molecules, can function in vivo in the CNS as an antiviral host defense molecule.

The protective, antiviral effects of Beclin are mediated through inteactions with Bcl-2 (or Bcl-2-like molecules that bind to same region of Beclin as Bcl-2) is supported by data obtained with a chimeric Sindbis virus expressing Beclin lacking aa 88 to 151. Amino acids 88 to 150 of Beclin are sufficient to mediate an interaction with Bcl-2 and Bcl-x in the yeast two-hybrid assay, and deletion of these amino acids from full-length Beclin significantly decreases the strength of the Beclin-Bcl-2 interaction in mammalian cells. The Sindbis virus construct expressing Becl lacking aa 88 to 150 (SIN/beclinΔBcl-2BD) replicated to as high levels in muse brain, resulted in as much apoptotic neural cell death, and resulted in the same mortality in mice as a control recombinant virus which expressed a 90-aa truncated Beclin protein (SIN/beclin-stop). The lack of protedtive activity of BeclinΔBcl-2BD compared to full-lenght Beclin cannot be attributed to lower levels of BeclinΔBcl-2BD expression after infection with SIN/beclinΔBcl-2BD. The levels of flag-BeclinΔBcl-2BD were equal to or greater than levels of flag-Beclin detected immunoblot analysis of lysates from BHK cells infected with SIN/beclin and SIN/beclinΔBcl-2BD, respectively. In addition, SIN,beclinΔBcl-2BD-infected mouse brains had more flag-immunoreactive cells than mouse brains infected with SIN/beclin.

Thus, the lack of protective activity of BeclinΔBcl-2 is most consistent with the hypothesis that the antiviral effects of Beclin are mediated through interactions with Bcl-2-like proteins.

Some of the data in the present study suggest that the virus SIN/beclinΔBcl-2BD may be more neurovirulent than the virus SIN/beclinstop. Mice infected with SIN/beclinΔBcl-2BD had more virus RNA-positive cells in their brains at days 2 and 4 after infection than mice infected with compared to SIN/beclinstop. Although the overall mortality rates of mice infected with SIN/beclinΔBcl-2BD versus SIN/beclinstop did not differ, but the mean day of death was slightly lower in mice infected with SIN/beclinΔBcl-2BD versus SIN/beclinstop. These observations raise the possibility that Beclin lacking the Bcl-2-binding domain functions as a dominant negative mutant. As a corollary, the naturally occurring Beclin isoform found in brain that lacks the Bcl-2-binding domain may serve as a death-promoting molecule.

Beclin may exert antiviral effects via interactions with either Bcl-2, Bcl-$x_1$, or yet unidentified Bcl-2 family members. In yeast two-hybrid assays, we found that the same region of Beclin interacted with Bcl-2 and Bcl-$x_1$, and that loss-of-function mutations in the conserved BH1 domains of both Bcl-2 and Bcl-$x_1$, blocked binding to Beclin. While both Bcl-2 and Bcl-$x_1$, are important regulators of apoptosis in neurons (reviewed in reference 23), we have found that Bcl-2, but not Bcl-$x_1$, protects mice against fatal encephalitis and delays Sindbis virus-induced death of cultured rat dorsal root ganglion neurons (14,17). Thus, Bcl-2 may be more important than Bcl-$x_1$, as a regulator of Sindbis virus-induced death in neural cells. Additional studies examining the effects of Beclin on Sindbis virus infection in mice that are deficient in Bcl-2 may help define whether Bcl-2 is the biologically important Hbeclin-binding partner in in vivo antiviral pathways in the CNS.

The mechanisms by which Beclin, in cooperation with Bcl-2-like proteins, functions to inhibit Sindbis virus replication and sindbis virus-induced neuronal death are unknown. Both Simliki Forest virus and Sindbis virus have been shown to inactivate the antiapoptotic function of Bcl-2 in transfected fibroblasts through capase-induced Bcl-2 clevage (10). In addition, Nava et al. have shown that crmA increases the survival of Sindbis virus-infected mice (24), suggesting a role for fatal encephalitis. One possibility, therefore, is that binding to Beclin somehow protects Bcl-2 (or Bcl-$x_1$) from clevage by caspases, thereby preventing Sindbis virus-induced cell death. A second possibility is that the Beclin-Bcl-2-like protein complex blocks an endoplasmic reticulum stress signal triggered by the Sindbis virus E2 and E1 envelope glycoproteins. One of the mechanisms by which Bcl-2 and Bcl-may inhibit apoptosis is by regulating the permeability of intracellular membranes (reviewed in reference 30). Recently, we have shown that the overexpression of the transmembrane domains of the Sindbis virus E2 and E1 envelope glycoproteins induces apoptosis in AT3 cells (15). In addition, coiled-coil proteins such as Beclin may play a role in linking membrane signal trasduction events with the cytoskeleton. Thus, we speculate that Beclin, a protein which localizes to intracellular membranes, may be part of a complex with Bcl-2-like proteins hat regulates signalling events initiated by Sindbis virus envelope glycoproteins in the endoplasmic reticulum.

Many similarities exist between the findings of the present study and work examining the effects of Bcl-2 overexpression on the natural history of Sindbis virus encephalitis. As observed with Beclin in this study, the overexpression of Bcl-2 in virally infected neurons has previously been shown to reduce CNS apoptosis, reduce CNS Sindbis virus replication, and reduce Sindbis virus mortality (17). However, in the present study, we also identify one significant biologic difference between Bcl-2 and Beclin; namely, Beclin can exert protective effects against infection by a neurovirulent strain of Sindbis virus that is known to overcome the protective effects of Bcl-2. Ubol et al. demonstrated that a histidine substitution for wild-type glutamine at position 55 of the Sindbis virus E2 envelope glycoprotein was sufficient to enable the virus to kill cells expressing Bcl-2 (41). Similarly, we have previously found that Bcl-2 expressed in a strain of Sindbis containing a glutamine at position 55 (strain 633) protects against fatal encephalitis (17), but in the present study, we found that Bcl-2 expressed in a strain of Sindbis containing a histidine at position 55 (strain TE12) confers no protection against fatal disease. Yet, when expressed in an E2-55 histidine-containing background strain of Sindbis virus, Beclin confers significant protection. Thus, the mutation in E2, which confers neurovirulence, can counter the protective effects of Bcl-2 but not of Beclin.

Several explanations have been proposed to explain the ability of the E2-55 histidine mutation to confer resistance to Bcl-2 protection agaisnt Sindbis virus-induced death. Ubol et al. suggested that the neurovirulent mutation in E2 might somehow alter either a direct interaction between E2 and Bcl-2 in the endoplasmic reticulum or a possible effect of Bcl-2 on E2 protein folding or posttranslational modifications (41). More recently, Grandgirard et al. raised the possibility that the mutation in E2 facilitates the access of caspases to Bcl-2 and subsequent triggering of Bcl-2 cleavage(10). If viral activation of caspase-induced cleavage of Bcl-2 does prove to be an important mechanism of neurovirulence of Sindbis virus strains containing E2-55 histidine, Beclin may serve as an important host defense factor against this strategy of neurovirulence. This hypothesis is based on the ability of Beclin, a Bcl-2 interacting protein, to protect against neuronal death induced by the TE12 strain of Sindbis virus.

The antiviral effects of Beclin observed in Sindbis virus-infected mouse brains may be exerted at a stage of viral replication after viral RNA synthesis. At 2 days after chimeric virus infection, Beclin overexpression was associated with a 50-fold reduction in viral titers but no reduction in the number of viral RNA-positive cells. This finding suggests a block or abnormality at the level of either translation of the Sindbis virus structural proteins, posttranslational modifications of viral glycoproteins, virus assembly, or budding. This observation contrasts with previous studies examining the effects of Bcl-2 on infectionwith a related alphavirus, Semliki Forest virus (34). On the basis of in situ hybridization studies for viral RNA and immunostaining for viral proteins, Scallan et al. concluded that bcl-2 functions at an early stage of the virus life cycle, either entry, pretranscriptional events, or trarscription, to inhibit Semliki Forest virus replication (34). The discrepancy between the findings of Scallan et al. and those reported in the present study may reflect fundamental differences between the antiviral effects of Beclin and Bcl-2, differences between Sindbis virus and Semliki Forest virus, or differences between the cell types infected. Alternatively, it is possible that Bcl-2 and/or Beclin act at multiple overlapping stages of the alphavirus life cycle and that different experimental designs in the two studies uncovered effects on different phases of replication. Given the lack of antiviral activity of Baclin lackin the Bcl-2 binding domain, it seems likely that the mechanisms by which Beclin and Bcl-2 inhibit Sindbis virus replication in mouse brain are similar.

The results of the present study do not permit us to evaluate whether the benefical effects of Beclin on Sindbis virus-induced mortality are a consequence of antiviral effects, antiapoptotic effects, or a combination of both. It is not known whether Beclin prevents neural cell death solely as a consequence of reducing Sindbis virus replicaiton in neurons or whether Beclin exerts antiapoptotic effects independently of its effects on viral replication. Further studies examining the effects of Beclin on apoptotic death in response to nonviral stimuli will be necessary to determine whether Beclin, like Bcl-2, functions as a general apoptosis inhibitor. If so, structure-function analyses of Beclin may be helpful to map domains important for antiviral and antiapoptotic function and to identify whether these two properties are interrelated or independent.

Beclin has antiviral activity and that Beclin interacts with the cell death regulator. In dividing cells, inhibition of virus-induced cell death by virally encoded cell death inhibitors such as p35 (7) and adenovirus E1B can increase viral replication (3). However, in nondividing, terminally diffrentiated cells such as neurons, genetic pathways may exist which permit preservation of the life of the cell, without the adverse consequence of increased total viral burden for the organism. Genes such as bcl-2 and beclin that are normally expressed in mammilian neurons may be important components of such pathways.

MATERIALS AND METHODS

Plasmids:

To construct vectors for transient expression in mammalian cells, the open reading frame of human bcl-2, flag epitope-tagged human beclin, and flag epitope-tagged beclin deleted of nucleotides 238 to 453 were cloned into pSG5 (Stratagene). To construct viral cDNA clones, the previously described neurovirulent double subgenomic Sindbis virus vector dsTE12 was used. Full-length flag epitope-tagged human beclin, human beclin containing a stop codon inserted at nucleotide position 270, human beclin containing an in-frame deletion of nucleotides 238 to 453, human bcl-2, and human bcl-2 containing a stop codon at nucleotide position 118 were cloned into the BsxEII site of dsTE12 to generate plasmids SIN/beclin, SIN/beclinstop, SIN/beclin Δbcl-2BD, SIN/bcl-2, and SIN/bcl-2stop, respectively. To construct vectors for yeast two-hybrid studies, the sequences encoding amino acids (aa) 1 to 218 of human bcl-2, 1 to 212 of bcl-$x_S$, 1 to 149 of bcl-$x_S$ and 1 to 171 of bax were cloned into pGBT9 in frame with the GAL4 DNA-binding domain. To avoid difficulties with targeting of proteins to the nucleus, the sequences encoding C-terminal transmembrane domains of bcl-2 family members were omitted. Control pGBT9 plasmids containing lamin (pLAM5') and p53 (pVA3) inserts were obtained from Clontech.

Yeast Two-Hybrid Screen:

*Saccharomyces cerevisiae* SFY526 cells were cotransformed with pGBT9/bcl-2 an $10^6$ cDNA molecules from an adult mouse, brain library fused to a GAL4 activation domain vector (pGAD10:Clontech), plated onto SD medium lacking tryptophan and leucine, incubated at 30° C. for 4 days, and then screened for LacZ activity by a colony lift filter assay. Putative interacting clones were isolated by manipulation in leuB *Escherichia coli*, and further tested against pGBT9 and control plasmids. A positive β-galactosidase reaction between pGBT9/bcl-2 and clone F1 was obtained within 10 to 15 min. For analysis of interactions between Beclin and Bcl-2 family members, pGBT9 plasmids containing bcl-2 family members were cotransformed with fragments of human beclin (1 to 450, 262 to 450, and 1 to 708) fused to the GAL4 activation domain in pGAD424, and transformants were screened for LacZ activity.

Sequencing And Analysis Of Human Beclin:

The partial nucleotide sequence of mouse beclin obtained from sequencing clone F1 was aligned with an overlapping clone GT197 isolated from human breast. Primers immediately upstream and downstream of the predicted open reading frame were used to amplify the coding sequence of human beclin from a normalized human infant brain cDNA library. The resulting PCR products from several independent reactions were cloned into pCRII and sequenced in both directions, using Sequenase (U.S. Biochemical) as well as automated sequencing. The resulting nucleotide sequence and deduced amino acid sequences were used to scan various data banks (GenGank, EMBL, SwissProt, and PIR) for homologous sequences, using the BLAST algorithms. The amino acid sequence was also analyzed by the PROSITE program to identify functional motifs and by the COILS program to identify coiled-coil regions.

Northern Blot Analysis:

Human and mouse multiple tissue blots (Clontech) were hybridized with $^{32}$P randomly labeled human or mouse beclin probes (nucleotides 1 to 485) as instructed by the manufacturer (Clontech). Equal loading [2 μg of poly (A) RNA] was confirmed by hybridization to a β-actin probe.

Production of Recombinant viruses:

The viruses SIN/beclin, SIN/beclinstop, SIN/beclinΔBcl-2BD, SIN/bcl-2, and SIN/bcl-2stop were generated from viral cDNA clones as previously described. Briefly, 5'-capped transcripts were synthesized from cDNA clones linearized with PvuI (for beclin-containing viruses) or XhoI (for bcl-2-containing viruses), transcribed in vitro with SP6 DNA-dependent RNA polymerase, and transfected into BHK cells by using Lipofectin according to the manufacture's instructions. Twenty-four hours after transfection, virus particle-containing supernatants of transfected cell monolayers were collected, frozen in aliquots at 70° C. and used for all subsequent experiments. Titers of stock viruses were determined by plaque assay titration on BHK-21 cells.

Animal Experiments:

Ten-day-old litters of CD1 mice were inoculated intracerebrally into the right cerebral hemisphere with 1,000 PFU of each recombinant virus in 0.03 ml of Hanks' balanced salt solution. For mortality experiments, three to six separate litters were inoculated with each virus, and mortality was determined by daily observation of the mice for 3 weeks after infection. For virus titration and histopathology experiments, three to six mice per experimental group were sacrificed at days 1, 2, and 4 after inoculation. The right cerebral hemisphere was dissected and stored at −70° C. and freeze-thawed tissues were used to prepare 10% homogenates in Hanks' balanced salt solution for plaque assay titration. The Left cerebral hemisphere was fixed by immersion in 3% paraformaldehyde.

Histopathology:

Paraformaldehyde-fixed mouse brains were embedded in paraffin, and a series of 4-$\mu$m parasagittal sections were cut at the level of the olfactory bulb, extending caudally from the bulb to the cerebellum and medulla. For each brain, sequential sections were stained by hematoxylin and eosin to detect histopathology, in situ end labeling (ISEL) to detect apoptotic nuclei, in situ hybridization to detect Sindbis virus RNA, and immunoperoxidase to detect flag-Beclin protein expression. ISEL and in situ hybridization were performed by methods identical to those described previously for SIN/bcl-2 infected mouse brains. Immunoperoxidase staining to detect flag-Beclin protein expression in SIN/beclin-, SIN/beclin$\Delta$Bcl-2BD-, and SIN/beclinstop-infected mouse brains was performed by using the monoclonal anti-flag M2 (5 $\mu$g/ml; VWR) and the avidin-biotin peroxidase method (Vectastain ABC kit; Vector Laboratories) according to the manufacture's instructions.

The number of virus RNA-positive and ISEL-positive cells in each brain section was quantitated with Image-ProPlus software. To calculate the number of positive cells per brain section, nonoverlapping 0.25-mm$^2$ microscopic fields spinning the entire brain section were scanned with a 10× objective and constant settings for brightness, contrast, and threshold values for positive events. The number of positive events (i.e., RNA-positive cells or ISEL-positive cells) for each brain section was determined by adding the sum of all individual fields analyzed. The total number of positive events per brain section was divided by the total area of the brain section to yield the average number of RNA-positive or ISEL-positive cells per square millimeter of brain.

Sections of hippocampus and anterior cortex from an adult human were stained with 843, a polyclonal antibody against a human Beclin peptide corresponding to aa 1 to 15 (1:200 dilution: Eurogenetics, Seraing, Belgium), and human Beclin was detected by the avidin-biotin peroxidase method.

Plasmid Transfection:

Plasmids pSG5/bcl-2 and pSG5/flag-beclin or pSG5/bci-2 and pSG5/flag-beclin$\Delta$Bcl-2BD (1 $\mu$g of each) were transiently transfected into COS7 cells by using Superfect (Qiagen) according to the manufacture's instructions.

Protein Detection:

For immunofluorescence studies, COS7 cells were fixed 24 h after transfection 100% ethanol. Expression of flag-Beclin and flag-mutant Beclin$\Delta$Bcl-2BD mutant constructs was detected with an anti-flag epitope antibody (M2:1:20: VWR) and fluorescein isothiocyanate (FITC)-conjugated horse anti-mouse immunoglobulin G. Bcl-2 expression was detected with a polyclonal rabbit anti-Bcl-2 antibody (1:100; Pharmingen) and rhodamine-conjugated goat anti-rabbit antibody. SERCA (endoplasmic reticulum Ca$^{24}$ ATPase) was detected with an anti-SERCA antibody (1:500: Research Design, Inc.) Western blot analysis to detect flag-Beclin expression in BHK cells infected with SIN/beclin, SIN/beclinstop, and SIN/beclin$\Delta$Bcl-2BD was performed with either antibody M2 (20 $\mu$g/ml) or anti-human Beclin peptide antibody 843 (1:200) and enhanced chemiluminescence detection as instructed by the manufacturer (Amersham).

FRET:

Fluorescence resonance energy transfer (FRET) microscopy was performed as previously described on COS7 cells cotransfected with bcl-2 and beclin expression vectors. The donor (FITC) filter set had the following parameters: excitation (ex)=450 to 490 nm; dichroic mirror (dm)=510 nm; emission (em)=590 long pass. The acceptor (rhodamine) filter set had the following parameters: ex=546 nm; dm=580 nm; em=590 long pass. Images obtained with these two filter sets were used to directly quantify the intensities of each fluorophore. The signal recorded from the FRET filter set (ex=450 to 490 nm; dm=580 nm; em=590 nm long pass) is from energy that has transferred from FITC to rhodamine molecules. A mapping program described previously was used to map fluorescent cells and to quantify the intensity within each cell. Quantitative analysis of these mapped images required solving three equations, one for each filter set, which accounted for the excitation and detection of both labels in all three filter sets as well as the concentrations of the donor and acceptor molecules and the probability of transfer. The measured quantities are expressed as follows, in which the first letter (uppercase) indicates the filler set (A. acceptor; F. FRET; D. Donor) and the second letter (lowercase) indicates the labels present (a. acceptor alone; f. acceptor and donor; d. donor alone). A solution of the equation is E=1/[aconc(RK+1)], where aconc=(AdFf−FdAf)/[(AdFa/Aa)−Fd]; R=(DaFf/Fa−Df)/[aconc ((Fa/Aa)−FdDa/DdAa)−F=FdDf/Dd]; and K is proportional to the product of the ratio of the quantum yield of the two labels and the ratio of the absolute defection efficiencies of the two labels.

Nucleotide Sequence Accession Numbers:

The GenBank accession numbers for human and mouse beclin are AF077301 and AF077302, respectively.

REFERENCES FOR THE THIRD SERIES OF EXPERIMENTS

1. Alsopp, T. E., M. F. Scallan, A. Williams, and J. K. Fazakerley, (1998) Virus infection induces neuronal apoptosis: a comparison with trophic factor withdrawal. Cell Death Differ, 5:50–59;
2. Altshul, S. F., W. Gish, W. Miller, E. W. Meyers, and D. J. Lipman, (1990) Basic local alignment tool. J.Mol. Biol., 215:403–410;
3. Antoni, B. A., P. A. Sabbatini, A. B. Rabson, and White, (1995) Inhibition of apoptosis inhuman immunodeficiency virus-infected cells enhancers virus production and facilitates persistent infection. J. Virol., 69:2324–2392;
4. Boise, L. H., M. Gonzalez-Garcia, C. E. Postema, L. Ding, T. Lindsten, L. A. Turka, X. Mao, G. Nunez, and C. B. Thompson, (1993) Bcl-$x_1$ a bcl-2 related gene that functions as a dominant regulator of apoptotic cell death. Cell, 74:597–608;
5. Cheng, E. H. Y., B. Tevine, L. H. Boise, C. B. Thompson, and J. M. Hardwick, (1996) Bax-independent inhlbition of apoptosis by Bcl-$x_1$ Nature, 379:554–556;
6. Clegg, R. M. (1992) Fluorescence resonance energy transfer and nucleic acids. Meth. Enzy., 211:353–388;
7. Clem. R., and L. K. Miller, (1993) Apoptosis reduces both the in vitro replication and the in vivo infectivity of baculovirus. J. Virol., 67:3730–3738;

8. Friedman, L. S., E. A. estermeyer, E. D. Lynch, C. I. Szabo, L. A. Anderson, P. Dowd, M. K. Lee, S. E. Rowell, J. M. Boyd, and M. C. King, (1994) The search for BRCAL. Cancer Res., 54:6374–6382;
9. Gordon, G. W., G. Berry, X. H. Liang, B. Levine, and B. Herman, (1998) quanzitative fluorescence resonance energy transfer (FRET) measurements using fluorescence microscopy." Biophys, J., 74:2702–2713;
10. Grandgirard, D., E. Studer, L. Monney, T. Belser, I. Fellay, C. Borner, and M. R. Michel, (1998) Alphaviruses induce apoptosis in Bcl-2-overexpressing cells evidence for a caspase-mediated proteolytic inactivation of Bcl-2. EMBO J., 17:1268–1278;
11. Hardwick, J. M., (1997) Virus-induced apoptosis. Adv. Pharmacol, 41:295–336;
12. Herman, B., (1996) Fluorescence microscopy: state of the art p. 1–14. In J. Slavik (ed.), Fluorescent microscopy and fluorescent probes. Plenum Press. New York, N.Y.;
13. Hinshaw, V. S., C. W. Olsen, N. Dybdahl-Sissoko, and D. Evans, (1994) Apoptosis: a mechanism of cell killing by influenza A and B viruses. J. Virol., 68:3667–3673;
14. Jiang, H. H. and B. Levine, Unpublished data.
15. Joe, A. K., H. H. Foo, L. Kleeman, and B. Levine, (1998) The transmembrane domains of Sindbis virus envelope glycoproteins) induce cell death. J. Virol., 72:3935–3943;
16. Krakauer, D. C., and R. J. Payne, (1997) The evolution of virus-induced apoptosis. Proc. R. Soc. Lond. Ser. B, 2641:1757–1762;
17. Levine, B., J. E. Goldman, H. H. Jiang, D. E. Griffin, and J. M. Hardwick, (1996) Bcl-2 protects mice against fatal alphavirus encephalitis. Proc. Natl. Acad. Sci USA, 93:4810–4815;
18. Levine, B., Q. Huang, J. T. Isaacs, J. C. Reed, D. E. Griffin, and J. M. Hardwick, (1993) Conversion of lytic to persisten alphavirus infection by the bcl-2 cellular oncogene. Nature, 361:739–742;
19. Lewis, J., S. L. Wesslingh, D. E. Griffin, and J. M. Hardwick, (1996) Alpha-virus-irduced apoptosis in mouse brains correlates with neurovirulence. J. Virol., 70:1828–1835;
20. Liang, X. H., M. Volkman, R. Klein, B. Herman, and B. Lockett, (1994) Colocalization of tumor suppressor protein p53 and human papillomavirus E6 protein in human cervical carcinoma cell lines. Oncogene 8:2645–2652;
21. Liao, C. L., Y. L. Lin, J. J. Wang, Y. L. Huang, C. T. Yeh, S. H. Ma, and L. K. Chen, (1997) Effect of enforced expression of human bcl-2 on Japanese encephalitis virus-induced apoptosis in cultured cells. J. Virol., 71:5963–5971;
22. Lupas, A., M. Van Dyke, and M. J. Stock, (1991) Predicting coiled coils from protein sequences. Science, 252:1162–1164;
23. Merry, D. E., and S. J. Korsmeyer, (1997) Bcl-2 gene family in the nervous system. Annu. Rev. Neurosci., 20:245–267;
24. Nava, V. E., A. Rosen, M. A. Veliuona, R. J. clem, B. Levine, and J. M. Hardwick, (1998) Sindbis virus induces apoptosis through a caspase-dependent Crm-A-sensitive pathway. J. Virol., 72:452–459;
25. Oberhaus, S. M., R. L. Smith, G. W. Clayton, T. S. Dermody, and K. L. Tyler, (1997) Reovirus infection and tissue injury in the mouse central nervous system as associated with apoptosis. J. Virol., 71:2100–2106;
26. Olsen, C. W., J. C. Kehren, N. R. Dybdahi-Sissoki, and V. S. Hinshaw, (1996) bcl-2 alters influenza virus, yield spread, and hemagglutinin glycosylation. J. Virol., 80:663–666;
27. Oltvai, Z., C. L. Milliman, and S. J. Korsmeyer, (1993) Bcl-2 heterodimerizes in vivo with a conserved homolog, Bax, that accelerates programmed cell death. Cell, 74:609–619;
28. Park, J. R., and D. M. Hockenbery, (1996) Bcl-2, a novel regulator of apoptosis. J. Cell. Biochem., 60:12–17;
29. Pekosz, A., J. Phillips, D. Pleasure, D. Merry, and F. Gonzalez-Scarano, (1996) Induction of apoptosis by LaCrosse virus infection and role of neuronal differentiation and human bcl-2 expression in its prevention. J. Virol., 70:5329–5335;
30. Reed, J. C., (1997) Double identity for proteins of the Bcl-2 family. Nature, 387:773–776;
31. Rodgers, S. E., E. S. Barton, S. M. Oberhaus, B. Pike, C. A. G. Terence, K. L. Tyler, and T. S. Dermody, (1997) Reovirus-induced apoptosis of MDCK cells is not linked to viral yield and is blocked by Bcl-2. J. Virol., 71:2540–2546;
32. Rommens, J. M., F. Durocher, J. McArthur, P. Tonin, J. F. LeBlanc, T. Allen, C. Samson, L. Ferri, S. Narod, K. Morgan, and J. Simard, (1995) Generation of a transcription map at the HSD178 locus centromeric to BRCA1 at 17q21. Genomics, 28:530–542;
33. Root, D. D., (1997) In situ molecular association of dystrophin with action revealed by sensitized emission immuno-resonance energy transfer. Proc. Natl. Acad. Sci. USA, 94:5685–5690;
34. Scallan, M. F., T. E. Allsopp, and J. K. Fazakerley, (1997) bcl-2 acts early to restrict Semliki Forest virus replication and delays virus-induced programmed cell death. J. Virol., 71:1583–1590;
35. Selvin, P. R., (1995) Fluorescence resonance energy transfer. Method Enzymol., 246:300–333;
36. Shen, Y., and T. E. Shenk, (1995) Viruses and apoptosis. Curr. Opin. Genet., 5:105–111;
37. Soares, M. P., M. F. Bonaldo, P. Jelene, L. Su, L. Lawton, and A. Efstradiadis, (1994) Construction and characterization of a normalized cDNA library. Proc. Natl. Acad. Sci. USA, 91:9228–9232;
38. Tangir, J., M. G. Muto, R. S. Berkowitz, W. R. Welch, D. A. Bell, and S. C. Mok, (1996) A 400 kb novel deletion unit centromeric to the BRCA1 gene in sporadic epithelial ovarian cancer. Oncogene, 12:735–740;
39. Teodoro, J. G., and P. E. Branton, (1997) Regulation of apoptosis by viral gene products. J. Virol., 71:1739–1746;
40. Tucker, P. C., E. G. Strauss, R. J. Kuhn, J. H. Strauss, and D. E. Griffin, (1993) Viral determinants of age-dependent virulence of Sindbis virus for mice. J. Virol., 67:4605–4610;
41. Ubol, S., P. C. Tucker, D. E. Griffin, and J. M. Hardwick, (1994) Neurovirulent strains of alphavirus induce apoptosis in bcl-2 expressing cells: role of a single amino acid change in the E2 glycoprotein. Proc. Natl. Acad. Sci. USA, 91:5202–5206; and
42. Yin, X. M., Z. N. Oltvai, and S. J. Korsmeyer, (1994) Bh1 and BH2 domains of Bcl-2 are required for inhibition of apoptosis and heterodimerization with BAX. Nature, 369:321–323.

Figure 22:
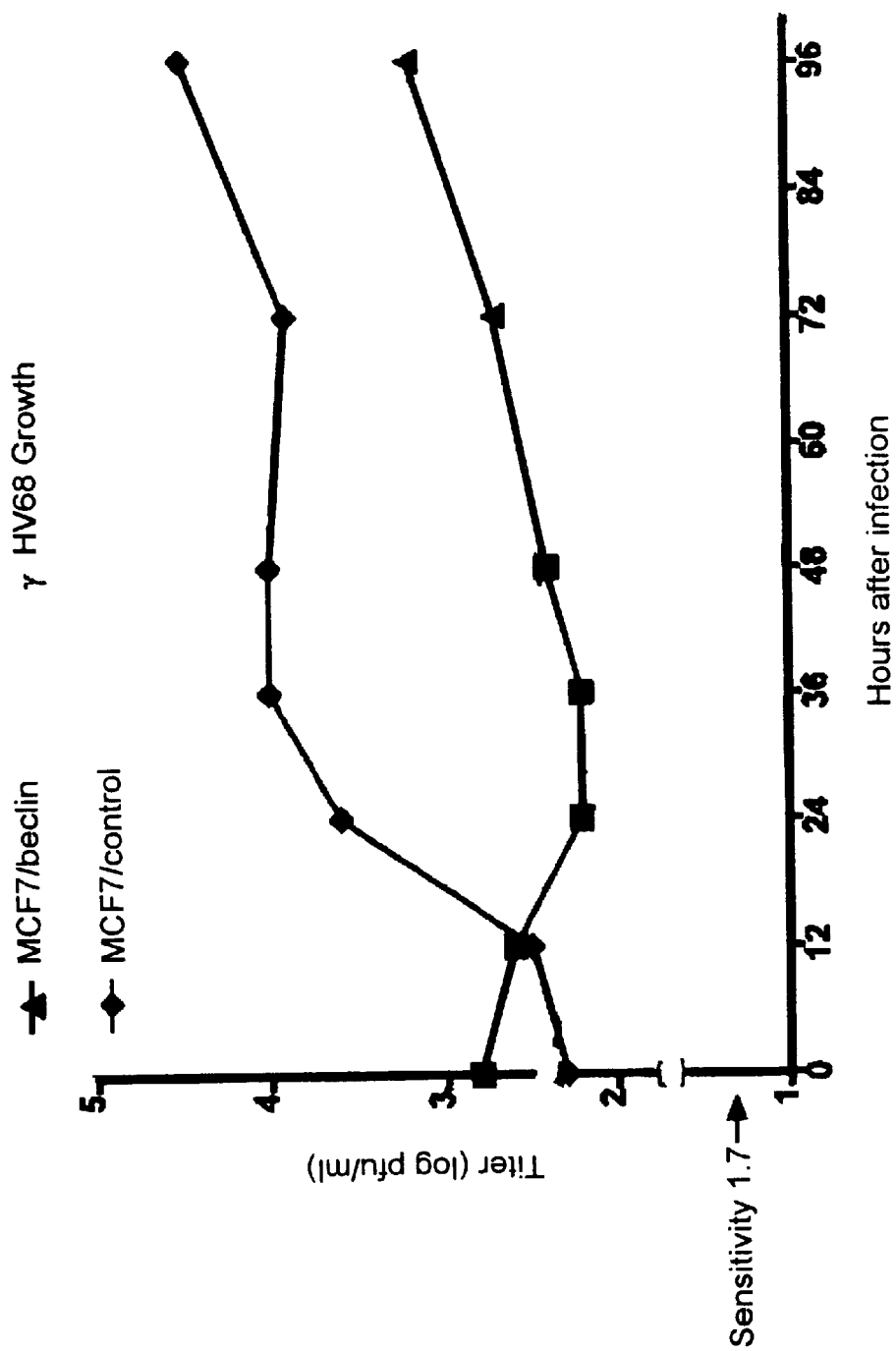
Figure 24A:
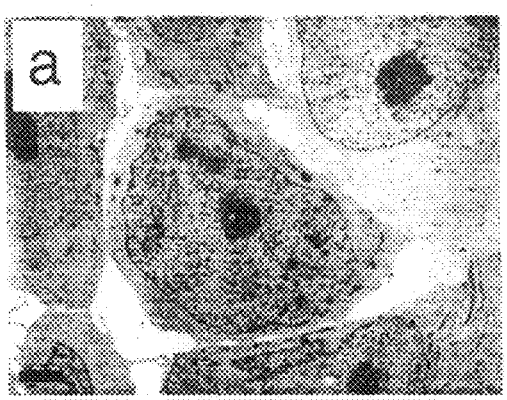
Figure 24B:
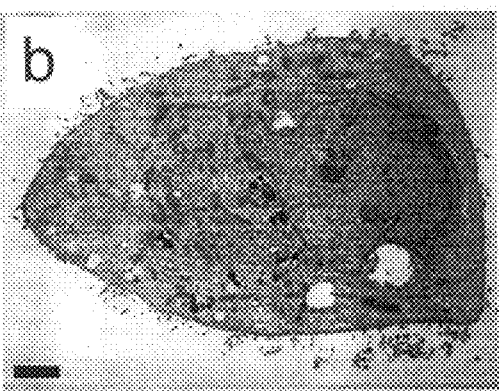
Figure 24C:
Figure 24D:
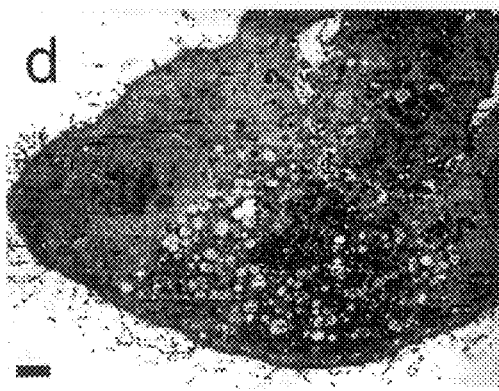
Figure 24E:
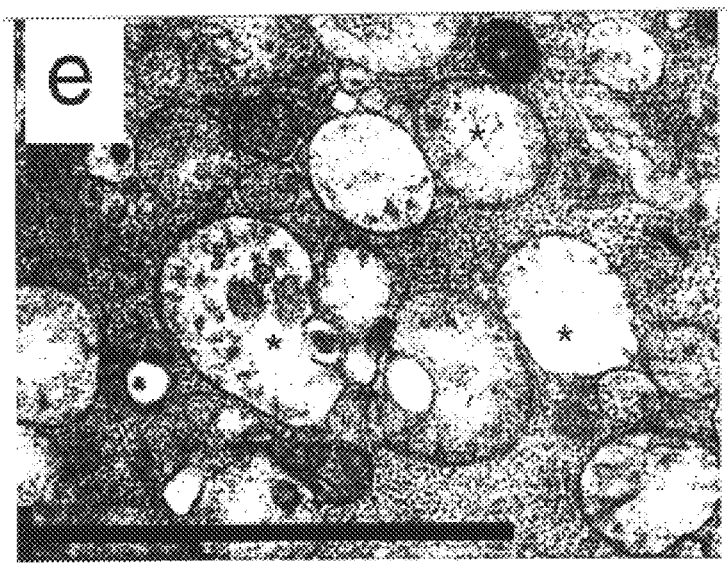
Figure 24F:
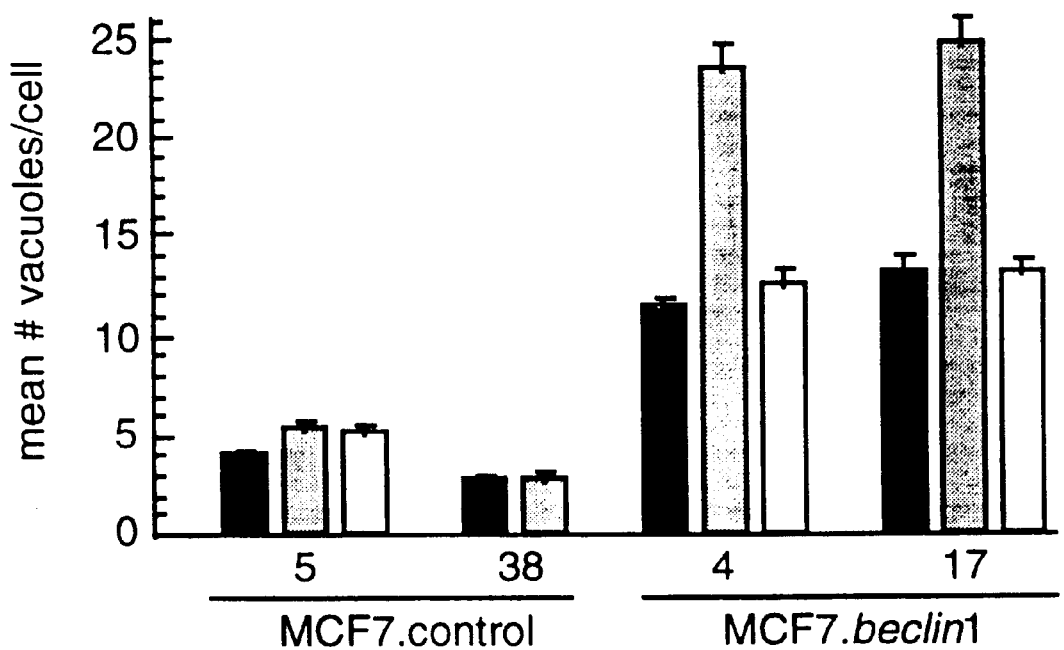

FOURTH SERIES OF EXPERIMENTS:

FIG. 22 shows the growth curve of the virus, a gamma-herpesvirus 68, in human MCF7 breast carcinoma cells that are transfected with an empty vector (MCF7/control cells) or with a vector expressing human beclin (MCF/beclin cells). The results show that there is an approximately 10-fold decrease in the amount of virus in cells which express beclin as compared to the control cells. These data indicate that beclin may also have antiviral effects against members of the herpesvirus family.

In other studies, we have shown that there is a direct interaction between Beclin and Bcl-2-like proteins that are encoded by gammaherpesvirus 68, Kapsosi's Sarcoma Herpesvirus (HHV8) and Epstein Barr virus.

FIFTH SERIES OF EXPERIMENTS

Genetic pathways regulating cellular homeostasis may be important determinants of viral pathogenesis. We have shown that overexpression of several anti-apoptotic genes in virally-infected neurons protects suckling mice from fatal alphavirus encephalitis, suggesting an important role of virus-induced neuronal apoptosis in disease pathogenesis. To further understand the molecular pathways governing neuronal apoptotic death, we performed a yeast two hybrid screen of a mouse brain library, using the anti-apoptosis gene, bcl-2 as a bait. We identified and characterized a novel bcl-2 interacting gene, termed beclin. Beclin plays a role in bcl-2-mediated protection against alphavirus-induced apoptosis in vitro, and beclin overexpression in vivo protects mice against fatal alphavirus encephalitis. Beclin is a candidate tumor suppressor gene which inhibits cellular proliferation in vitro and tumorigenesis in vivo, perhaps by acting as a negative regulator of G2/M. Overexpression of a dominant negative mutant of cdc2, a cyclin-dependent kinase required for the G2/M transition, also protects mice against fatal alphavirus encephalitis. These observations suggest that cell cycle regulators, particularly those involved in G2/M, may be important for virus-induced neuronal death in vivo.

SIXTH SERIES OF EXPERIMENTS

The process of autophagy, or bulk degradation of cellular proteins through an autophagosomic-lysosomal pathway, is important in normal growth control and may be defective in tumor cells. However, little is known about the genetic mediators of autophagy in mammalian cells and whether genetic mediators of autophagy influence tumor development. Recently, 14 genes, the apg genes, have been identified in S. cerevisiae that are required for yeast autophagy[1]. The mammalian gene encoding Beclin 1[2], a novel Bcl-2-interacting, coiled-coil protein, shares structural similarity with the yeast autophagy gene product, Apg6/Vps30p[3,4], and is monoallelically deleted in 40–75% of sporadic human breast cancers and ovarian cancers[5-11]. Here we show, using gene transfer techniques, that beclin 1 promotes autophagy both in autophagy-defective yeast with a targeted disruption of apg6/vps30 and in autophagy-defective human MCF7 breast carcinoma cells. The autophagy-promoting activity of beclin 1 in MCF7 cells is associated with an ability to inhibit MCF7 cellular proliferation, in vitro clonigenicity, and tumorigenesis in nude mice. Furthermore, endogenous Beclin 1 protein expression is frequently undetectable or low in malignant human breast epithelial cell lines and tissue, but is expressed ubiquitously at high levels in normal breast epithelia. Thus, beclin 1 is a mammalian autophagy gene with tumor suppressor function that is expressed at decreased levels in human breast cancer. These findings indicate that there is an evolutionarily conserved genetic link between autophagy and tumor suppressor pathways, and raise the possibility that decreased expression of autophagy proteins may contribute to the development or progression of breast and other human malignancies.

Autophagy is an evolutionarily conserved process that occurs in both yeast and mammalian cells in which there is bulk degradation of cellular contents via an autophagosomal-lysosomal pathway (reviewed in [12]). The process of autophagy liberates free amino acids and nucleotides and enable cells to survive under nutrient deprivation conditions as well as to undergo structural remodeling during differentiation. Protein degradation through an autophagy pathway has also been postulated to serve as a mechanism for negative regulation of cell growth. In support of this theory, cancerous transformation in vitro is associated with decreased rates of autophagic degradation[13,14]. Malignant cell lines display less autophagic activity than their normal counterparts and are less prone to increase autophagic activity in response to serum deprivation or high cell density[15-18]. Furthermore, in rat liver carcinogenesis models, there is an inverse correlation between stage of malignancy and autophagic activity[19]. However, it is not known whether reduced autophagy in tumor cells directly contributes to deregulated cell growth, or alternatively, is the result of malignant transformation.

Genetic screens have identified 14 genes that are required for autophagy in yeast, but no mammalian autophagy genes have as-of-yet been identified[1,3,20-22]. Human Beclin 1 was recently isolated using a yeast two-hybrid screen with Bcl-2 as a bait[2], and shares 24.4% amino acid identity (and 39.1% conservation) with the yeast autophagy gene product, Apg6/Vps30p. Yeast disrupted of apg6/vps30 are defective both in their ability to undergo nitrogen deprivation-induced autophagy[3] as well in their ability to properly sort selective vacuolar proteins[4]. To determine whether Beclin 1 is a functional homolog of Apg6/Vps30p, we investigated whether beclin 1 expression could restore autophagic activity in apg6/vps30-disrupted yeast. Apg6/vps30-disrupted yeast (strain JCY300)[4] were first transformed with the yeast expression vector, pRS424.vps30 which contains the complete apg6/vps30 gene. The open reading frame of apg6/vps30 was then replaced by homologous recombination with the open reading frame of human beclin 1 in the JCY3000+ pRS424.vps30 transformants to generate yeast clones (referred to as JCY3000+pRS424.beclin 1) that express human flag epitope-tagged Beclin 1 (FIG. 23a) under the control of apg6/vps30 regulatory regions. Four hours following transfer to nitrogen-starvation media, we compared the percentage of cells with autophagic bodies within the yeast vacuole in isogenic wild-type yeast (strain SEY620)[4], apg6/vps30-disrupted yeast (strain JCY3000)[4], apg6/vps30-disrupted yeast transformed with pRS424.vps30, apg6/vps30-disrupted yeast transformed with pRS424.beclin 1, and apg6/vps30-disrupted yeast transformed with an empty pRS424 vector. In the presence of PMSF (a protease inhibitor that facilitates detection of autophagic bodies by blocking their degradation[21]), numerous cells with autophagic bodies within the vacuole were seen in wild-type yeast, and apg6/vsp30and beclin 1-transformed Δapg6/vps30 yeast (FIGS. 23b, 23c). In contrast, significantly fewer cells were seen with autophagic bodies within the vacuole among non-transformed Δapg6/vps30 yeast or Δapg6/vps30 yeast transformed with empty pRS424 (p<0.0001, analysis of variance). Thus, beclin 1 complements apg6/vps30 and restores autophagy in autophagy-defective Δapg6/vps30 yeast.

Figure 25A:
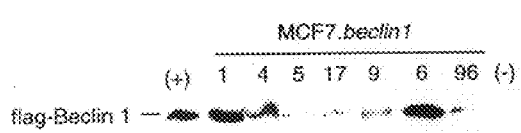

The beclin 1 gene maps to a tumor susceptibility locus on human chromosome 17q21[23,24] that is monoallelically deleted in up to 40–75% of cases of sporadic ovarian and breast carcinomas [5-11,25]. This observation, coupled with the homology between beclin 1 and apg6/Vps30, led us to hypothesize that beclin 1 is a mammalian autophagy gene with tumor suppressor function. To evaluate this hypothesis, we investigated the effects of beclin 1 gene transfer on the autophagic activity and growth properties of MCF7 human breast carcinoma cells. MCF7 cells were originally derived from a patient with 17q21 loss-of-heterozygosity 26 and do not express detectable levels of endogenous Beclin 1 (FIG. 25a). To permit conditional expression of a potential anti-proliferative gene, we stably transfected MCF7 cells with a tetracycline-repressible vector, pTC[27], containing flag-epitope tagged human Beclin 1 (referred to as MCF7.beclin1 clones) or no insert (referred to as MCF7.control clones). Seven MCF7.beclin1 clones which expressed flag-Beclin 1 following tetracycline withdrawal (FIG. 3a) were chosen for further phenotypic analysis.

Electron microscopic analysis was performed of two MCF7.control clones and two MCF7.beclin1 clones which were either maintained in normal growth conditions or subjected to serum and amino acid deprivation for three and a half hours (FIG. 24). In normal cultured cells, serum and amino acid deprivation is a potent inducer of autophagy (reviewed in[28]), which can be recognized at the ultrastructural level as double membrane vacuolar structures containing visible cytoplasmic contents[29-31]. To quantitate the amount of autophagy in different MCF7 clones, we examined 100 cells of each clone and determined the mean number of autophagic vacuoles per cell (FIG. 24f). We found that basal levels of autophagy were significantly higher in MCF7.beclin1 as compared to MCF7.control clones (p<0.0001, analysis of variance; see FIGS. 24a, 24b, 24f). Furthermore, the mean number of vacuoles per cell did not increase following serum and amino acid deprivation in MCF7.control cells (FIGS. 24a, 24c, 24f), whereas serum and amino acid deprivation induced a significant increase in autophagy in MCF7.beclin1 clones (p<0.001, t-test; FIGS. 24b, 24d, 24f). This increase was inhibited by pre-treatment with 3-methyladenine, a nucleotide derivative that inhibits the earliest stages of autophagosome formation[32]. These results indicate that MCF7 human breast carcinoma cells that lack Beclin 1 expression are defective in their capacity to undergo autophagy in response to nutrient deprivation. Enforced beclin 1 expression increases the bassal levels of autophagy in MCF7 cells as well as restores their ability to undergo nutrient deprivation-induced autophagy.

Figure 25B:
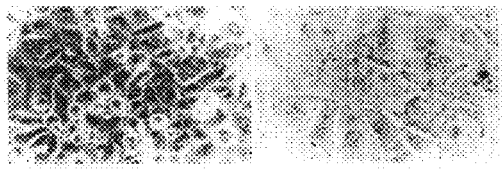
Figure 25D:
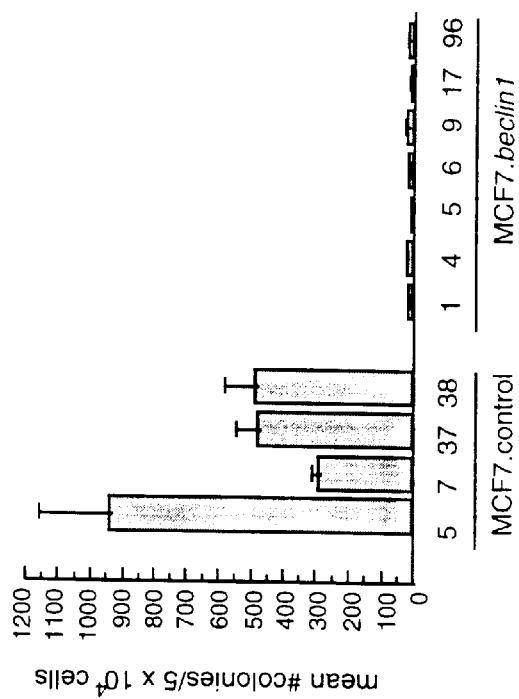
Figure 25C:
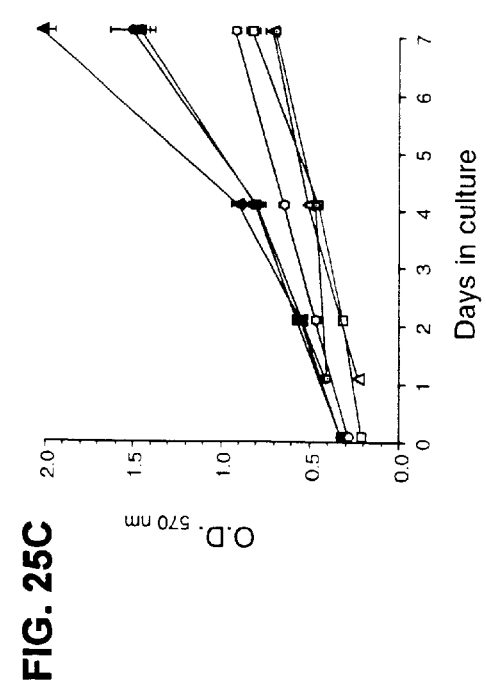
Figure 25E:
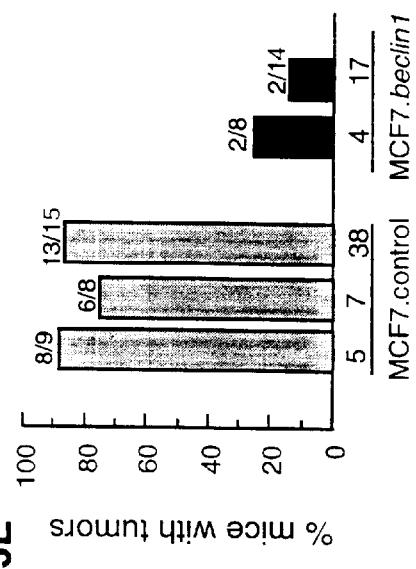
Figure 25F:

To evaluate the effect of beclin 1 on MCF7 growth properties, we compared morphology, cellular proliferation rates, clonigenicity in vitro, and tumorigenicity in vivo of MCF7.beclin1 and MCF7.control clones. MCF7.beclin1 clones displayed several morphologic characteristics consistent with a less malignant phenotype, including flatter appearance, larger size, firmer attachment to tissue culture plate, and increased contact inhibition (see electron and light photomicrographs of representative clones, FIGS. 24a–b, FIG. 25b). As would be predicted based upon the autophagy-promoting effects of beclin 1, all MCF7.beclin1 clones proliferated at a slower rate than MCF7.control clones (FIG. 25c). (The lower rate of proliferation of MCF7.beclin1 cells could not be explained by an increase in cell death, since cell viability determined by trypan blue staining at identical time points was similar among MCF7.beclin1 and MCF7.control cells [data not shown]. All MCF.beclin1 clones were also severely impaired in their clonigenicity in vitro, as compared to MCF7.control clones which formed colonies in soft agar with high efficiency (p<0.0001, Chi-Square) (FIG. 3d). Moreover, the incidence of tumor formation of two MCF7.beclin1 clones that were injected into nude mice was significantly lower than that of three MCF7.control clones (14–25% vs. 75–89%, p<0.0001; Chi-square) (FIG. 25e). The few tumors that did develop in mice injected with MCF7.beclin1 clones had very few flag-Beclin 1 immunoreactive cells whereas almost all MCF7.beclin1 cells were immunoreactive prior to injection into nude mice, indicating that tumor formation was associated with loss of Beclin 1 protein expression (see representative example, FIG. 25f). Taken together, these data demonstrate that Beclin 1 can function as a negative regulator of mammary cell growth and tumorigenesis.

The frequent allelic deletions of beclin 1 in human breast cancer, coupled with its autophagy-promoting and tumor suppressor effects, raise the possibility that functional inactivation of beclin 1 may be important in breast cancer development or progression. A previous study did not identify any coding region mutations in 10 human breast carcinoma cell lines (including 8 cell lines with net allelic deletions of beclin 1 identified by FISH analysis) and did not identify any abnormalities in beclin 1 mRNA expression in human breast carcinoma cell lines[33]. Although these findings do not exclude genomic DNA mutations of beclin 1 in human breast cancer, they do suggest that such mutations may not be frequent. However, certain tumor suppressor genes do not demonstrate bi-allelic mutations in cancer (and fulfill the Knudson two-hit criteria[34] for classification as a tumor suppressor gene) but still demonstrate haplo-insufficiency for tumor suppression. The prototypic example, p27[35], is mono-allelically deleted[36-38] and has low protein expression[39-42] in a high percentage of human cancers; the low protein expression is thought to result from decreased protein stability[40] rather than genetic alterations or altered transcription.

Figure 26A:
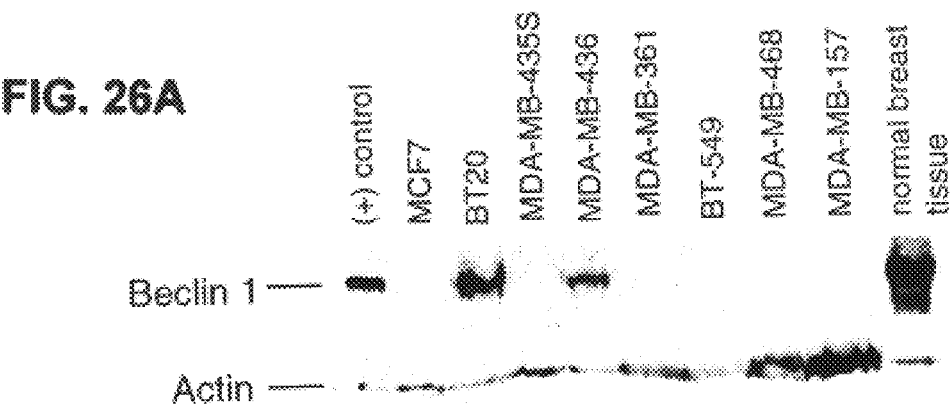
Figure 26B:
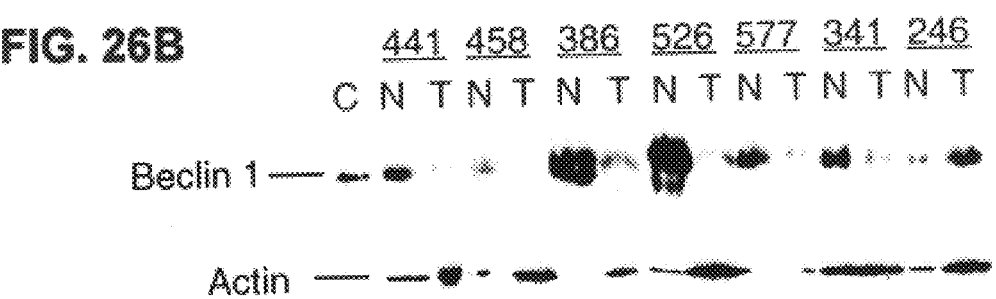

To evaluate whether down-regulation of Beclin 1 protein expression is a mechanism of functional inactivation in human breast cancer, we performed Western blot analysis of human breast carcinoma-derived cell lines and matched normal and malignant breast tissue from patients with invasive sporadic breast carcinoma. Of 11 human breast carcinoma cell lines examined, only three demonstrated detectable Beclin 1 protein expression (see representative samples in FIG. 26a). Of 17 pairs of equivalent volumes of matched normal and malignant breast tissue, 15 samples had higher levels of Beclin 1 expression in normal as compared to tumor tissue, whereas 16 pairs had higher levels of expression of control proteins (e.g. actin, cytokeratin) in the tumor tissue (see representative samples in FIG. 26b). These latter findings demonstrate the despite higher overall levels of protein in breast tumors (which consist primarily of malignant epithelial cells) as compared to normal breast tissue (which consists primarily of fat cells), specific expression of the Beclin 1 protein is usually decreased.

Figure 26C:
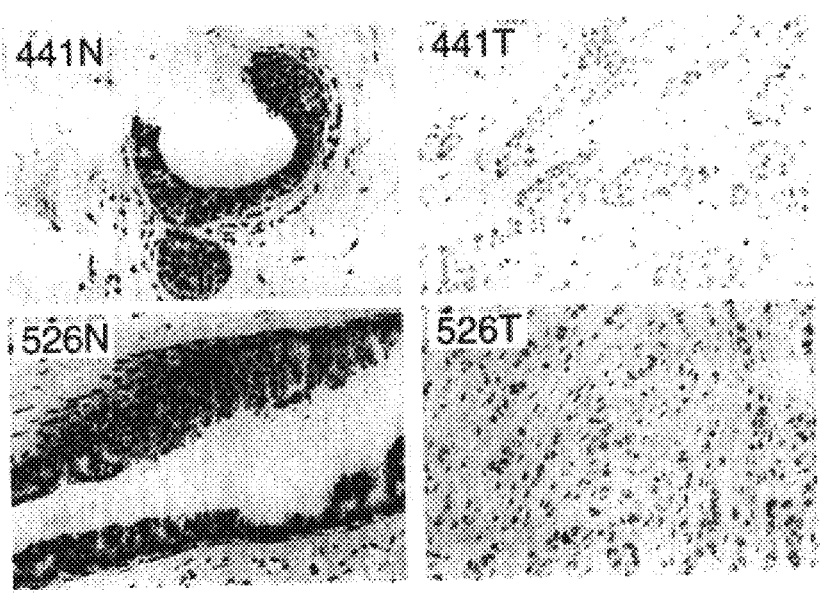

To confirm that the decreased levels of Beclin 1 protein expression in tumors reflected a loss of expression in epithelial cells, we performed immunohistochemical staining of paraffin-embedded sections from 10 of the matched normal and malignant breast samples analyzed by Western blot. We found that in all 10 cases, there was strong Beclin 1 immunoreactivity in all normal breast epithelial cells (see examples in FIG. 26c) (as well as in the media layer of smooth muscle). However, in five of the ten cases, Beclin 1 immunoreactivity was absent in all of the malignant epithelial cells. Immunoperoxidase staining of an additional 22 of cases of breast carcinoma revealed decreased expression of Beclin 1 in malignant as compared to normal breast epithelial cells in 13 cases. Thus, beclin 1 is expressed in normal breast epithelial cells, but its expression is commonly decreased in malignant breast epithelial cells.

Figure 27:

Reduced levels of Beclin 1, an autophagy and tumor suppressor protein, in human breast carcinoma suggests that therapeutic compounds that increase Beclin 1 protein expression in human breast carcinoma cells may be effective treatments for human breast cancer. This hypothesis was evaluated by determining whether tamoxifen, an anti-estrogen compound that is used in treating breast cancer, increases the expression of Beclin 1 in MCF7 human breast carcinoma cells. The levels of Beclin 1 antibody, 843, at serial time points after treatment with 10 mm of tamoxifen. The results (FIG. 27) indicate that Beclin 1 protein expression is barely detectable in untreated MCF7 cells and that within 72 hours after tamoxifen treatment, Beclin 1 protein expression is significantly increased in MCF7 cells. The ability of tamoxifen, an effective anti-breast tumor agent, to increase Beclin 1 expression in MCF7 human breast carcinoma cells supports the hypothesis that induction of Beclin 1 expression in human breast cancer may be therapeutically effective.

In summary, data indicates that beclin 1 is the first identified mammalian gene with a role in mediating autophagy. Prior studies have indicated that signalling through the S6 kinase pathway exerts inhibitory effects on mammalian autophagy[43], but no genes have been identified that play a role in the execution of autophagy in mammalian cells. Human homologs exist of other yeast autophagy genes[44,45], and given the functional evolutionary conservation between beclin 1 and apg6/vps30, it seems likely that these human homologs will also be found to play a role in mammalian autophagy. Modification of one of the human homologues, human Apg5p, in apoptotic cells[44], has led others to postulate that yeast autophagy and mammalian apoptosis may share common pathways[46]. Interestingly, Beclin 1 interacts with the apoptosis regulator, Bcl-2[2], further suggesting a possible interrelationship between autophagy and apoptosis. However, at least in the context of a CNS viral infection, beclin 1 has anti-apoptotic, not pro-apoptotic effects[2], consistent with a model in which autophagy enables stressed cells to survive rather than a model in which autophagy machinery is used to execute apoptotic death.

A common feature of malignant cells is that they fail to respond to normal growth inhibitory and autophagy-stimulatory signals such as nutrient deprivation and high density[15-18]. Enforced expression of an autophagy gene not only restores nutrient deprivation-induced autophagy in breast carcinoma cells bit also suppresses their malignant phenotype suggest that autophagy is a fundamental mechanism for preventing the deregulated growth of tumor cells. Furthermore, the frequent monoallelic deletions and decreased expression of beclin 1 in human breast cancer suggest that specific molecular alterations in autophagy pathways may contribute to tumorigenesis. It may therefore be possible to develop new anti-cancer therapeutic strategies that increase the expression of autophagy genes such as beclin 1, and thereby, restore normal growth control.

MATERIALS AND METHODS

Yeast strains, media, and genetic methods. The Saccharomyces cerevisiae strains used for cloning, immunochemical analysis, and autophagy assays were SEY6210 (MATαleu2-3, 112 ura3-52 hisΔ200 trp1-Δ901 lys2-801 suc2-Δ9) and JCY3000 (SEY6210 Δvps30::HIS3). JCY3000 yeast were transformed with pRS.vps30 with the procedure of Eble et al[47] and flag-beclin 1 was substituted for the open reading frame of apg6/vps30 in pRS.vps30 using recombination-mediated PCR-directed plasmid construction in vivo[48]. Yeast were grown in either YEPD, in synthetic complete medium, SD, lacking trp for transformation selection, or in SD(-N) for starvation experiments, consisting of 2% glucose with 1.7 g/l of yeast nitrogen base without amino acids and without ammonium sulfate.

Mammalian cell lines and transfections. Human breast carcinoma cell lines were obtained from ATCC and maintained according to ATCC instructions. MCF7 cells were transfected using liposome-mediated transfer with the plasmid, pTC[27], containing flag epitope-tagged human beclin 1 cloned into the Nhe I site or no insert. Stable transfectants were selected for with 300 μg/ml hygromycin and maintained in 2 μg/ml tetracycline; tetracycline was withdrawn five days before all experiments.

Immunochemical procedures. Yeast and mammalian cell lyscates were subjected to SDS-PAGE, followed by immunoblotting with anti-flag monoclonal (M2, VWR; 20 μg/ml) or polyclonal antibody (Zymed, 1:200 dilution), polyclonal anti-Beclin 1 antibody 843[2] (1:200 dilution), or anti-actin (Boehringer Mannheim, 1:400 dilution). Immunoperoxidase staining to detect flag-Beclin 1 and endogenous Beclin 1 expression was performed using M2 (5 μg/ml) or 843 (1:100), respectively, with the ABC method according to the manufacturer's instructions (Vector Laboratories).

Autophagy analysis. Yeast strains were grown overnight in YEPD or liquid SD-trp, transferred to SD (-N) at a concentration of $2 \times 10^7$ cells/ml, incubated for four hours in the presence or absence of 1 mM PMSF, visualized using DIC optics with a Plan-Apochromat 100×1.4 NA objective, and imaged with a cooled CCD camera using IP Lab software. MCF7 cells were grown in normal media or serum and amino-acid free media, fixed with 2.5% glutaraldehyde, postfixed with 1% $OsO_4$, and embedded in Lx-112 (Ladd Research Industries, Inc.) and Embed-812 (E.M.S.). Thin sections were cut on MT-700 RMC, stained with uranyl acetate and lead citrate, and examined by transmission electron microscopy using a JEOL JEM-1200 EXII.

Proliferation, clonigenicity and tumorigenicity assays. MCF7 clones were seeded in 96 well plates at a density of $5 \times 10^3$ cells per well, and cell proliferation was measured at serial time points using the MTT Cell Proliferation Kit (Boehringer Mannheim) according to the manufacturer's instructions. MCF7 clones were plated in triplicate at a density of $5 \times 10^4$ cells per 35 mm-well in semi-solid medium (soft agar) as described[49] and colonies were counted at 21 days. Five week-old NCR nude mice (Taconic Farms) were implanted with slow release estrogen pellets (1.7 mg/60 lay, Innovative Research of America) and injected subcutaneously with $5 \times 10^6$ tumor cells. Animals were necropsied eight weeks after injection for gross and histologic confirmation of tumor and analysis of flag Beclin 1 protein expression. Autophagy is an evolutionarily conserved process that occurs in both yeast and mammalian cells in which there is bulk degradation of cellular contents via an autophagsomal-lysosomal pathway. The process or autophagy liberates free amino acids and nucleotides and enables cells to survive under nutrient deprivation conditions as well as to undergo structural remodeling during differentiation. In mammalian cells, the process of autophagy is thought to occur in distinct stages, involving invagination of the rough endoplasmic reticulum to form an early autophagosome; fusion of the autophagosome with a vesicle containing lysosomal autophagosome the formation membrane proteins (e.g. LGP120 and H$^+$-ATPase) to become an acidic late autophagosome; acquisition of acid hydrolases and hydrolysis of its vacuolar contents; and transformation into a residual body. In yeast, the sequence of events is essentially the same, with formation of an autophagosome; fusion of the autophagosome to the vacuole, which is equivalent to a lysosome in mammalian cells; delivery of the inner membrane structures of the autophagosome to the vacuole as autophagic bodies; and destruction of the autophagic bodies by yeast proteinases.

For decades, it has been postulated that protein degradation through an autophagy pathway may serve as an important mechanism for negative regulation of cell growth. Support for this hypothesis stems from the following observations: In addition to changes in rates of protein synthesis, cell growth rate can be modulated by changes in the rate of protein degradation. Negative control of cell growth through protein degradation is generally exerted by an autophagic pathway. Cancerous transformation in vitro may be associated with changes in protein degradation. Malignant cell lines usually display lower protein degrading activity than their normal counterparts and may be less prone to increase their degradation rate in response to serum deprivation or high cell density. In rat liver carcinogenesis models, a mild reduction in lysosomal protein degradation and autophagic activity is observed at a preneoplastic stags and more significant reduction is observed n primary hepatocellular tumor cells.

Together, these observations raise the interesting possibility that defects in autophagy pathways may contribute to deregulated cell growth. However, all data to date regarding the relationship between autophagy and negative growth control has been of a correlative nature; i.e. decreased autophagy has been observed in cells with increased growth rates but it is not known whether the reduced autophagy in tumor cells is a cause or effect (or associated epiphenomenon) of malignant transformation. Further studies are required to evaluate whether there is a causal relationship between autophagy dysregulation and tumorigenesis.

The recent characterization of autophagy in yeast has provided the opportunity to use genetic approaches to investigate the molecular control of autophagy. Genetic screens in the yeast *Saccharomyces cerevisiae* identified 14 genes, termed apg genes, that are required for yeast autophagy. Mutation or disruption of these genes prevents yeast from forming autophagic bodies when subjected to nutrient deprivation, from surviving during conditions of nutrient deprivation, and from undergoing sporulation/differentiation. The original cloning of the apg genes revealed little about their function. However, recent advances have shed more light on the possible functions of the individual apg genes. First, Matsuura et al. have shown that Apg1p is a novel type of serine/threonine protein kinase, providing evidence for involvement of protein phosphorylation in the regulation of autophagy. Second, Mizushima et al. have shown that a unique covalent-modification system is essential for autophagy to occur in yeast. The carboxy-terminal glycine residue of Apg12p is conjugated to a lysine residue of Apg5p, and Apg7p is a ubiquitin-E1 like enzyme that is required for the conjugation of Apg12p and Apg5p. Third, the yeast autophagy gene product, Apg6p, was independently identified as Vps30p in a screen for yeast proteins involved in vacuolar protein sorting. Yeast with a targeted disruption of apg6/vps30 are unable to properly sort selective vacuolar hydrolases, such as carboxypeptidase Y.

Although autophagy has been recognized as an important process in mammalian cells for the past four decades, virtually nothing is known about the genes involved in mammalian autophagy. The existence of human homologues of some of the recently cloned yeast autophagy genes provides new opportunities to make important discoveries about the molecular mediators of mammalian autophagy. The apg5 and apg12 genes both have human homologues, suggesting that there is a conserved pathway of ubiquitin-dependent protein degradation in yeast and mammalian cells. In addition, our laboratory has recently cloned and characterized the human homolog of the yeast autophagy gene, apg6/vps30, which is a novel gene termed beclin 1. We isolated beclin 1 by virtue of the interaction of its encoded gene product with the anti-apoptotic protein, Bcl-2, in a yeast two-hybrid screen. In previously publish(ed studies, we demonstrated that beclin 1 is ubiquitously expressed in mouse and human tissues and that overexpression of wild-type Beclin 1, but not Beclin 1 lacking the Bcl-2 binding domain, inhibits Sindbis virus-induced apoptosis in neurons. In addition to cellular Bcl-2 family members, we have also found that viral Bcl-2-like proteins encoded by oncogenic gammaherpesviruses interact with Beclin 1.

Yeast and mammalian autophagy is regulated by a variety of environmental factors, the most influential being availability of amino acids. The formation of the autophagosome is modulated by a group of regulatory amino acids: leucine, glutmaine, proline, methionine, histidine, tryptophan, tyrosine and phenylanalanine. When these amino acids are removed from the culture medium, both the rate of protein and RNA degradation and the number of autophagic vacules increase. Amino acids are considered to be primary regulators of autophagy, since they can override most forms of induced proteolysis in the absence of hormones. However, hormones and growth factors also play a role in the regulation of autophagy. For example, insulin inhibits the degradation of proteins and RNA and the formation of autophagosomes in many cell types. Glucagon, isoproterenol and cyclic AMP stimulate protein degradation and autophagy in liver cells, but have opposite effects in cardiac myocytes. In addition, proteolysis induced by nutrient stress can be suppressed by EGG and IGF-1 in many cell types Recent evidence suggests that these environmental/hormonal factors may regulate autophagy through an evolutionarily conserved signalling pathway involving TOR in yeast and RAFT1 in mammalian cells. A model is emerging in which TOR, a phosphatidylinositol kinase homologue and its mammalian counterpart, RAFT1, are thought to negatively regulate induction of autophagy by activation of p70 S6 serine/threonine kinase which in turn, phosphorylates the ribosomal protein S6. Phosphorylation of ribosomal protein S6 is simultaneously inhibitory for autophagy and stimulatory for protein synthesis and cell cycle progression through G1 in response to mitogenic signals. Consistent with this model, treatment of cells with autophagy inhibitory stimuli such as insulin and amino acids is associated with linear increases in S6 phosphorylation, and linear decreases are seen in p70 S6 kinase activation and S6 phosphorylation under autophagy promoting conditions. The evidence for a negative regulatory role of TOR in yeast autophagy is two-fold. First, rapamycin, an inhibitor of TOR function, induces autophagy even in yeast cells growing in nutrient-rich medium. Second, a temperature sensitive TOR mutant leads to induction of autophagy at a nonpermissive temperature. (Of note, rapamycin inactivation of TOR in yeast also induces a G0 growth arrest. The site of action of TOR is upstream of the Apg proteins, as rapamycin does not induce autophagy in yeast with disrupted apg genes.

These observations suggest that a TOR/RAFT1-S6 kinase signalling pathway may simultaneously regulate the balance between cell proliferation in response to mitogens and negative cell growth via autophagy. The TOR/RAFT1 signal transduction pathway is thought to provide an important checkpoint control, linking amino acid sufficiency to the control of peptide chain initiation. Abnormal activation of S6 kinase activity is postulated to be a potential mechanism for uncontrolled cell growth and oncogenesis. An interesting possibility s that inactivation of downstream targets of TOR involved in the autophagy arm of the pathway, such as the Apg proteins, could also contribute to deregulated cell growth.

In addition to a role in apoptosis regulation, beclin 1, the human homolog of the yeast autophagy gene, apg6/vps30, is a candidate tumor suppressor gene. We originally became interested in the possibility that beclin 1 is a candidate tumor suppressor gene because it maps to a region of chromosome 17q21 that is frequently monoallelically deleted in sporadic human breast and ovarian cancer. While the tumor suppressor gene BRCA1 maps to this region, BRCA1 is thought to only be important in the familial and not sporadic forms of these diseases. Most cancer geneticists believe that one or more tumor suppressor genes within this region are important in the sporadic forms of breast and ovarian cancer.

Preliminary data obtained to date raise the possibility that beclin 1 may be a tumor suppressor gene that demonstrates haplo-insufficiency. (i.e. monallelic deletion confers susceptibility to tumorigenesis, a concept recently demonstrated with p27 +/– mice) Several previous studies have shown deletions of the beclin 1-containing region of chromosome 17q21 in up to 50% of cases of sporadic breast cancer and 75% of cases of sporadic ovarian cancer ((including some cases that did not have deletions of the BRCA1 region of chromosome 17q21]). In human breast cancer cell lines, we confirmed by FISH analysis that beclin 1 is frequently allelically deleted; 9 of 22 cell lines examined contained net beclin 1 deletions. In a mutation analysis of 8 cases of sporadic ovarian cancer with 17q21 LOH and 10 breast cancer cell lines with net beclin 1 deletions, we have not detected any mutations within the beclin 1 coding region. However, we have found that Beclin 1 protein is expressed ubiquitously in normal breast epithelial cells, but that its expression is frequently absent or decreased in human breast cancer cell lines and in human breast cancer tissue. Furthermore, in the preliminary data section of this proposal, we present evidence that enforced Beclin 1 expression in human MCF7 breast carcinoma cells delays cell proliferation, interferes with anchorage-independent growth, and decreases tumor formation in nude mice. Thus, beclin 1 is frequently deleted in human breast cancers, its expression is frequently down-regulated in human breast cancers, and it can suppress mammary tumorigenesis. Taken together, these observations suggest that beclin 1 is a strong candidate tumor suppressor gene. (In the absence of evidence of bi-allelic inactivation of beclin 1 in human cancers, functional studies in beclin 1 –/+ mice will be required for sore definitive proof that it is a haplo-insufficient tumor suppressor.

Impairment of autophagy may contribute to the development or progression of human tumors. However, there has been no direct evidence implying a role for deregulation of autophagy in tumorigenesis; the reductions in autophagy observed in malignant cells could be secondary or epiphenomenon that are a consequence of other changes in the cells. Our finding that a mammalian homolog of a yeast gene required for autophagy is a candidate tumor suppressor provides the first suggestion of a possible genetic link between autophagic and tumor suppressor pathways. In the preliminary data section, we present evidence that beclin 1 possesses an evolutionarily conserved role in autophagy, that beclin 1 has tumor suppressor function in breast carcinoma cells, and that beclin 1 expression is down-regulated in breast cancer. These data raise the possibility that the tumor suppressor function of beclin 1 may be related to a mechanism involving autophagy induction and that down-regulation of autophagy proteins may contribute to the development and/or progression of breast and other human cancers. In this proposal, we plan to further explore the relationship between the role of beclin 1 in autophagy and tumorgenesis. Such studies are expected to provide fundamental insights about the interrelationship between autophagy and the mechanisms underlying the growth of human tumors.

REFERENCES FOR THE SIXTH SERIES OF EXPERIMENTS

1. Tsukada, M. & Ohsumi, Y. Isolation and characterization of autophagy-defective mutants of *Saccharomyces cerevisiae*. FEBS 333, 169–174 (1993).
2. Liang, X. H. et al. Protection against fatal Sindbis virus encephalitis by Beclin, a novel Bcl-2-interacting protein. *J Virol* 72, 8586–8596 (1998).
3. Kametaka, S., T, T. O., Ohsumi, M. & Ohsumi, Y. Apg14p and Apg6/Vps30p form a protein complex essential for autophagy in the yeast, *Saccharomyces cerevisiae*. *J Biol Chem* 273, 22284–22291 (1998).
4. Seaman, M. N. J., Marcusson, E. G., Cereghino, J. L. & Emr, S. D. Endosome to golgi retrieval of the vacuolar protein sorting receptor, Vps10p, requires the function of the VPS29, VPS30, and VPS35 gene products. *J Cell Biol* 137, 79–92 (1997).
5. Cropp, C. S., Champeme, M. H., Lidereau, R. & Callahan, R. Identification of three regions on chromosome 17q in primary human breast carcinomas which are frequently deleted. *Cancer Res* 53,3382–3385 (1993).
6. Eccles, D. M., Russell, S. E. H., Haites, N. E. & T.A.O.C.G., G. Early loss of heterozygosity on 17q in ovarian cancer. *Oncogene* 7, 2069–2072 (1992).
7. Futreal, P. A. & al, e. Detection of frequent allelic loss on proximal chromosome 17q in sporadic breast carcinoma using microsatellite length polymorphisms. *Cancer Res* 52, 2624–2627 (1992).
8. Russell, S. E. H., Hickey, G. I., Lowry, W. S. & Atkinson, R. J. Allele loss from chomosome 17 in ovarian cancer. *Oncogene* 5, 1581–1583 (1990).
9. Saito, H. & al, e. Detailed deletion mapping of chromosome 17q in ovarian and breast cancers: 2-cM region on 17q21.3 often and commonly deleted in tumors. *Cancer Res* 53, 3382–3385 (1993).
10. Tangir, J. & al, e. A 400 kb novel deletion unit centromeric to the BRCA1 gene in sporadic epithelial ovarian cancer. *Oncogene* 12, 735–740 (1996).
11. Yang-Feng & al., e. Allelic loss in ovarian cancer. *Int J Cancer* 54, 546–551 (1993).
12. Dunn, W. A. J. Autophagy and related mechanisms of lysosomal-mediated protein degradation. *Trends in Cell Bio.* 4, 139–143 (1994).

13. Bradley, M. O. Regulation of protein degradation in normal and transformed human cells. *J Biol Chem* 252, 5310–5315 (1977).
14. Lee, H.-K., Jones, R. T., Myers, R. A. M. & Marzella, L. Regulation of protein degradation in normal and transformed human bronchial epithelial cells in culture. *Arch Biochem Biophys* 296, 271–278 (1992).
15. Gronostajski, R. M. & Pardee, A. B. Protein degradation in 3T3 and tumorigenic transformed 3T3 cells. *J Cell Physiol* 119, 127–132 (1984).
16. Gunn, J. M., Clark, M. G., Knowles, S. E., Hopgood, M. F. & Ballard, F. J. Reduced rates of proteolysis in transformed cells. *Nature* 266, 58–60 (1977).
17. Knecht, E., Hernandez-Yago, J. & Grisolia, S. Regulation of lysosomal autophagy in transformed and non-transformed mouse fibroblasts under several growth conditions. *Exp. Cell. Res.* 154, 224–232 (1.984).
18. Otsuka, H. & Moskowitz, M. Differences in the rates of protein degradation in untransformed and transformed cell lines. *Exp Cell Res* 112, 127–135 (1978).
19. Kisen, G. O. et al. Reduced autophagic activity in primary rat hepatocellular carcinoma and ascites hepatoma cells. *Carcinogenesis* 14, 2501–2505 (1993).
20. Funakoshi, T., Matsuura, A., Noda, T. & Ohsumi, Y. Analyses of APG13 gene involved in autophagy in yeast, Saccharomyces cerevisiae. *Gene* 192, 207–213 (1997).
21. Kametaka, S., Matsuura, A., Wada, Y. & Ohsumi, Y. Structural and functional analyses of APG5, a gene involved in autophagy in yeast. *Gene* 178, 139–143 (1996).
22. Matsuura, A., Tsukada, M., Wada, Y. & Ohsumi, Y. Apg1p, a novel protein kinase required for the autophagic process in Saccharomyces cerevisiae. *Gene* 192, 245–250 (1997).
23. Friedman, L. S. et al. The search for BRCA1. *Cancer Res*: 54, 6374–6382 (1994).
24. Rommens, J. M. etu al. Generation of a transcription map at the HSD17B locus centromeric to BRCA1 at 17q21. *Genomics* 28, 530–542 (1995).
25. Sabatini, D. M., Erdjument-Bromage, H., Lui, M., Tempst, P. & Snyder, S. H. RAFT1: a mammalian protein that binds to FKBP12 in a rapamycin-dependent fashion and is homologous to yeast TORS. *Cell* 78, 35–43 (1994).
26. Holt, J. T. et al. Growth retardation and tumour inhibition by BRCA1. *Mature Genetics*, 12, 298–302 (1996).
27. Wu, K.-J., Polack, A. & Dalla-Favera, R. Coordinated regulation of iron-controlling genes, H-ferritin and IRP2, by c-MYC. *Science* 283, 676–679 (1999).
28. Mortimore, G. E. & Poso, A. R. Amino acid control of intracellular protein degradation. *Methods Enzymol* 166, 461–476 (1988).
29. Dunn, W. A. Studies on the mechanisms of autophagy; formation of the autophagic vacuole. *J Cell Biol* 110, 1923–1933 (1990).
30. Dunn, W. A. Studies on the mechanisms of autophagy; maturation of the autophagic vacuole. *J Cell Biol*, 1935–1945 (1990).
31. Mitchener, J. S., Shelburne, J. D., Bradford, W. D. & Hawkins, H. K. Cellular autophagocytosis induced by deprivation of serum and amino acids in HeLa cells. *Am J Pathol* 83, 485–498 (1976).
32. Seglen, P. O. & Gordon, P. B. 3-methyladenine: specific inhibitor of autophagic/lysosomal protein degradation in isolated rat hepatocytes. *Proc. Natl. Acad. Sci. USA* 79, 1889–1892 (1982).
33. Aita, V. M. et al. Cloning and genomic structure of beclin 1, a candidate tumor suppressor gene on chromosome 17q21. Submitted, submitted (1999).
34. Knudson, A. G. J. Hereditary cancer, oncogenes, and antioncogenes. *Cancer Res* 5, 1437–1443 (1985).
35. Fero, M. L., Randel, E., Gurley, K. e., Roberts, J. M. & Kemp, C. J. The murine gene p27kip1 is haplo-insufficient for tumour suppression. *Nature* 396, 177–180 (1998).
36. Pietenpol, J. A. & al, e. Assignment of the human p27Kip1 gene to 12p13 and its analysis in leukemias. *Cancer Res* 88, 1206–1210 (1995).
37. Stegmaier, K. & al., e. Mutational analysis of the candidate tumor suppressor genes TEL and KIP1 in childhood acute lymphoblsatic leukemia. *Cancer Res* 56, 1413–1417 (1996).
38. Takeuchi, S. & al., e. Frequency loss of heterozygosity in region of the IP1 locus in non-small cell lung cancer: evidence for a new tumor suppressor gene on short arm of chromosome 12. *Cancer Res.* 56, 738–740 (1996).
39. Esposito, V. & al., e. Prognostic role of the cyclin-dependent kinase inhibitor p27 in non-small cell lung cancer. *Cancer Res.* 57, 3381–3385 (1997).
40. Loda, M. & al., e. Increased proteasome-dependent degradation of the cyclin-dependent kinase inhibitor p27 in agressive colorectal carcinomas. *Nature Med* 3, 231–234 (1997).
41. Porter, P. L. et al Expression of cell-cycle regulators p27kip1 and cyclin E, alone and in combination, correlate with survival in young breast cancer patients. *Nature Med* 3, 222–225 (1997).
42. Hayette, S. & al., e. Molecular analysis of cyclin-dependent kinase inhibitors in human leukemias. *Leukemia* (1997).
43. Blommaart, E. F. C., Luiken, J. J. F. P., Blommaart, P. J. E., vanwoerkom, G. M. & Meijer, A. J. Phosphorylation of ribosomal protein S6 is inhibitory for autophagy in isolated rat hepatocytes. *J Biol Chem* 270, 2320–2326 (1995).
44. Hammond, E. et al. Homology between a human apoptosis specific protein and the product of APG5, a gene involved in autophagy in yeast. *FEBS Letters* 425, 391–395 (1998).
45. Mizushima, N. et al. A protein conjugation system essential for autophagy. *Nature* 395, 395–398 (1998).
46. Jentsch, S. & Ulrich, H. D. Ubiquitous deja vu. *Nature* 395, 321–323 (1998).
47. Eble, R. A simple and efficient procedure for transformation of yeasts. *Biotechniques* 13, 18–20 (1992).
48. Oldenburg, K. R., vo, K. T., Michaelis, S. & Paddon, C. Recombination-mediated PCR-directed plasmid construction in vivo in yeast. *Nucleic Acids Res.* 25, 451–452 (1997).
49. Jiang, W. & al., e. Overexpression of cyclin D1 in rat fibroblasts causes abnormalities in growth control, cell cycle progression and gene expression. *Oncogene* 8, 3447–3457 (1993).

What is claimed is:

1. A method for treating a subject afflicted ovarian cancer, breast cancer or prostate cancer which comprises administering to the subject a therapeutically effective amount of beclin so as to restore cell growth control in the subject.

2. A method for restoring cell growth control in a cancerous ovarian, breast or prostate cell comprising introducing into the cell a beclin-encoding nucleic acid that causes increased beclin expression in the cell.

3. A method for restoring cell growth control in a cancerous ovarian, breast or prostate cell comprising contacting the cell with an effective amount of beclin.

* * * * *